United States Patent
Zhang et al.

(10) Patent No.: US 10,351,559 B2
(45) Date of Patent: Jul. 16, 2019

(54) MALEATE SALTS OF A B-RAF KINASE INHIBITOR, CRYSTALLINE FORMS, METHODS OF PREPARATION, AND USES THEREFORE

(71) Applicant: BeiGene, Ltd., Camana Bay, Grand Cayman (KY)

(72) Inventors: Guoliang Zhang, Beijing (CN); Changyou Zhou, Princeton, NJ (US)

(73) Assignee: BEIGENE, LTD., Grand Cayman (KY)

( * ) Notice: Subject to any disclaimer, the term of this patent is extended or adjusted under 35 U.S.C. 154(b) by 0 days.

(21) Appl. No.: 15/565,807

(22) PCT Filed: Apr. 14, 2016

(86) PCT No.: PCT/CN2016/079251
§ 371 (c)(1),
(2) Date: Oct. 11, 2017

(87) PCT Pub. No.: WO2016/165626
PCT Pub. Date: Oct. 20, 2016

(65) Prior Publication Data
US 2018/0127412 A1    May 10, 2018

(30) Foreign Application Priority Data
Apr. 15, 2015 (WO) ................ PCT/CN2015/076639

(51) Int. Cl.
| | | |
|---|---|---|
| A61P 35/00 | (2006.01) | |
| C07D 471/04 | (2006.01) | |
| C07D 405/14 | (2006.01) | |
| A61K 31/4355 | (2006.01) | |
| C07C 51/43 | (2006.01) | |
| C07C 57/145 | (2006.01) | |

(52) U.S. Cl.
CPC ............ *C07D 471/04* (2013.01); *A61P 35/00* (2018.01); *C07C 51/43* (2013.01); *C07C 57/145* (2013.01); *C07B 2200/13* (2013.01)

(58) Field of Classification Search
None
See application file for complete search history.

(56) References Cited

U.S. PATENT DOCUMENTS

| | | |
|---|---|---|
| 8,110,687 B2 | 2/2012 | Calderwood et al. |
| 9,273,046 B2 | 3/2016 | Zhou et al. |
| 2010/0184791 A1 | 7/2010 | Lit et al. |
| 2010/0197924 A1 | 8/2010 | Gould et al. |
| 2010/0292205 A1 | 11/2010 | Lefker |
| 2016/0206621 A1 | 7/2016 | Zhou et al. |

FOREIGN PATENT DOCUMENTS

| | | |
|---|---|---|
| WO | WO 2006/065703 | 6/2006 |
| WO | WO 2006/084015 | 8/2006 |
| WO | WO 2007/067444 | 6/2007 |
| WO | WO 2007/136572 | 11/2007 |
| WO | WO 2007/136573 | 11/2007 |
| WO | WO 2008/030448 | 3/2008 |
| WO | WO 2013/097224 | 7/2013 |
| WO | WO 2016/165626 | 10/2016 |

OTHER PUBLICATIONS

International Preliminary Report on Patentability for International Application No. PCT/CN2011/085146, dated Jul. 1, 2014, 6 pages.
International Search Report and Written Opinion for International Application No. PCT/CN2011/085146, dated Sep. 27, 2012, 10 pages.
Supplementary European Search Report for European Application No. 11879096.3, dated Jul. 30, 2015, 4 pages.
European Search Report for European Application No. 16167542.6, dated Nov. 14, 2016, 5 pages.
International Search Report and Written Opinion for International Application No. PCT/CN2016/079251, dated Jul. 21, 2016, 8 pages.
Banales, "Cholangiocarcinoma: current knowledge and future perspectives consensus statement from the European Network for the Study of Cholangiocarcinoma (ENS-CCA)," Nature Reviews Gastroenterology and Hepatology, 2016, 13:261-280.
Blackburn, C. et al., "Discovery and optimization of N-acyl and N-aroylpyrazolines as B-Raf kinase inhibitors," Bioorganic & Medicinal Chemistry Letters 20 (2010) 4795-4799.
Boniface, M. M. et al., "Multidisciplinary management for esophageal and gastric cancer," Cancer Management and Research, 2016:8 39-44.
Cantwell-Dorris, E. R. et al., "BRAF$^{V600E}$: Implications for Carcinogenesis and Molecular Therapy," Mol Cancer Ther., 10(3):385-394 (Mar. 2011).
Damia, G. et al., "Contemporary pre-clinical development of anticancer agents—What are the optimal preclinical models?" European Journal of Cancer, 45 (2009) 2768-2781.
Garson, K. et al., "Models of ovarian cancer—Are we there yet?," Molecular and Cellular Endocrinology 239 (2005) 15-26.
Gerratana, L. et al., "Do platinum salts fit all triple negative breast cancers?" Cancer Treatment Reviews 48 (2016) 34-41.
Gyawali, B. et al., "Chemotherapy in locally advanced head and neck squamous cell carcinoma," Cancer Treatment Reviews, 44 (2016) 10-16.
Howington, J. A. et al., "Treatment of Stage I and II Non-small Cell Lung Cancer," Diagnosis and Management of Lung Cancer, 3rd ed: American College of Chest Physicians Evidence-Based Clinical Practice Guidelines, Chest 2013; 143(5)(Suppl):e278S-e313S.
Jett, J. R. et al., "Treatment of Small Cell Lung Cancer," Diagnosis and Management of Lung Cancer, 3rd ed: American College of Chest Physicians Evidence-Based Clinical Practice Guidelines, Chest 2013; 143(5)(Suppl):e400S-e419S.

(Continued)

*Primary Examiner* — Zinna Northington Davis
(74) *Attorney, Agent, or Firm* — Cooley LLP

(57) ABSTRACT

The invention relates to 5-(((1R,1aS,6bR)-1-(6-(trifluoromethyl)-1H-benzo [d] imidazol-2-yl)-1a,6b-dihydro-1H-cyclopropa [b] benzofuran-5-yl) oxy)-3,4-dihydro-1, 8-naphthyridin-2 (1H)-one (Compound 1) maleate salts, in particular the sesqui-maleate salt and its crystalline forms, methods of preparation, pharmaceutical compositions, and therapeutic uses for treatment of diseases or disorders mediated by BRAF or other kinases.

46 Claims, 22 Drawing Sheets

(56) References Cited

OTHER PUBLICATIONS

Johnson, J. et al., "Relationships between drug activity in NCI preclinical in vitro and in vivo models and early clinical trials," British Journal of Cancer (2001) 84(10):1424-1431.

Kebebew, E. et al., "The Prevalence and Prognostic Value of BRAF Mutation in Thyroid Cancer," Ann. Surg., 2007; 246:466-471.

Khire, U. R. et al., "Omega-carboxypyridyl substituted ureas as Raf kinase inhibitors: SAR of the amide substituent," Bioorganic & Medicinal Chemistry Letters 14 (2004) 783-786.

Labenz, J. et al., "The epidemiology, diagnosis and treatment of Barrett's carcinoma," Dtsch Arztebl Int, 2015; 112:224-234.

Ledford, H., "US cancer institute overhauls cell lines," Nature, Feb. 25, 2016, vol. 530, p. 391.

Lowinger, T. B. et al., "Design and Discovery of Small Molecules Targeting Raf-1 Kinase," Current Pharmaceutical Design, (2002), 8:2269-2278.

Martin-Liberal, J. et al., "New RAF kinase inhibitors in cancer therapy," Expert Opinion on Pharmacotherapy, (2014) 15(9):1235-1245.

Ocana, A. et al., "Preclinical development of molecular targeted agents for cancer," Nat. Rev. Clin. Oncol., (2011) 8:200-209.

Raphael, B. J. et al., "Identifying driver mutations in sequenced cancer genomes: computational approaches to enable precision medicine," Genome Medicine, 2014; 6(5):1-17.

Sale, S. et al., "Models of ovarian cancer metastasis: Murine models," Drug Discovery Today, Disease Models, 2006; 3:149-154.

Sanz-Garcia, E. et al., "Current and advancing treatments for metastatic colorectal cancer," Expert Opinion on Biological Therapy, 16(1):93-110 (2016).

Schober, M. et al., "New Advances in the Treatment of Metastatic Pancreatic Cancer," Digestion, 2015; 92:175-184.

Sharma, S. V. et al., "Cell line-based platforms to evaluate the therapeutic efficacy of candidate anticancer agents," Nature Reviews Cancer (Apr. 2010), 10:241-253.

Simone, J. V., Part XIV Oncology, 154 Introduction, In: Cecil Textbook of Medicine, 20th Edition, vol. 1, Bennett, J. C. (ed.) (1996) pp. 1004-1010.

Socinski, M. A. et al., "Treatment of Stage IV Non-small Cell Lung Cancer," Diagnosis and Management of Lung Cancer, 3rd ed: American College of Chest Physicians Evidence-Based Clinical Practice Guideline, Chest 2013; 143(5)(Suppl):e341S-e368S.

Yoo, S. et al., "New drugs in prostate cancer," Prostate International, 4 (2016) 37-42.

Zambon, A. et al., "Small molecule inhibitors of BRAF in clinical trials," Bioorganic & Medicinal Chemistry Letters, 22 (2012) 789-792.

Zheng, G. et al., "Clinical detection and categorization of uncommon and concomitant mutations involving BRAF," BMC Cancer, 2015; 15:779, 10 pages.

Extended European Search Report for European Application No. 16779601.0, dated Jul. 24, 2018, 6 pages.

Bowker M. J., "A Procedure for Salt Selection and Optimization," Handbook of Pharmaceutical Salts: Properties, Selection, and Use, edited by P. Heinrich Stahl and Camile G. Wermuth. VHCA, Verlag Helvetica Chimica Acta, Zürich, Switzerland, and Wiley-VCH, Weinheim, Germany, pp. 162-173 (Jan. 2002).

Caira, M. R., "Crystalline polymorphism of organic compounds," Topics in Current Chemistry, vol. 198, 1998, pp. 163-208.

Hygroscopicity (Moisture sorption) by DVS

DVS isotherm plot of Crystalline Form A* of Compound 1 Sesqui-Maleate

MALEATE SALTS OF A B-RAF KINASE INHIBITOR, CRYSTALLINE FORMS, METHODS OF PREPARATION, AND USES THEREFORE

CROSS-REFERENCE TO RELATED APPLICATION

This application is a U.S. National Stage Application under 35 U.S.C. § 371 of International Application No. PCT/CN2016/079251, filed on Apr. 14, 2016, and entitled "MALEATE SALTS OF A B-RAF KINASE INHIBITOR, CRYSTALLINE FORMS, METHODS OF PREPARATION, AND USES THEREFORE", which claims the benefit of International Application No. PCT/CN2015/076639, filed Apr. 15, 2015.

FIELD OF THE INVENTION

The present invention relates to maleate salts of a B-RAF kinase inhibitor, i.e., 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one (hereinafter referred to as Compound 1), especially sesqui-maleate of Compound 1, and crystalline forms (polymorphs) of the sesqui-maleates, and methods of preparation, and uses therefore.

BACKGROUND OF THE INVENTION

B-RAF is a kinase that is part of the RAF-MEK-ERK MAPK pathway key to cell proliferation and survival. B-RAF mutations have been discovered in more than 7% of human cancers, including melanoma (43%) (see H. Davies, et al., *Nature,* 417 (2002), 949-54; D. R. English, et al., *Cancer Epidemiol Biomarkers Prev,* 17 (2008), 1774-80; G. V. Long, et al., *Lancet Oncol.,* 13 (2012), 1087-95), thyroid (27%) (see Y. Cohen, *J Natl Cancer Inst,* 95 (2003), 625-7; E. T. Kimura, et al., Cancer Res, 63 (2003), 1454-7), colorectal (14%) (see H. Davies, et al., *Nature,* 417 (2002), 949-54; D. R. English, et al., *Cancer Epidemiol Biomarkers Prev,* 17 (2008), 1774-80; S. Ogino, et al., *Gut,* 58 (2009), 90-6; C. P. Vaughn, *Genes Chromosomes Cancer,* 50 (2011), 307-12), ovarian (15%) (see H. Davies, et al., *Nature,* 417 (2002), 949-54; S. E. Russell, *J Pathol,* 203 (2004), 617-9), and lung (2%) (see M. S. Brose, et al., *Cancer Res,* 62(2002), 6997-7000) cancers. More than 90% of the B-RAF mutations found in melanoma are a substitution of glutamic acid for valine at the 600th amino acid of the B-RAF protein chain (V600E), resulting in constitutive activation.

Clinical experience with B-RAF inhibitors such as vemurafenib and dabrafenib in melanoma patients has proven efficacious, which has validated the concept of targeting tumors dependent on B-RAF and MAPK signaling. Selective inhibition in melanoma patients harboring the B-RAF V600E mutation in their tumors yielded impressive objective response rates and prolongation of progression-free survival. However, the first generation of B-RAF inhibitors, including vemurafenib and dabrafenib, have a number of limitations, for example, 1) development of keratoacanthomas or cutaneous squamous cell carcinoma due to paradoxical increase of MAPK signaling through induction of B-RAF/C-RAF heterodimer in the context of mutated or activated RAS; and 2) limited clinical activity outside of melanoma with B-RAF V600E mutations (e.g., colorectal). Therefore, a second-generation inhibitor that can improve in these areas is highly desirable.

5-(((1R,1aS,6bR)-1-(6-(Trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one (free base, Compound 1) has been disclosed as a second generation B-RAF inhibitor, which has demonstrated potent inhibitory activity against RAF family of serine/threonine kinases. See WO 2013/097224 A1.

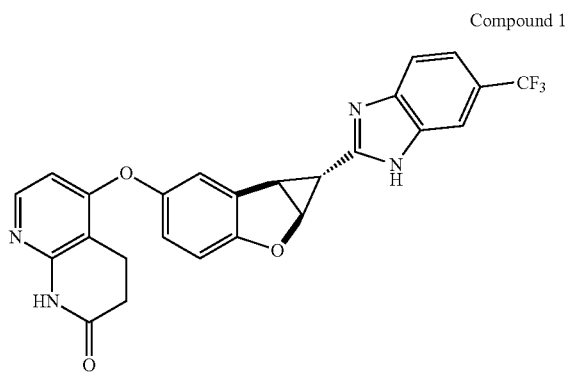

Compound 1

Compound 1 is a molecularly targeted therapeutic agent for the treatment of cancers with aberrations in the RAF-MEK-ERK mitogen-activated protein kinase (MAPK) pathway, including B-RAF mutations and K-RAS/N-RAS mutations, as either monotherapy or in combination with other cancer therapies. However, the relatively poor oral absorption of the free base of Compound 1 makes it unsuitable for drug product development.

It has been also found that the free base of Compound 1 was obtained originally as an amorphous solid based on the XRPD results of FIG. 1, and that the free base of Compound 1 is substantially insoluble in water with <LOQ at 0.001 mg/mL, and is slightly hygroscopic with 2.2% water gain at from 0 to 80% RH.

In addition, the synthesis of Compound 1 was inefficient. Various factors, for example, the requirement of chiral HPLC column for preparing optically pure isomer and the tendency of the free base of Compound 1 in amorphous form hindering the expulsion of impurities from the process, make large scale preparation and purification of Compound 1 a challenge.

Practically, it is difficult to predict with confidence which salts of a particular compound will be stable and suitable for pharmaceutical processing. It is even more difficult to predict whether or not a particular compound will form various crystalline solid-state forms, and to predict the physical properties of these crystalline solid-state forms.

Therefore, there is a great need for some forms of Compound 1 which have much better bioavailability and have chemical and physical stability during formulation and storage of this medication as well as a process suitable for large-scale preparation of Compound 1 with good quality and reproducibility is in great needs.

SUMMARY OF THE INVENTION

The present application discloses an invention to address the foregoing challenges and need by providing stable salts of Compound 1 and crystalline forms thereof.

In the first aspect, provided herewith is a salt of 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one ("Compound 1"), which is selected from hydrochloride, methanesulfonate, 2-hydroxyethanesulfonate, L-tartrate, maleate and oxalate of Compound 1. In one embodiment, the salt is pharmaceutically acceptable. In another embodiment, the salt is in solid-state. In one preferred embodiment, the salt is in a crystalline form. The salts of the present application are in solid form and show different crystalline forms from the free base of Compound 1, indicating they are potential salt candidates. The salts of crystalline form in the present application that has superior physical properties suitable for pharmaceutical formulations and can be manufactured on large commercial scales in high quality and good reproducibility.

Among the crystalline forms of hydrochloride, methanesulfonate, 2-hydroxyethanesulfonate, L-tartrate, maleate and oxalate of Compound 1, the inventors of the present invention unexpectedly discovered that Compound 1 can form maleate salts, in particular, sesqui-maleate salt, in crystalline forms. In particular, it was surprisingly discovered that the maleate salt of Compound 1 (hereinafter sometimes referred to as "Compound 1 maleate salt" or "Compound 1 maleate") can exist in a number of crystalline forms (polymorphs), which are herein referred to as Crystalline Forms A*, A**, A, B, C, D, E, F, G, H, I, J, K, L and M. The Compound 1 maleate salt and its crystalline forms, specifically Crystalline Form A* and A, have superior properties, such as improved solubility and stability, particularly the long-term chemical/physical stability, to those of other salts, which make them suitable candidates for formulation and clinical applications. More particularly, the improved solubility and/or long-term chemical/physical stability of Forms A*, A and the other forms of the Compound 1 maleate salts provides those forms with fast dissolution in vivo and in vitro, and thus increased bioavailability as compared with the free base.

In the second aspect, provided herewith is a compound of Formula (I), which is a maleate salt of 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one:

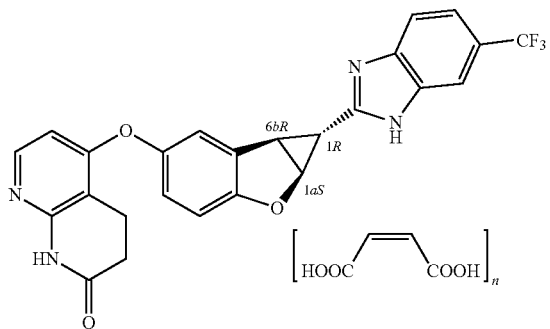

(I)

wherein n is a number from about 0.3 to about 1.5.

In one embodiment, in the compound of Formula (I), n is a number selected from the group consisting of 0.5±0.05, 1.0±0.1, and 1.5±0.2.

In another embodiment, in the compound of Formula (I), n is 0.5, 1.0, or 1.5.

In another preferred embodiment, the compound of Formula (I) is in a crystalline form.

In another preferred embodiment, n is 1.5, and the compound is a crystalline sesqui-maleate salt of 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one of Formula (II):

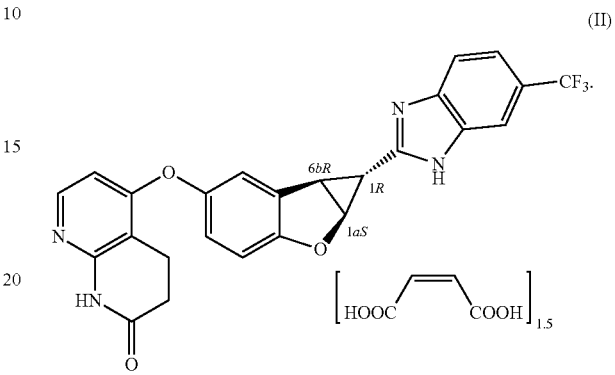

(II)

In one embodiment, the compound of Formula (II) is in Crystalline Form A*, which is characterized by a powder X-ray diffraction pattern comprising seven or more diffraction peaks having 2θ angle values independently selected from the group consisting of: 6.3±0.2, 8.9±0.2, 9.4±0.2, 11.2±0.2, 12.6±0.2, 13.4±0.2, 17.9±0.2, 18.6±0.2, 18.8±0.2, 19.3±0.2, 20.1±0.2, 20.7±0.2, 21.2±0.2, 21.8±0.2, 22.4±0.2, 22.6±0.2, 23.3±0.2, 23.8±0.2, 24.7±0.2, 25.6±0.2, 26.1±0.2, 27.4±0.2, 28.3±0.2, 28.6±0.2, 29.0±0.2, 29.4±0.2, and 30.4±0.2 degrees.

In another embodiment, the compound of Formula (II) is a single crystal in Crystalline Form A**.

In another embodiment, the compound of Formula (II) is in Crystalline Form A, which is characterized by a powder X-ray diffraction pattern comprising three or more diffraction peaks having 2θ angle values independently selected from the group consisting of: 8.3±0.2, 11.2±0.2, 17.9±0.2, 18.4±0.2, 18.6±0.2, 19.3±0.2, 20.8±0.2, and 22.5±0.2 degrees.

In another embodiment, the compound of Formula (I) is in Crystalline Form B, which is characterized by a powder X-ray diffraction pattern comprising three or more diffraction peaks having 2θ angle values independently selected from the group consisting of: 11.1±0.2, 15.8±0.2, 17.7±0.2, 18.4±0.2, 19.6±0.2, 22.3±0.2, 23.1±0.2, and 28.8±0.2 degrees.

In another embodiment, the compound of Formula (I) is in Crystalline Form C, which is characterized by a powder X-ray diffraction pattern comprising three or more diffraction peaks having 2θ angle values independently selected from the group consisting of: 3.1±0.2, 8.8±0.2, 11.2±0.2, 17.8±0.2, 18.5±0.2, 19.3±0.2, 20.1±0.2, 20.7±0.2, 21.9±0.2, and 22.4±0.2 degrees.

In another embodiment, the compound of Formula (I) is in Crystalline Form D, which is characterized by a powder X-ray diffraction pattern comprising three or more diffraction peaks having 2θ angle values independently selected from the group consisting of: 8.9±0.2, 14.9±0.2, 16.7±0.2, 17.8±0.2, 19.9±0.2, 20.4±0.2, 20.9±0.2, and 26.9±0.2 degrees.

In another embodiment, the compound of Formula (I) is in Crystalline Form F, which is characterized by a powder X-ray diffraction pattern comprising three or more diffraction peaks having 2θ angle values independently selected from the group consisting of: 12.9±0.2, 17.0±0.2, 18.5±0.2, 19.4±0.2, 20.5±0.2, 22.5±0.2, and 24.1±0.2 degrees.

In another embodiment, the compound of Formula (I) is in Crystalline Form G, which is characterized by a powder X-ray diffraction pattern comprising seven or more diffraction peaks having 2θ angle values independently selected from the group consisting of: 3.4±0.2, 5.6±0.2, 7.0±0.2, 10.3±0.2, 10.9±0.2, 11.7±0.2, 12.4±0.2, 13.1±0.2, 14.0±0.2, 14.9±0.2, 16.4±0.2, 17.4±0.2, 18.6±0.2, 19.3±0.2, 20.1±0.2, 21.0±0.2, 21.9±0.2, 23.6±0.2, 24.2±0.2, 25.6±0.2, and 26.4±0.2 degrees.

In another embodiment, the compound of Formula (I) is in Crystalline Form H, which is characterized by a powder X-ray diffraction pattern comprising seven or more diffraction peaks having 2θ angle values independently selected from the group consisting of: 6.3±0.2, 9.0±0.2, 10.1±0.2, 11.2±0.2, 12.7±0.2, 14.5±0.2, 16.1±0.2, 16.6±0.2, 17.9±0.2, 18.1±0.2, 18.5±0.2, 19.0±0.2, 20.1±0.2, 21.9±0.2, 22.4±0.2, 23.9±0.2, 25.1±0.2, 26.2±0.2, and 28.7±0.2 degrees.

In another embodiment, the compound of Formula (I) is in Crystalline Form I, which is characterized by a powder X-ray diffraction pattern comprising five or more diffraction peaks having 2θ angle values independently selected from the group consisting of: 3.1±0.2, 5.5±0.2, 6.8±0.2, 10.8±0.2, 11.5±0.2, 13.7±0.2, 16.1±0.2, 16.3±0.2, 17.8±0.2, 19.8±0.2, 21.5±0.2, 23.8±0.2, 24.4±0.2, and 28.3±0.2 degrees.

In another embodiment, the compound of Formula (I) is in Crystalline Form J, which is characterized by a powder X-ray diffraction pattern comprising seven or more diffraction peaks having 2θ angle values independently selected from the group consisting of: 5.5±0.2, 8.2±0.2, 10.9±0.2, 11.3±0.2, 13.6±0.2, 14.8±0.2, 15.8±0.2, 17.4±0.2, 18.0±0.2, 19.1±0.2, 19.8±0.2, 20.0±0.2, 20.4±0.2, 21.1±0.2, 21.9±0.2, 22.6±0.2, 23.4±0.2, 24.1±0.2, 25.0±0.2, 26.1±0.2, 26.9±0.2, 27.3±0.2, 28.4±0.2, 29.1±0.2, 33.1±0.2, and 35.9±0.2 degrees.

In another embodiment, the compound of Formula (I) is in Crystalline Form K, which is characterized by a powder X-ray diffraction pattern comprising seven or more diffraction peaks having 2θ angle values independently selected from the group consisting of: 3.1±0.2, 8.9±0.2, 9.3±0.2, 11.2±0.2, 16.7±0.2, 17.9±0.2, 18.6±0.2, 18.8±0.2, 19.4±0.2, 20.2±0.2, 21.9±0.2, 22.4±0.2, 23.4±0.2, 23.9±0.2, 24.6±0.2, 26.2±0.2, 27.4±0.2, 28.5±0.2, 29.4±0.2, and 30.4±0.2 degrees.

In another embodiment, the compound of Formula (I) is in Crystalline Form L, which is characterized by a powder X-ray diffraction pattern comprising diffraction peaks having the following 2θ angle values: 9.7±0.2 and 14.1±0.2 degrees.

In another embodiment, the compound of Formula (I) is in Crystalline Form M, which is characterized by a powder X-ray diffraction pattern comprising seven or more diffraction peaks having 2θ angle values independently selected from the group consisting of: 5.0±0.2, 9.3±0.2, 11.3±0.2, 14.9±0.2, 15.9±0.2, 17.4±0.2, 18.0±0.2, 18.7±0.2, 19.4±0.2, 20.2±0.2, 22.1±0.2, 23.4±0.2, 24.3±0.2, 25.4±0.2, 26.5±0.2, 27.5±0.2, 28.5±0.2, and 29.3±0.2 degrees.

In some embodiments, in the compound of Formula (I), n is 1, i.e., Compound 1 maleate (1:1). In other embodiment, provided herein is Compound 1 maleate (1:1) Crystalline Form N, which is characterized by a powder X-ray diffraction pattern comprising seven or more diffraction peaks having 2θ angle values independently selected from the group consisting of: 3.30±0.2, 6.61±0.2, 9.88±0.2, 11.73±0.2, 13.14±0.2, 15.23±0.2, 16.56±0.2, 17.94±0.2, 18.72±0.2, 19.34±0.2, 19.93±0.2, 20.76±0.2, 22.04±0.2, 22.95±0.2, 23.86±0.2, 25.19±0.2, 26.61±0.2, 28.36±0.2, 30.13±0.2, 31.36±0.2, 33.49±0.2, and 37.22±0.2.

In another embodiment, the compound of Formula (I) is in a crystalline form substantially characterized by a powder X-ray diffraction pattern selected from the group consisting of FIG. 2, FIG. 16, FIG. 17, FIG. 18, FIG. 19, FIG. 20, FIG. 21, FIG. 22, FIG. 23, FIG. 24, FIG. 25, FIG. 26, FIG. 27, FIG. 28, and FIG. 33.

In some embodiment, Compound 1 maleate (1:1) Crystalline Form N is a chemically stable crystalline form substantially characterized by a powder X-ray diffraction pattern as shown in FIG. 33.

In another aspect, provided herein is a method for preparing a crystalline form of 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one maleate salt of Formula (I), comprising any one of the following procedures:

(a) dissolving free base or a salt other than maleate salt of 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one in a solvent or solvent mixture to form a solution or suspension; mixing the resultant solution or suspension with maleic acid to form a mixture; and precipitating out 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one maleate salt in a target crystalline form;

(b) dissolving or suspending 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one sesqui-maleate salt in a solvent or solvent mixture; and precipitating out 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one maleate salt in a target crystalline form;

(c) storing a crystalline 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one sesqui-maleate salt for an extended period to obtain a target crystalline form;

(d) heating a crystalline or amorphous 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one sesqui-maleate salt to an elevated temperature, and cooling the salt to obtain a target crystalline form; and (e) exposing a crystalline or amorphous 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one maleate salt to a vapor of a solvent to obtain a target crystalline form.

In one embodiment of this aspect, the procedure (a) or (b) further comprises one or more procedures independently selected from heating, filtering to remove undissolved impurities, distilling solvent, adding a counter solvent or solvent mixture, adding crystal seeds, adding precipitation inducing agent(s), cooling, precipitating, and filtering to collect the crystalline product.

In another embodiment of this aspect, the procedure (a) or (b), wherein the solvent or solvent mixture is selected from the group consisting of water, lower alkyl alcohols, ketones, ethers, esters, lower aliphatic carboxylic acids, lower aliphatic nitriles, optionally halogenated aromatic solvents, and combinations thereof.

In another embodiment of this aspect, in the procedure (a) or (b) the solvent is isopropanol, ethanol, methanol, acetone, THF, 1,4-dioxane, acetic acid, acetonitrile, water, or a combination thereof.

In another embodiment of this aspect, in the procedure (a) the free base is an isolated and purified free base, an isolated but unpurified free base, or a crude reaction product containing the free base.

In another embodiment of this aspect, in the procedure (c) the extended period is at least three days, at least one week, or at least two weeks.

In another embodiment of this aspect, in the procedure (d) the elevated temperature is at least 40° C., at least 60° C., at least 80° C., or at least 100° C., but lower than decomposition temperature of the sesqui-maleate salt.

In another embodiment of this aspect, in the procedure (e) the vapor is a vapor of acetic acid.

In another embodiment of this aspect, the method is selected from:

1) the procedure (a) or (b) using isopropanol-water (v/v>60/40) as the solvent to produce Crystalline Form A*;

2) the procedure (a) or (b) using acetone as the solvent to produce Crystalline Form A**;

3) the procedure (a) or (b) using an IPA-water (v:v=4:1) mixture as the solvent to produce Crystalline Form A;

4) the procedure (a) or (b) using 1,4-dioxane as the solvent to produce Crystalline Form B;

5) the procedure (a) or (b) using ethanol as the solvent to produce Crystalline Form C;

6) the procedure (a) or (b) using methanol as the solvent to produce Crystalline Form D;

7) the procedure (a) or (b) using an acetonitrile-water (v:v=1:1) mixture as the solvent to produce Crystalline Form F;

8) the procedure (a) or (b) using an acetic acid-water mixture as the solvent to produce Crystalline Form G;

9) the procedure (a) or (b) using tetrahydrofuran (THF) as the solvent to produce Crystalline Form H;

10) the procedure (a) or (b) using an IPA-water (v:v=3:1) mixture as the solvent to produce Crystalline Form I;

11) the procedure (c) storing Crystalline Form D at ambient temperature for two weeks to produce Crystalline Form K;

12) the procedure (c) storing Crystalline Form J at ambient temperature for two weeks to produce Crystalline Form M;

13) the procedure (d) heating Crystalline Form G to 140° C. and then cooling to ambient temperature to produce Crystalline Form L; and 14) the procedure (e) letting Crystalline Form A interact with acetic acid vapor to produce Crystalline Form J.

In some embodiment, provided herein is a process for preparing a crystalline form of the sesqui-maleate salt of Compound 1 (hereinafter sometimes referred to as "Compound 1 sesqui-maleate salt" or "Compound 1 sesqui-maleate") comprising mixing at a temperature below the reflux temperature, for example, mixing at about 50° C. a mixture of Compound 1 and maleic acid in a mixed solvent of i-PrOH and H$_2$O, or mixing at a temperature below the reflux temperature, for example, mixing at about 50° C. Compound 1 with a mixture or a suspension or a solution of maleic acid in a mixed solvent of i-PrOH and H$_2$O, or mixing at a temperature below the reflux temperature, for example, mixing at about 50° C. a mixture or a suspension or a solution of Compound 1 in a mixed solvent of i-PrOH and H$_2$O with maleic acid, wherein the amount of i-PrOH is greater than 40 vol % in terms of the total volume of i-PrOH and water, preferably 60 vol %, and more preferably 90 vol %. In some preferred embodiment, the above-mentioned mixed solvent is replaced with i-PrOH. In other embodiment, the process further comprises adding some crystal seeds into the resultant mixture after cooling to room temperature, and then letting the mixture stand for a certain duration, such as 12 hours, 24 hours, 2, 3, or 4 days or 1 week, 2 weeks.

In some embodiment, provided herein is a process for preparing a crystalline form of Compound 1 maleate (1:1) comprising mixing a crystalline form of Compound 1 sesqui-maleate with methanol. In some embodiment, the above mixing is performed with stirring. In some embodiment, the crystalline form of Compound 1 maleate (1:1) is Form N as disclosed herein. In some embodiment, the crystalline form of Compound 1 maleate is any one selected from the group consisting of Crystalline Forms A*, A**, A, B, C, D, F, G, H, I, J, K, L and M. In some embodiment, the above mixing is performed for about one day, or 2 days, or 3 days, or 4 days, 5 days, or 6 days or one week, or 2 weeks. This conversion of Compound 1 Sesqui-Maleate Salt (1:1.5) into the Maleate Salt (1:1) provides a cost-effective process for making and/or further purifying the active pharmaceutical ingredient Compound 1 with very simple procedure, for example, by simply stirring Compound 1 Sesqui-Maleate, e.g., any one of Crystalline Form A*, A** and A in methanol at room temperature or elevated temperature. This conversion has been found to give rise to a reduced crystalline particle size for the resultant crystalline substance (i.e., Compound 1 maleate (1:1) Crystalline Form), which may, in turn, increase the dissolution rate for drug product and further increase the chemical purity of the drug product. In this regard, the conversion has been expected to further simplify the drug product manufacture process, for example, without using micronization and roller compaction process.

In another aspect, provided herein is a pharmaceutical composition comprising a compound of Formula (I) or Formula (II) according to any of the embodiments described herein and a pharmaceutically acceptable carrier.

In one embodiment, the pharmaceutical composition is suitable for oral administration.

In another embodiment, the pharmaceutical composition is in the form of tablet or capsule.

In another embodiment, the unit dosage of the tablet or capsule is 5-80 mg.

In another embodiment, the weight percentage of the compound in the pharmaceutical composition is 1-99%.

In another aspect, provided herein is a method of treating or preventing a disease or disorder in a subject, such as human being, comprising administering to said subject a therapeutically effective amount of a compound of Formula (I) or Formula (II) according to any of the embodiments described herein or a pharmaceutical composition comprising a compound of Formula (I) or Formula (II).

In one embodiment, the disease or disorder is a cancer selected from the group consisting of brain cancer, lung cancer, kidney cancer, bone cancer, liver cancer, bladder cancer, breast, head and neck cancer, ovarian cancer, melanoma, skin cancer, adrenal cancer, cervical cancer, colorectal cancer, lymphoma, or thyroid tumors and their complications.

In another embodiment, the disease is selected from the group consisting of BRAF, NRAS and KRAS mutant brain cancer, lung cancer, kidney cancer, bone cancer, liver cancer, bladder cancer, breast, head and neck cancer, ovarian cancer, melanoma, skin cancer, adrenal cancer, cervical cancer, colorectal cancer, lymphoma, or thyroid tumors and their complications.

In another embodiment, the administered dosage of the compound is 1-100 mg/day, and the administration frequency is one to three times a day.

In another embodiment, the administered dosage of the compound is 5-50 mg/day, and the administration frequency is one to three times a day.

In another embodiment, the administered dosage of the compound is 10-40 mg/day, and the administration frequency is one time a day.

In another embodiment, the compound is 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one maleate in a crystalline form selected from the group consisting of Crystalline Forms A*, A**, A, B, C, D, F, G, H, I, J, K, L, M and N.

In another aspect, provided herein is use of a compound of Formula (I) or Formula (II) according to any of the embodiments described herein in the manufacture of a medicament for treatment of a disease or disorder associated with BRAF, NRAS and KRAS activities.

In a preferred embodiment, the disease is a cancer.

In another preferred embodiment, the compound is 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one maleate in a crystalline form selected from the group consisting of Crystalline Forms A*, A**, A, B, C, D, F, G, H, I, J, K, L, M and N. These and other aspects of the present invention will be better appreciated in view of the following drawings, detailed description, and claims.

BRIEF DESCRIPTIONS OF THE DRAWINGS

DETAILED DESCRIPTION OF THE INVENTION

In the course of preparing the salts of the present invention, many salt-forming agents commonly used in the pharmaceutical industry were investigated. In particular, the salt-forming agents investigated in the present invention include the following 25 acids or salt-forming agents selected from the group consisting of hydrochloric acid, sulfuric acid, phosphoric acid, methanesulfonic acid, 2-hydroxyethanesulfonic acid, benzenesulfonic acid, glycolic acid, l-lactic acid, fumaric acid, l-tartaric acid, citric acid, l-malic acid, succinic acid, hippuric acid, maleic acid, adipic acid, benzoic acid, gentisic acid, malonic acid, ethanedisulfonic acid, toluenesulfonic acid, oxalic acid, nicotinic acid, nicotinamide, and saccharin.

Figure 3:
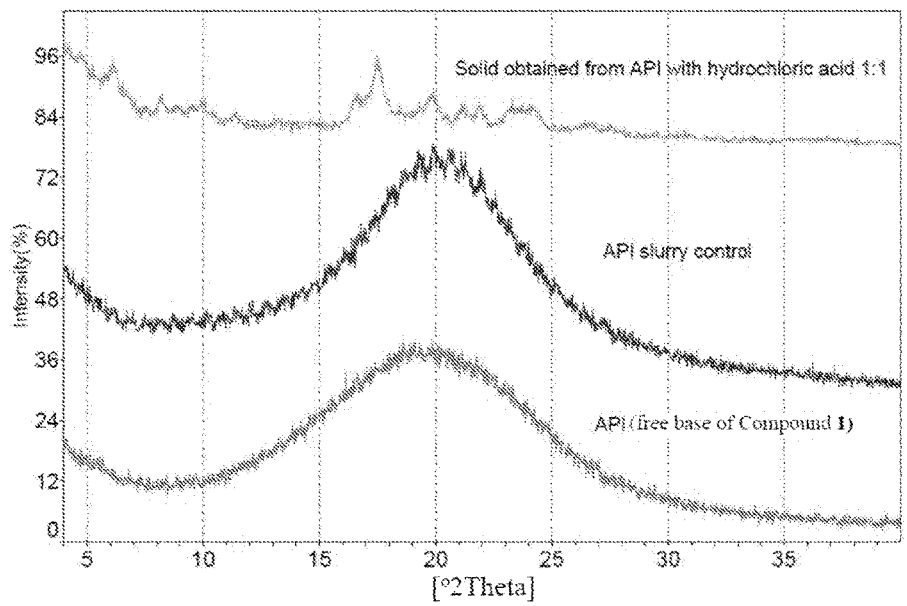
FIG. 3 shows an X-ray diffraction pattern of Compound 1 hydrochloride salt (1:1).
Figure 4:
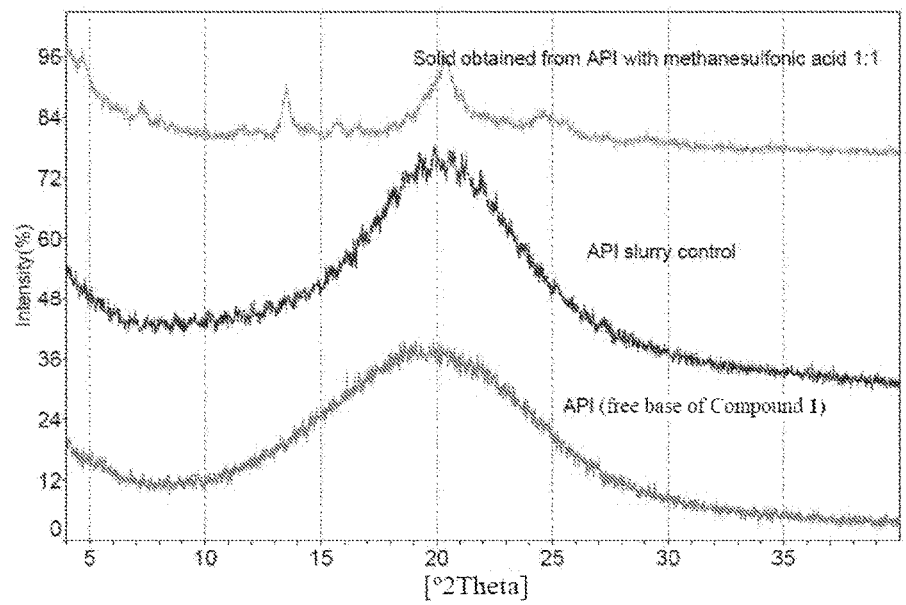
FIG. 4 shows an X-ray diffraction pattern of Compound 1 methanesulfonate salt (1:1).
Figure 5:
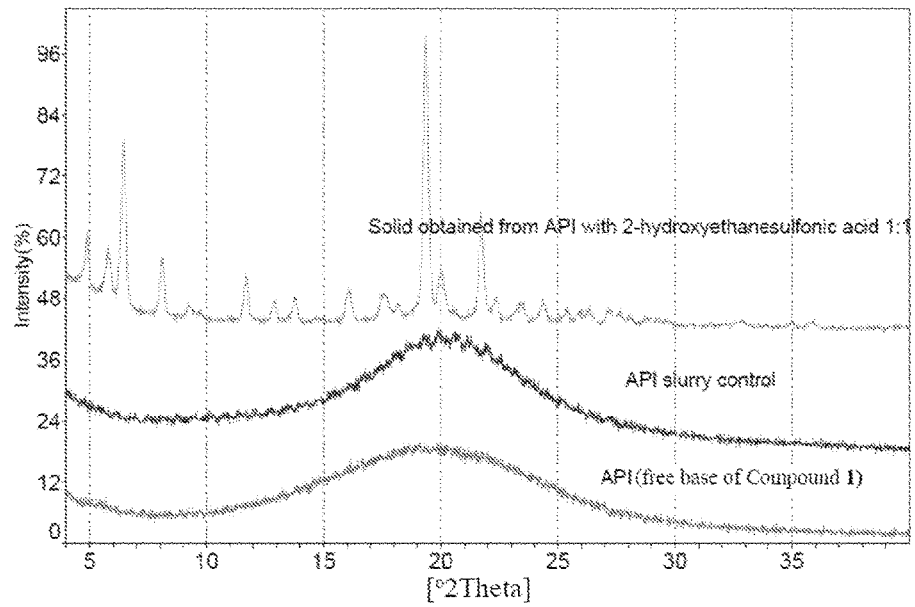
FIG. 5 shows an X-ray diffraction pattern of Compound 1 2-hydroxyethanesulfonate salt (1:1).
Figure 6:
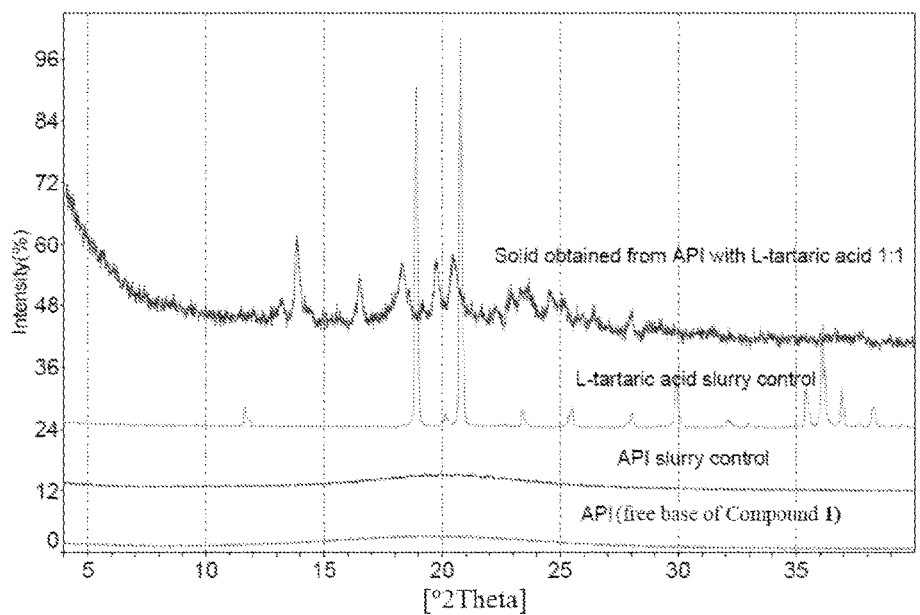
FIG. 6 shows an X-ray diffraction pattern of Compound 1 L-tartrate salt (1:1)
Figure 7:
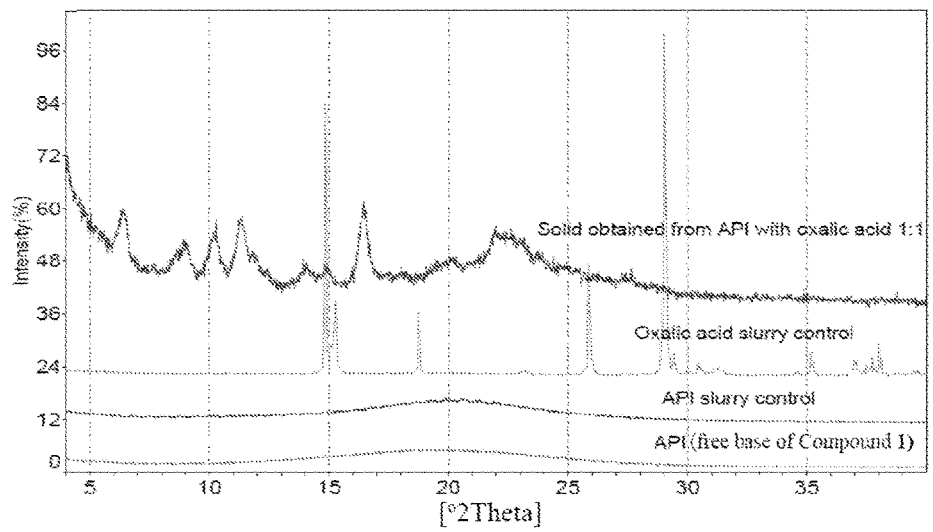
FIG. 7 shows an X-ray diffraction pattern of Compound 1 oxalate (1:1).

However, the reaction of Compound 1 with only six salts showed the formation of salts. In particular, solid forms of salts of Compound 1 with six acids including hydrochloric acid (FIG. 3), methanesulfonic acid (FIG. 4), 2-hydroxyethanesulfonic acid (FIG. 5), L-tartaric acid (FIG. 6), maleic acid (FIG. 2, FIG. 17, etc.) and oxalic acid (FIG. 7) showed different crystalline form from free base, API control and solid acid control. In contrast to the above six crystalline salts of the present application, the other salts failed to crystallize.

Figure 1:
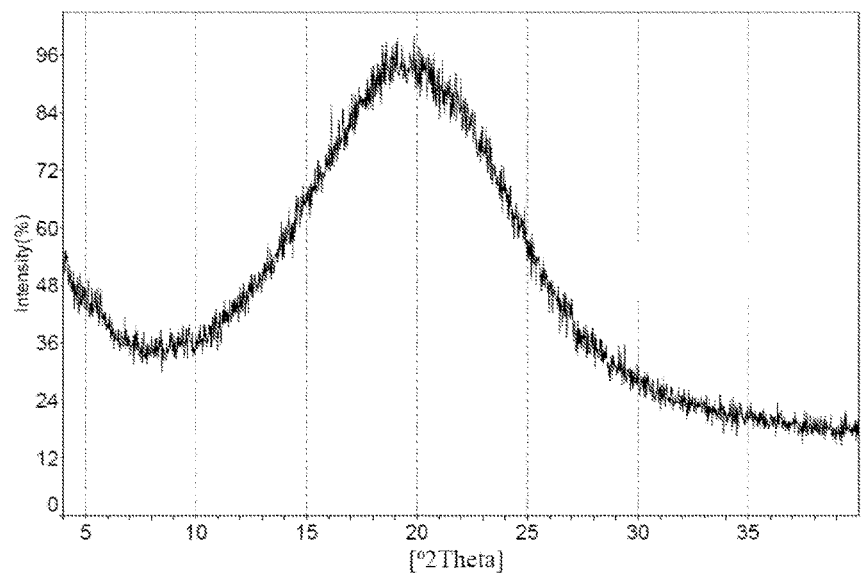
FIG. 1 shows an X-ray diffraction pattern of Compound 1 in amorphous form.
Figure 2:
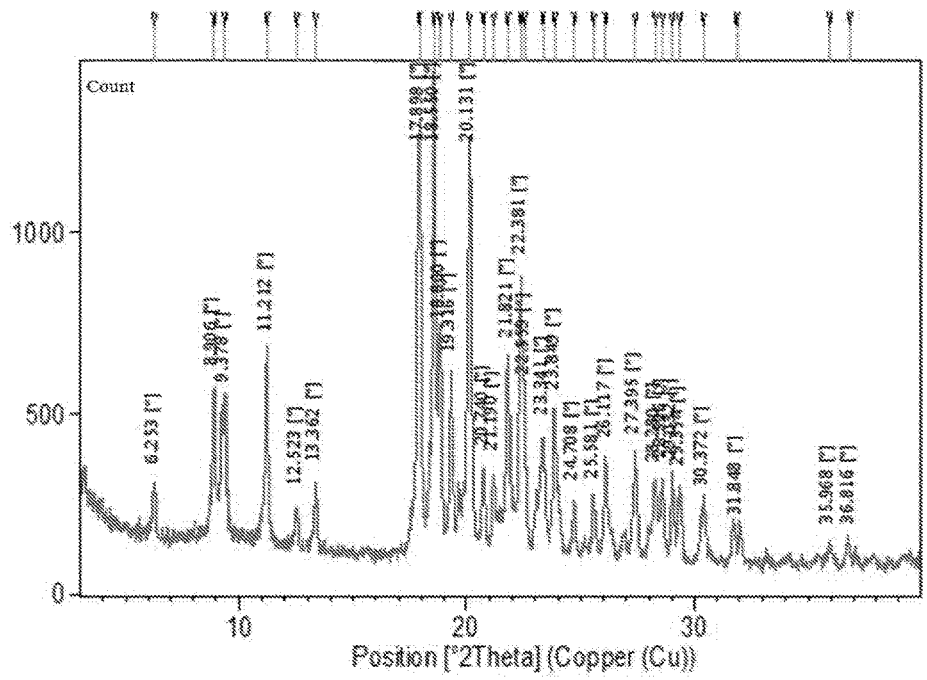
FIG. 2 shows an X-ray diffraction pattern of Crystalline Form A* of Compound 1 Sesqui-Maleate (crystallization from isopropanol/water).

In one aspect, provided herein is Compound 1 Sesqui-Maleate Salt, which is prepared by the process disclosed herein in large quantities. As shown in FIG. 2, Compound 1 Sesqui-Maleate Salt is in a crystalline form (refered herein as Crystalline Form A*) and its X-ray powder diffraction spectra typically have the following peak diffraction angles (where "spacing" is shown as the "d-value" in FIG. 2):

TABLE 1

X-ray Diffraction Pattern of Compound 1 Sesqui-Maleate (Crystalline Form A*)

| Peak# | Diffraction angle (2-theta) | Spacing | Relative intensity |
|---|---|---|---|
| 1 | 6.253 | 14.13519 | 10.0 |
| 2 | 8.906 | 9.92940 | 30.9 |
| 3 | 9.378 | 9.43099 | 28.13 |
| 4 | 11.212 | 7.89173 | 38.55 |
| 5 | 12.5523 | 7.06862 | 8.177 |
| 6 | 13.362 | 6.62652 | 13.20 |
| 7 | 17.898 | 4.95609 | 88.46 |
| 8 | 18.550 | 4.78320 | 100.0 |
| 9 | 18.800 | 4.72011 | 43.37 |
| 10 | 19.316 | 4.59525 | 36.49 |
| 11 | 20.131 | 4.41102 | 83.24 |
| 12 | 20.740 | 4.28292 | 17.94 |
| 13 | 21.190 | 4.19287 | 16.90 |
| 14 | 21.821 | 4.07307 | 36.93 |
| 15 | 22.381 | 3.97242 | 56.88 |
| 16 | 22.559 | 3.94149 | 32.65 |
| 17 | 23.341 | 3.81112 | 24.44 |
| 18 | 23.849 | 3.73111 | 29.73 |
| 19 | 24.708 | 3.60331 | 11.49 |
| 20 | 25.581 | 3.48226 | 11.77 |
| 21 | 26.117 | 3.41211 | 20.07 |
| 22 | 27.395 | 3.25570 | 21.16 |
| 23 | 28.280 | 3.15580 | 15.24 |
| 24 | 28.596 | 3.12169 | 16.38 |
| 25 | 29.032 | 3.07578 | 16.13 |
| 26 | 29.354 | 3.04276 | 14.76 |
| 27 | 30.372 | 2.94304 | 10.81 |

Crystalline Form A* of Compound 1 Sesqui-Maleate is a rather stable crystalline form. After micronization to become well distributed fine particles having an average particle size (D90) of approximately 1-10 microns, it can be readily formulated into drug product for clinical uses.

In another embodiment, provided herein is Single Crystal Form A of Compound 1 Sesqui-Maleate. The structure of Crystalline Form A of Compound 1 Sesqui-Maleate was determined using a set of diffraction data collected from a single crystal grown by slow cooling in acetone. Crystal data and structure refinement are listed in Table 2.

TABLE 2

Single Crystal Data and Structure Refinement of Compound 1 Sesqui-Maleate (Crystalline Form A**)

| | | |
|---|---|---|
| Empirical formula | $C_{25}H_{17}F_3N_4O_3 \cdot 1.5 C_4H_4O_4$ | — |
| Formula weight | 652.5 | |
| Temperature | 173(2) K | — |
| Wavelength | 1.54178 Å | — |
| Crystal system, space group | Monoclinic | C2 |
| Unit cell dimensions | a = 19.7026(5) Å | alpha = 90.00 deg. |
| | b = 5.1350(2) Å | beta = 93.692(2) deg. |
| | c = 28.4299(8) Å | gamma = 90.00 deg. |
| Volume | 2870.36(16) Å$^3$ | — |
| Z, Calculated density | 4 | 1.505 Mg/m$^3$ |
| Absorption coefficient | 1.076 mm$^{-1}$ | — |
| F(000) | 1336 | |
| Crystal size | 0.09 × 0.08 × 0.05 mm | — |
| Theta range for data collection | 4.50 to 66.10 deg. | |
| Limiting indices | −20 <= h <= 23, | |
| | −6 <= k <= 5, | — |
| | −30 <= l <= 32 | |
| Reflections collected/unique | 7195/3684 [R(inf) = 0.0272] | — |
| Completeness | 92.6% | |
| Refinement method | Full matrix least squares on F$^3$ | — |
| Data/restraints/parameters | 3684/2/436 | — |

TABLE 2-continued

Single Crystal Data and Structure Refinement of Compound 1 Sesqui-Maleate (Crystalline Form A**)

| | | |
|---|---|---|
| Goodness-of-fit on $F^2$ | 1.033 | — |
| Final R indices [I > 2sigma(I)] | R1 = 0.0818 | wR2 = 0.2276 |
| Absolute structure parameter | 0.1(5) | |
| Largest diff. peak and hole | 0.535 and −0.411 e · $A^{-3}$ | — |

Figure 13:
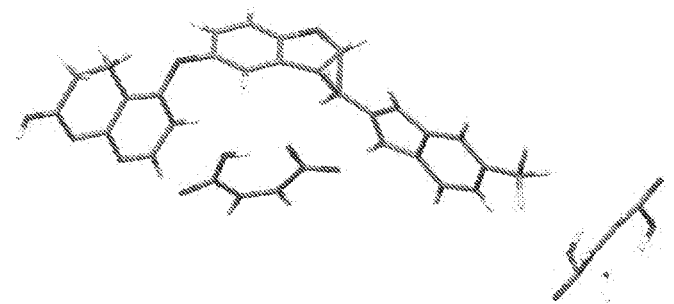
FIG. 13 shows the absolute structure of Single Crystalline Form A** of Compound 1 Sesqui-Maleate (single crystals obtained by crystallization from acetone).
Figure 14:
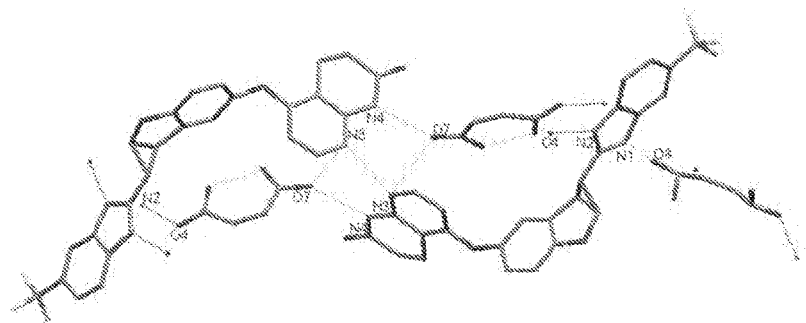
FIG. 14 illustrates hydrogen bonds of Single Crystalline Form A** of Compound 1 Sesqui-Maleate.
Figure 15:
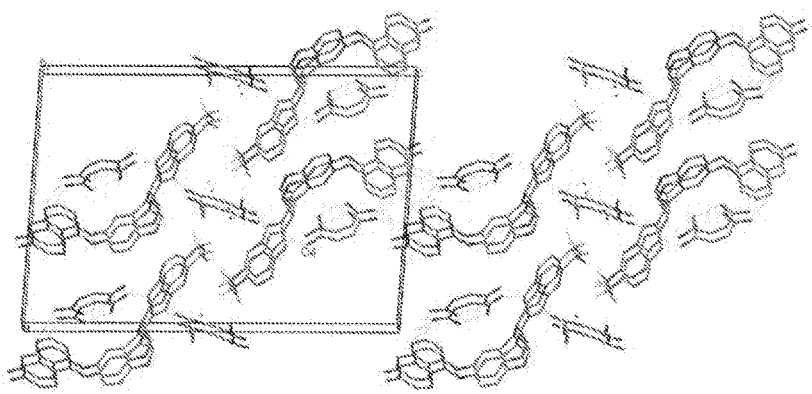
FIG. 15 shows a Crystal Packing of Single Crystalline Form A** of Compound 1 Sesqui-Maleate.
Figure 16:
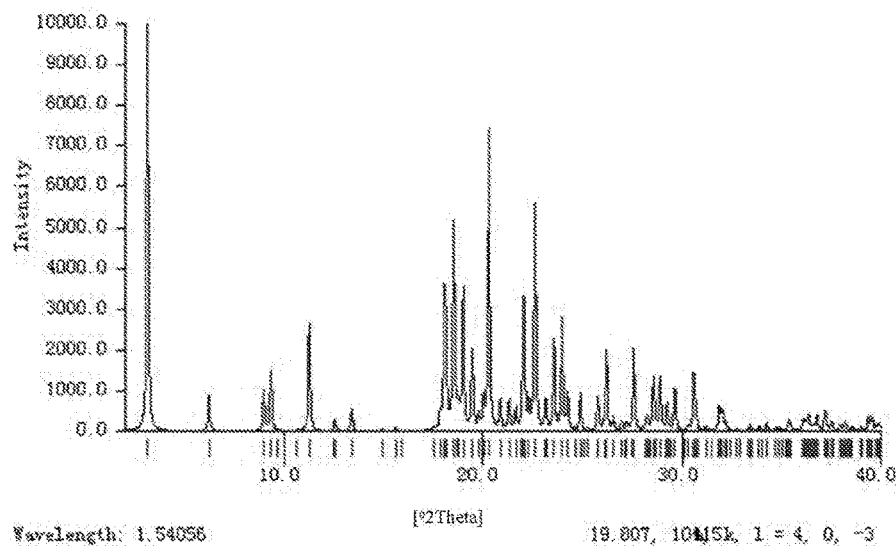
FIG. 16 shows a theoretical XRPD pattern of Single Crystalline Form A** of Compound 1 Sesqui-Maleate calculated using the MERCURY software.

The single crystal structure of Compound 1 maleate, shown in FIG. 13, confirms a sesqui-maleate salt, in which the imidazole nitrogen atom of the free base molecule is protonated. The absolute configurations of C1(S), C2(R) and C3(R) were determined with high probability as indicated by the absolute structure parameter of 0.1(5). The hydrogen bonding interactions are demonstrated in FIG. 14. The structure demonstrates a two-dimensional structure in the be plane. The free base molecules of Compound 1 and maleate anions are linked by inter-molecular interaction (N3 . . . N3 2.797 Å) and hydrogen bond (N2-H2 . . . O4 2.760 Å) along b axis. The tape structures are then linked by maleate anions via intermolecular interactions (N3 . . . O7 3.008 Å and N4 . . . O7 2.715 Å) and hydrogen bond (N1-H1 . . . O8 2.659 Å) along c axis to form a two-dimensional structure. Crystal packing of Compound 1 Sesqui-Maleate salt is shown in FIG. 15. Theoretical PXRD pattern of Single Crystalline Form A of Compound 1 Sesqui-Maleate calculated using the MERCURY software is shown in FIG. 16**.

Figure 17:
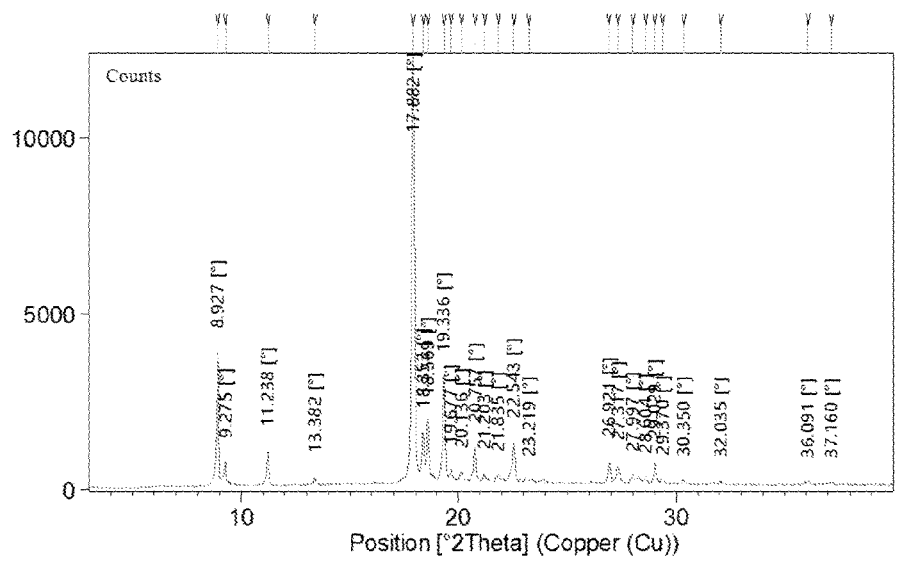
FIG. 17 shows an X-ray diffraction pattern of Crystalline Form A of Compound 1 Sesqui-Maleate (obtained by recrystallization from isopropanol/water).

In another embodiment, provided herein is Crystalline Form A of Compound 1 Sesqui-Maleate. As shown in FIG. 17, Crystalline Form A's X-ray powder diffraction spectra typically have the following peak diffraction angles (where "spacing" is shown as the "d-value" in FIG. 17):

TABLE 3

X-ray Diffraction Pattern of Compound 1 Sesqui-Maleate (Crystalline Form A)

| Peak# | Diffraction angle (2 theta) | Spacing | Relative intensity |
|---|---|---|---|
| 1 | 8.27 | 9.90600 | 30.76 |
| 2 | 11.238 | 7.87344 | 7.95 |
| 3 | 17.881 | 4.96051 | 100 |
| 4 | 18.353 | 4.83408 | 11.84 |
| 5 | 18.569 | 4.77847 | 14.65 |
| 6 | 19.336 | 4.59064 | 24.76 |
| 7 | 20.757 | 4.27949 | 8.36 |
| 8 | 22.543 | 3.94417 | 9.52 |

Figure 18:
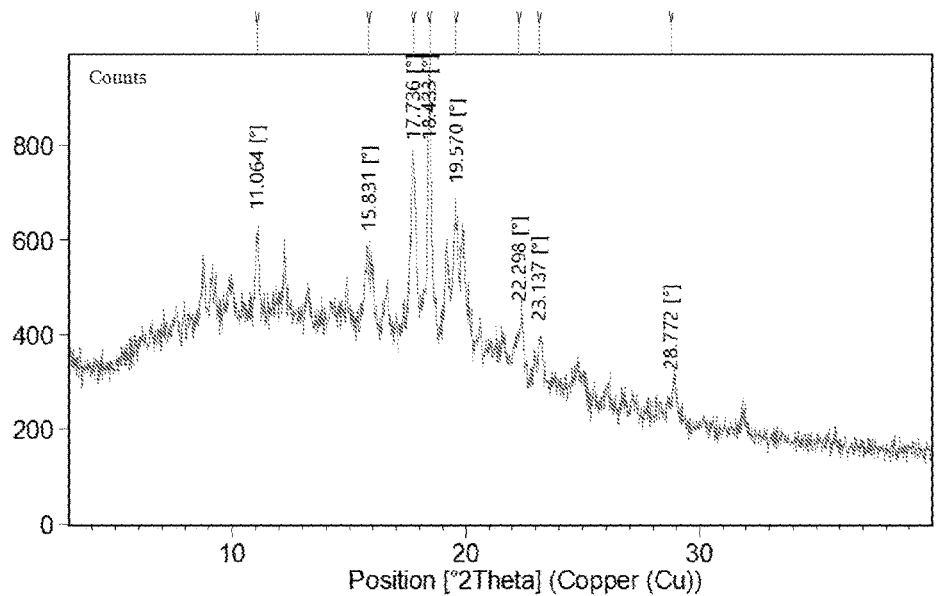
FIG. 18 shows an X-ray diffraction pattern of Crystalline Form B of Compound 1 maleate.

In another embodiment, provided herein is Crystalline Form B of Compound 1 maleate. As shown in FIG. 18, Crystalline Form B's X-ray powder diffraction spectra typically have the following peak diffraction angles (where "spacing" is shown as the "d-value" in FIG. 18):

TABLE 4

X-ray Diffraction Pattern of Compound 1 maleate (Crystalline Form B)

| Peak# | Diffraction angle (2 theta) | Spacing | Relative intensity |
|---|---|---|---|
| 1 | 11.064 | 7.99711 | 25.70 |
| 2 | 15.830 | 5.59824 | 23.75 |
| 3 | 17.735 | 5.00106 | 60.43 |
| 4 | 18.433 | 4.81337 | 100.00 |
| 5 | 19.569 | 4.53629 | 49.28 |
| 6 | 22.298 | 3.98695 | 15.61 |
| 7 | 23.136 | 3.84440 | 11.05 |
| 8 | 28.772 | 3.10295 | 8.09 |

Figure 19:
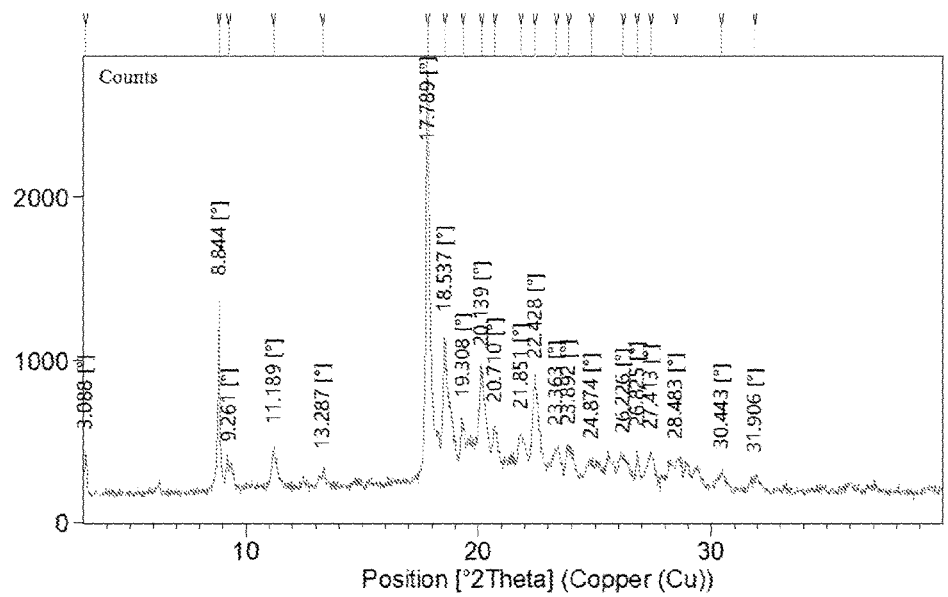
FIG. 19 shows an X-ray diffraction pattern of Crystalline Form C of Compound 1 maleate.

In another embodiment, provided herein is Crystalline Form C of Compound 1 maleate. As shown in FIG. 19, Crystalline Form C's X-ray powder diffraction spectra typically have the following peak diffraction angles (where "spacing" is shown as the "d-value" in FIG. 19):

TABLE 5

X-ray Diffraction Pattern of Compound 1 maleate (Crystalline Form C)

| Peak# | Diffraction angle (2 theta) | Spacing | Relative intensity |
|---|---|---|---|
| 1 | 3.088 | 28.60902 | 9.98 |
| 2 | 8.848 | 9.99908 | 46.62 |
| 3 | 11.189 | 7.90827 | 9.76 |
| 4 | 17.789 | 4.98615 | 100 |
| 5 | 18.537 | 4.78670 | 36.03 |
| 6 | 19.308 | 4.59714 | 14.97 |
| 7 | 20.139 | 4.40940 | 27.63 |
| 8 | 20.710 | 4.28897 | 14.07 |
| 9 | 21.851 | 4.06750 | 12.59 |
| 10 | 22.427 | 3.96427 | 24.96 |

Figure 20:
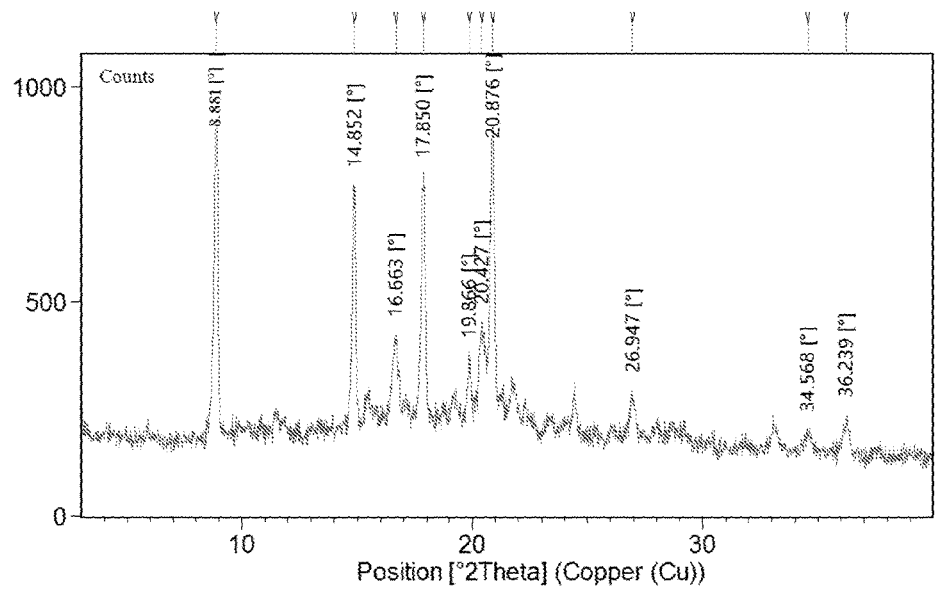
FIG. 20 shows an X-ray diffraction pattern of Crystalline Form D of Compound 1 maleate.

In another embodiment, provided herein is Crystalline Form D of Compound 1 maleate. As shown in FIG. 20, Crystalline Form D's X-ray powder diffraction spectra typically have the following peak diffraction angles (where "spacing" is shown as the "d-value" in FIG. 20):

TABLE 6

X-ray Diffraction Pattern of Compound 1 maleate (Crystalline Form D)

| Peak# | Diffraction angle (2 theta) | Spacing | Relative intensity |
|---|---|---|---|
| 1 | 8.8814 | 9.95688 | 100 |
| 2 | 14.852 | 5.96478 | 62.23 |
| 3 | 16.662 | 5.32061 | 21.84 |
| 4 | 17.849 | 4.96938 | 63.17 |
| 5 | 19.866 | 4.46927 | 14.65 |
| 6 | 20.427 | 4.34779 | 23.50 |
| 7 | 20.875 | 4.25534 | 77.17 |
| 8 | 26.946 | 3.30884 | 10.36 |

Figure 21:
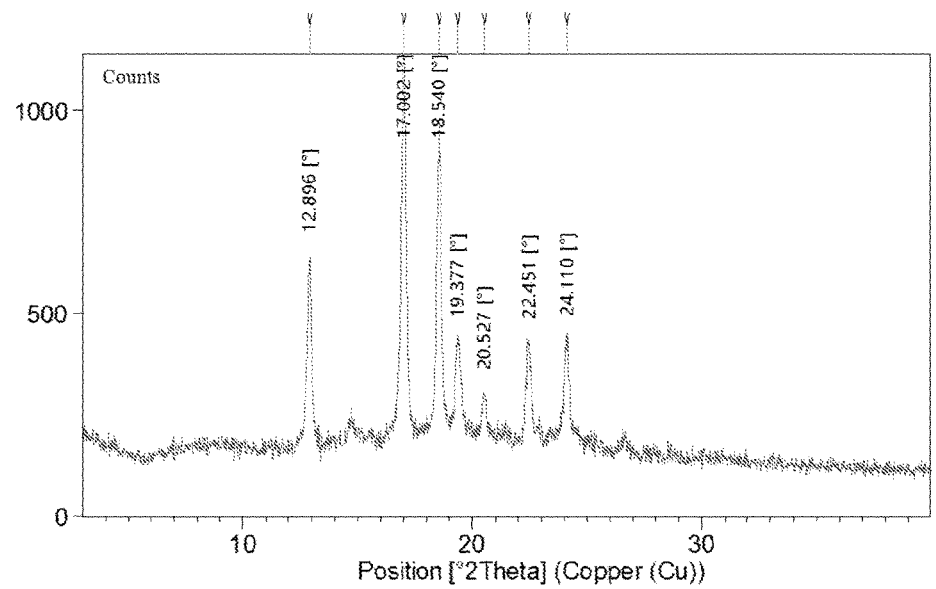
FIG. 21 shows an X-ray diffraction pattern of Crystalline Form F of Compound 1 maleate.

In another embodiment, provided herein is Crystalline Form F of Compound 1 maleate. As shown in FIG. 21, Crystalline Form F's X-ray powder diffraction spectra typically have the following peak diffraction angles (where "spacing" is shown as the "d-value" in FIG. 21):

TABLE 7

X-ray Diffraction Pattern of Compound 1 maleate (Crystalline Form F)

| Peak# | Diffraction angle (2 theta) | Spacing | Relative intensity |
|---|---|---|---|
| 1 | 12.8950 | 6.86490 | 48.90 |
| 2 | 17.002 | 5.21500 | 100.00 |
| 3 | 18.539 | 4.78590 | 80.53 |
| 4 | 19.376 | 4.58097 | 25.72 |
| 5 | 20.526 | 4.32695 | 12.38 |

TABLE 7-continued

X-ray Diffraction Pattern of Compound
1 maleate (Crystalline Form F)

| Peak# | Diffraction angle (2 theta) | Spacing | Relative intensity |
|---|---|---|---|
| 6 | 22.450 | 3.96024 | 26.20 |
| 7 | 24.109 | 3.69134 | 27.52 |

Figure 22:
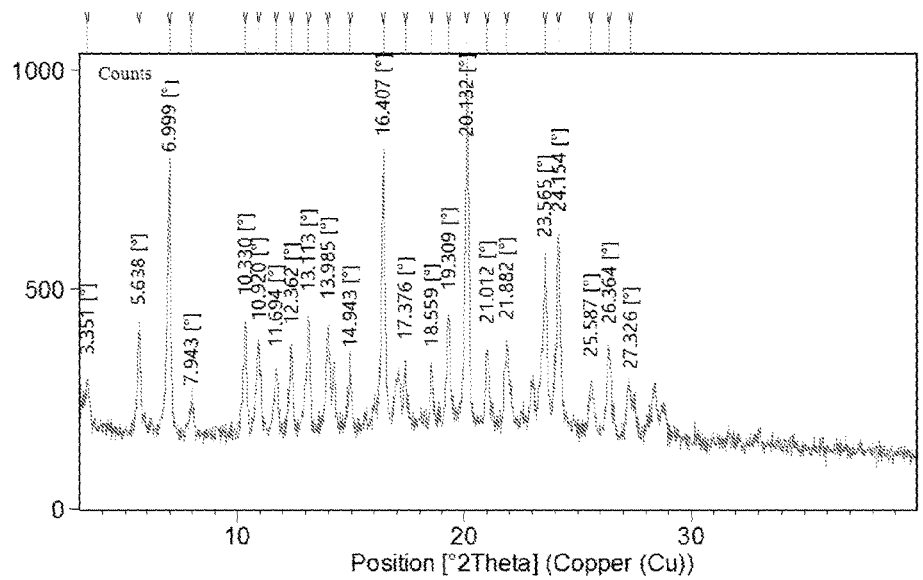
FIG. 22 shows an X-ray diffraction pattern of Crystalline Form G of Compound 1 maleate.

In another embodiment, provided herein is Crystalline Form G of Compound 1 maleate. As shown in FIG. 22, Crystalline Form G's X-ray powder diffraction spectra typically have the following peak diffraction angles (where "spacing" is shown as the "d-value" in FIG. 22):

TABLE 8

X-ray Diffraction Pattern of Compound
1 maleate (Crystalline Form G)

| Peak# | Diffraction angle (2 theta) | Spacing | Relative intensity |
|---|---|---|---|
| 1 | 3.351422 | 26.36357 | 14.43 |
| 2 | 5.638473 | 15.67420 | 27.54 |
| 3 | 6.998775 | 12.63047 | 67.95 |
| 4 | 10.329730 | 8.56388 | 29.94 |
| 5 | 10.919920 | 8.10232 | 23.42 |
| 6 | 11.694360 | 7.56744 | 16.36 |
| 7 | 12.362260 | 7.16005 | 22.10 |
| 8 | 13.112730 | 6.75191 | 30.97 |
| 9 | 13.984910 | 6.33272 | 28.84 |
| 10 | 14.943380 | 5.92863 | 16.07 |
| 11 | 16.407270 | 5.40281 | 74.55 |
| 12 | 17.376000 | 5.10373 | 18.05 |
| 13 | 18.558810 | 4.78103 | 16.17 |
| 14 | 19.308660 | 4.59702 | 31.06 |
| 15 | 20.132270 | 4.41078 | 100.00 |
| 16 | 21.012040 | 4.22805 | 22.15 |
| 17 | 21.881810 | 4.06192 | 23.11 |
| 18 | 23.564930 | 3.77547 | 44.67 |
| 19 | 24.154400 | 3.68465 | 51.53 |
| 20 | 25.587090 | 3.48149 | 13.17 |
| 21 | 26.364010 | 3.38063 | 21.61 |

Figure 23:
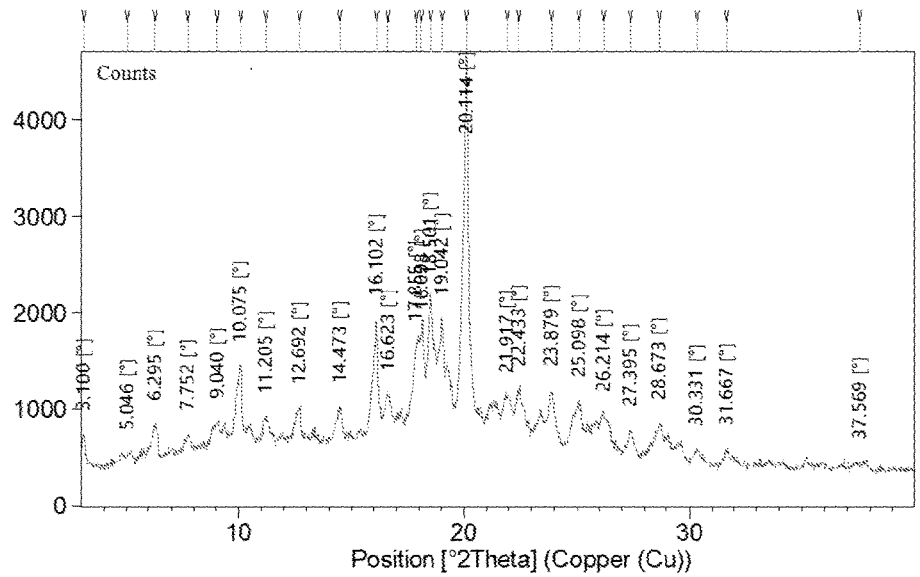
FIG. 23 shows an X-ray diffraction pattern of Crystalline Form H of Compound 1 maleate.

In another embodiment, provided herein is Crystalline Form H of Compound 1 maleate. As shown in FIG. 23, Crystalline Form H's X-ray powder diffraction spectra typically have the following peak diffraction angles (where "spacing" is shown as the "d-value" in FIG. 23):

TABLE 9

X-ray Diffraction Pattern of Compound
1 maleate (Crystalline Form H)

| Peak# | Diffraction angle (2 theta) | Spacing | Relative intensity |
|---|---|---|---|
| 1 | 6.294908 | 14.04108 | 9.99 |
| 2 | 9.040457 | 9.78209 | 10.48 |
| 3 | 10.074560 | 8.78021 | 24.60 |
| 4 | 11.204790 | 7.89696 | 11.80 |
| 5 | 12.692280 | 6.97462 | 14.26 |
| 6 | 14.473290 | 6.12011 | 14.35 |
| 7 | 16.101530 | 5.50471 | 36.24 |
| 8 | 16.622550 | 5.33332 | 17.30 |
| 9 | 17.855220 | 4.96781 | 29.67 |
| 10 | 18.097650 | 4.90181 | 32.61 |
| 11 | 18.501470 | 4.79572 | 41.68 |
| 12 | 19.042360 | 4.66070 | 36.42 |
| 13 | 20.114010 | 4.41474 | 100.00 |
| 14 | 21.917240 | 4.05543 | 16.94 |
| 15 | 22.433180 | 3.96331 | 18.58 |
| 16 | 23.879340 | 3.72646 | 18.50 |
| 17 | 25.098100 | 3.54820 | 15.92 |
| 18 | 26.213960 | 3.39964 | 12.23 |
| 19 | 28.673350 | 3.11340 | 10.18 |

Figure 24:
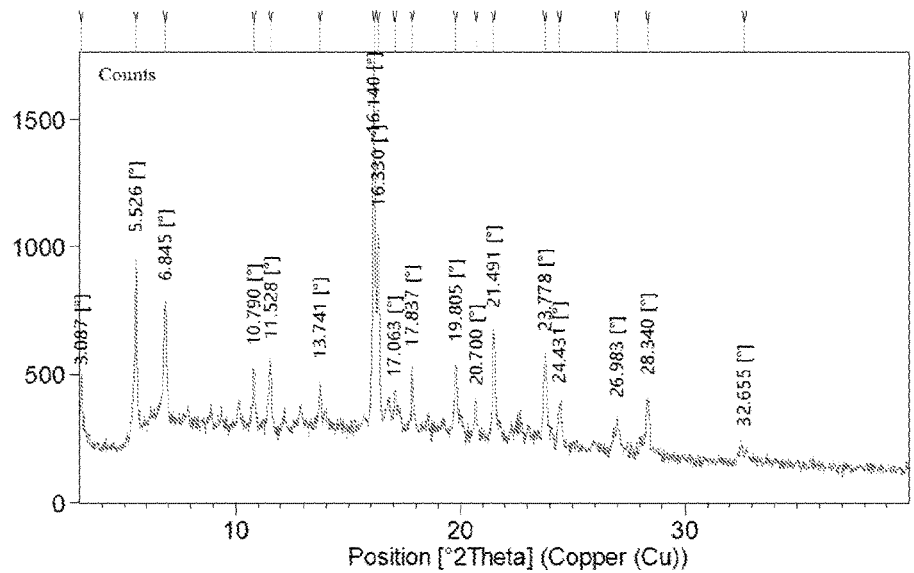
FIG. 24 shows an X-ray diffraction pattern of Crystalline Form I of Compound 1 maleate.

In another embodiment, provided herein is Crystalline Form I of Compound 1 maleate. As shown in FIG. 24, Crystalline Form I's X-ray powder diffraction spectra typically have the following peak diffraction angles (where "spacing" is shown as the "d-value" in FIG. 24):

TABLE 10

X-ray Diffraction Pattern of Compound
1 maleate (Crystalline Form I)

| Peak# | Diffraction angle (2 theta) | Spacing | Relative intensity |
|---|---|---|---|
| 1 | 3.086569 | 28.62517 | 15.12 |
| 2 | 5.525770 | 15.99363 | 47.95 |
| 3 | 6.845361 | 12.91319 | 33.34 |
| 4 | 10.789930 | 8.19964 | 14.63 |
| 5 | 11.528000 | 7.67627 | 16.64 |
| 6 | 13.741150 | 6.44451 | 12.46 |
| 7 | 16.140190 | 5.49161 | 100.00 |
| 8 | 16.329510 | 5.42837 | 53.02 |
| 9 | 17.837260 | 4.97277 | 17.37 |
| 10 | 19.805120 | 4.48289 | 19.75 |
| 11 | 21.490820 | 4.13492 | 29.27 |
| 12 | 23.778480 | 3.74204 | 24.24 |
| 13 | 24.430650 | 3.64361 | 10.93 |
| 14 | 28.340390 | 3.14921 | 14.75 |

Figure 25:
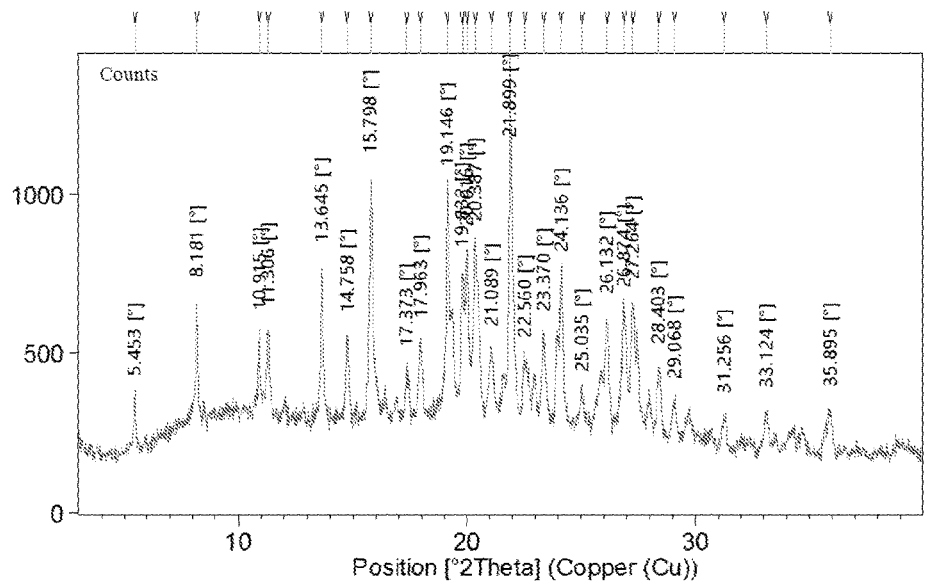
FIG. 25 shows an X-ray diffraction pattern of Crystalline Form J of Compound 1 maleate.

In another embodiment, provided herein is Crystalline Form J of Compound 1 maleate. As shown in FIG. 25, Crystalline Form J's X-ray powder diffraction spectra typically have the following peak diffraction angles (where "spacing" is shown as the "d-value" in FIG. 25):

TABLE 11

X-ray Diffraction Pattern of Compound
1 maleate (Crystalline Form J)

| Peak# | Diffraction angle (2 theta) | Spacing | Relative intensity |
|---|---|---|---|
| 1 | 5.453070 | 16.20669 | 13.27 |
| 2 | 8.181307 | 10.80732 | 37.62 |
| 3 | 10.914730 | 8.10616 | 29.43 |
| 4 | 11.306440 | 7.82619 | 30.63 |
| 5 | 13.644550 | 6.48992 | 46.61 |
| 6 | 14.758270 | 6.00257 | 28.91 |
| 7 | 15.798340 | 5.60966 | 68.33 |
| 8 | 17.372670 | 5.10470 | 20.50 |
| 9 | 17.962700 | 4.93833 | 27.49 |
| 10 | 19.145700 | 4.63578 | 65.51 |
| 11 | 19.832200 | 4.47683 | 45.48 |
| 12 | 20.015630 | 4.43622 | 50.52 |
| 13 | 20.387440 | 4.35614 | 51.65 |
| 14 | 21.088800 | 4.21283 | 25.59 |
| 15 | 21.899390 | 4.05869 | 100.00 |
| 16 | 22.560170 | 3.94129 | 22.65 |
| 17 | 23.370140 | 3.80649 | 29.34 |
| 18 | 24.136010 | 3.68742 | 44.18 |
| 19 | 25.034500 | 3.55707 | 14.16 |
| 20 | 26.132190 | 3.41010 | 33.46 |
| 21 | 26.873870 | 3.31764 | 35.15 |
| 22 | 27.263660 | 3.27109 | 37.17 |
| 23 | 28.403150 | 3.14240 | 21.20 |
| 24 | 29.067850 | 3.07204 | 12.67 |
| 25 | 33.124220 | 2.70452 | 10.36 |
| 26 | 35.894930 | 2.50187 | 10.55 |

Figure 26:
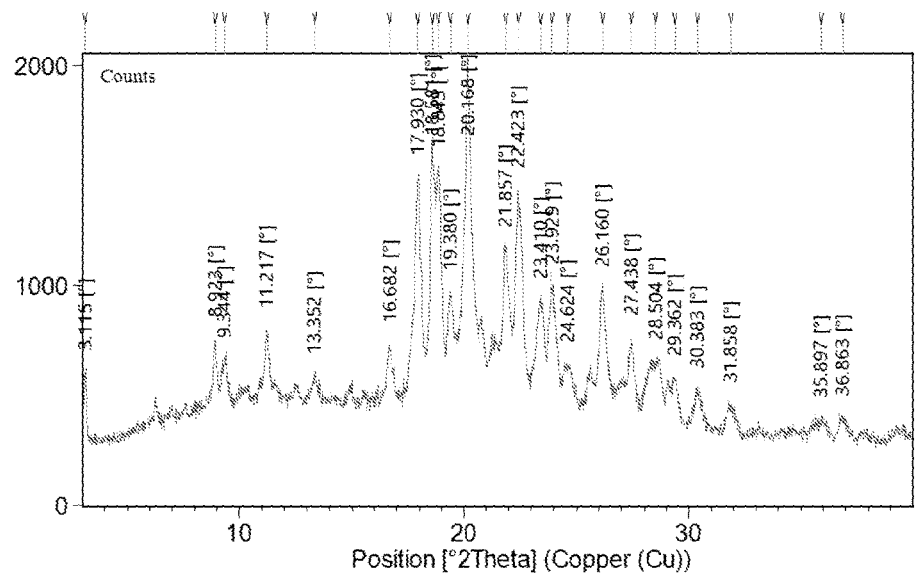
FIG. 26 shows an X-ray diffraction pattern of Crystalline Form K of Compound 1 maleate.

In another embodiment, provided herein is Crystalline Form K of Compound 1 maleate. As shown in FIG. 26, Crystalline Form K's X-ray powder diffraction spectra typically have the following peak diffraction angles (where "spacing" is shown as the "d-value" in FIG. 26):

TABLE 12

X-ray Diffraction Pattern of Compound
1 maleate (Crystalline Form K)

| Peak# | Diffraction angle (2 theta) | Spacing | Relative intensity |
|---|---|---|---|
| 1 | 3.115252 | 28.36168 | 18.53 |
| 2 | 8.922593 | 9.91104 | 19.50 |
| 3 | 9.344002 | 9.46499 | 13.34 |
| 4 | 11.217130 | 7.88830 | 20.74 |
| 5 | 16.682200 | 5.31439 | 15.77 |
| 6 | 17.929610 | 4.94737 | 63.98 |
| 7 | 18.580880 | 4.77540 | 75.23 |
| 8 | 18.842720 | 4.70963 | 66.62 |
| 9 | 19.380270 | 4.58020 | 32.04 |
| 10 | 20.168150 | 4.40301 | 100.00 |
| 11 | 21.857140 | 4.06644 | 45.71 |
| 12 | 22.422840 | 3.96512 | 62.91 |
| 13 | 23.410410 | 3.80004 | 32.07 |
| 14 | 23.929130 | 3.71882 | 36.53 |
| 15 | 24.623550 | 3.61550 | 14.68 |
| 16 | 26.159740 | 3.40657 | 37.04 |
| 17 | 27.437630 | 3.25074 | 23.90 |
| 18 | 28.503550 | 3.13156 | 17.59 |
| 19 | 29.361540 | 3.04197 | 13.34 |
| 20 | 30.382770 | 2.94201 | 10.52 |

Figure 27:
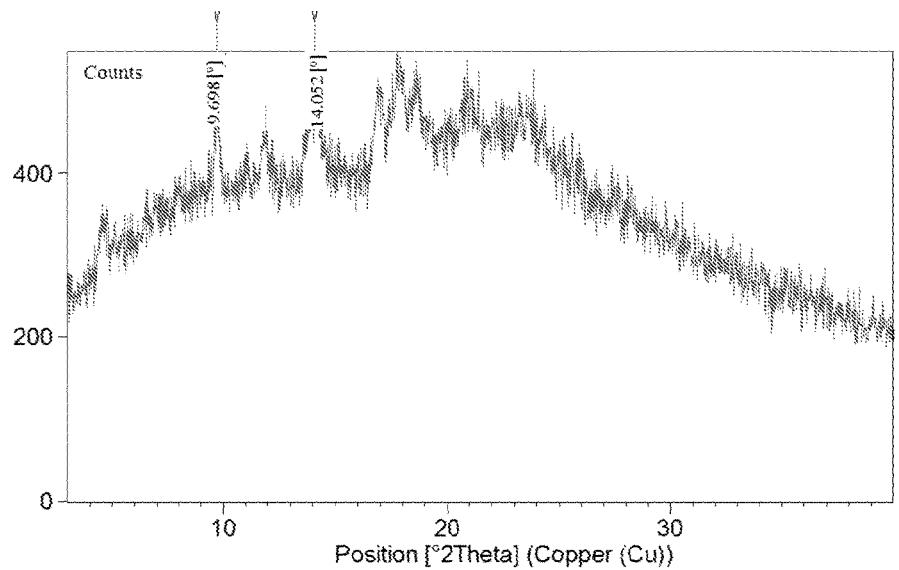
FIG. 27 shows an X-ray diffraction pattern of Crystalline Form L of Compound 1 maleate.

In another embodiment, provided herein is Crystalline Form L of Compound 1 maleate. As shown in FIG. 27, Crystalline Form L's X-ray powder diffraction spectra typically have the following peak diffraction angles (where "spacing" is shown as the "d-value" in FIG. 27):

TABLE 13

X-ray Diffraction Pattern of Compound
1 maleate (Crystalline Form L)

| Peak# | Diffraction angle (2 theta) | Spacing | Relative intensity |
|---|---|---|---|
| 1 | 9.698117 | 9.12016 | 77.30 |
| 2 | 14.051610 | 6.30281 | 100.00 |

Figure 28:
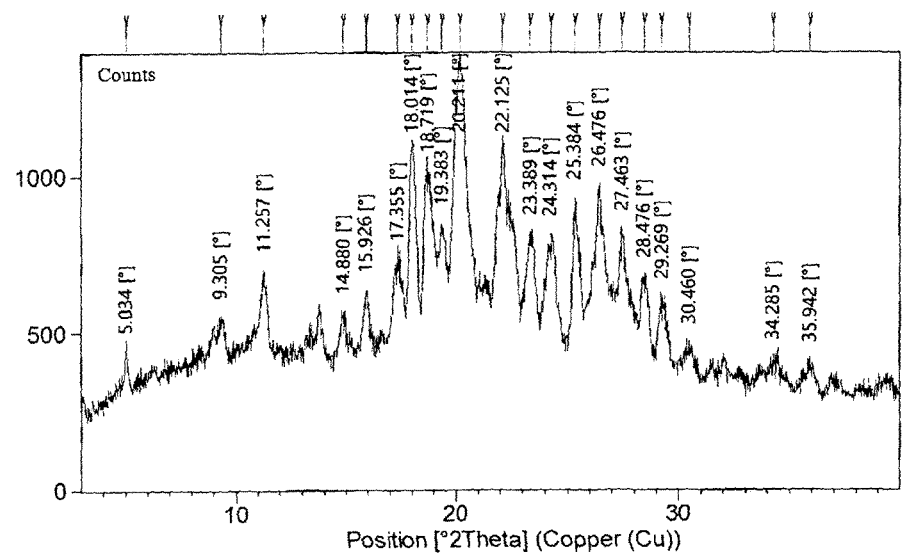
FIG. 28 shows an X-ray diffraction pattern of Crystalline Form M of Compound 1 maleate.

In another embodiment, provided herein is Crystalline Form M of Compound 1 maleate. As shown in FIG. 28, Crystalline Form M's X-ray powder diffraction spectra typically have the following peak diffraction angles (where "spacing" is shown as the "d-value" in FIG. 28):

TABLE 14

X-ray Diffraction Pattern of Compound
1 maleate (Crystalline Form M)

| Peak# | Diffraction angle (2 theta) | Spacing | Relative intensity |
|---|---|---|---|
| 1 | 5.034370 | 17.55360 | 12.31 |
| 2 | 9.305185 | 9.50438 | 13.27 |
| 3 | 11.256770 | 7.86061 | 27.54 |
| 4 | 14.880450 | 5.95356 | 11.84 |
| 5 | 15.926370 | 5.56486 | 19.75 |
| 6 | 17.354960 | 5.10987 | 30.82 |
| 7 | 18.013680 | 4.92447 | 72.36 |
| 8 | 18.719310 | 4.74040 | 61.47 |
| 9 | 19.383410 | 4.57946 | 43.82 |
| 10 | 20.210580 | 4.39386 | 100.00 |
| 11 | 22.125110 | 4.01780 | 70.61 |
| 12 | 23.388940 | 3.80347 | 42.17 |
| 13 | 24.313510 | 3.66090 | 42.06 |
| 14 | 25.384410 | 3.50883 | 55.22 |
| 15 | 26.475530 | 3.36665 | 60.01 |
| 16 | 27.463200 | 3.24777 | 45.10 |
| 17 | 28.476490 | 3.13447 | 29.51 |
| 18 | 29.269130 | 3.05137 | 22.64 |

Figure 33:
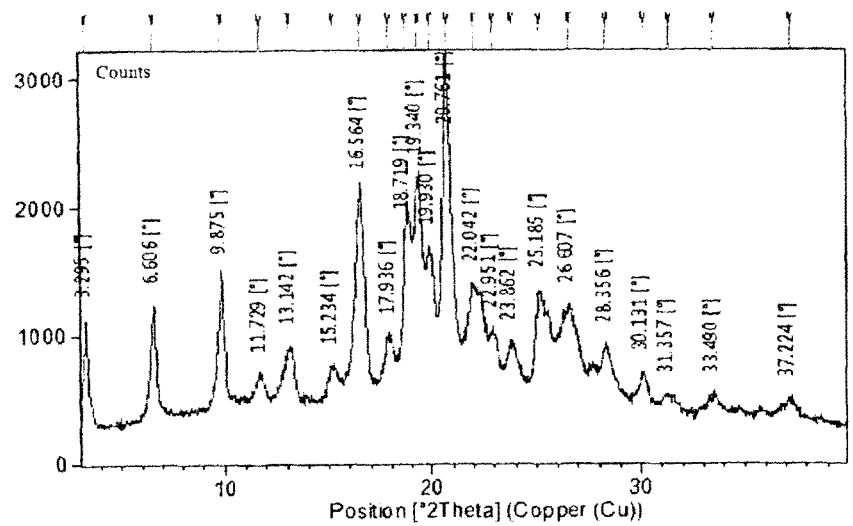
FIG. 33 shows an X-ray diffraction pattern of Crystalline Form N of Compound 1 maleate (1:1).

In another embodiment, provided herein is Compound 1 maleate (1:1) Crystalline Form N. As shown in FIG. 33, Crystalline Form N's X-ray powder diffraction spectra typically have the following peak diffraction angles (where "spacing" is shown as the "d-value" in FIG. 33):

TABLE 15

X-ray Diffraction Pattern of Compound
1 maleate (1:1) (Crystalline Form N)

| Peak# | Diffraction angle (2 theta) | Spacing | Relative intensity |
|---|---|---|---|
| 1 | 3.295141 | 26.81374 | 29.53 |
| 2 | 6.606152 | 13.38023 | 31.10 |
| 3 | 9.875418 | 8.95682 | 37.94 |
| 4 | 11.729470 | 7.54487 | 10.71 |
| 5 | 13.142240 | 6.73681 | 18.08 |
| 6 | 15.234010 | 5.81617 | 12.66 |
| 7 | 16.564110 | 5.35201 | 61.06 |
| 8 | 17.935520 | 4.94575 | 21.08 |
| 9 | 18.719110 | 4.74045 | 49.78 |
| 10 | 19.339860 | 4.58967 | 65.12 |
| 11 | 19.929920 | 4.45510 | 45.61 |
| 12 | 20.761080 | 4.27858 | 100.00 |
| 13 | 22.042190 | 4.03272 | 35.16 |
| 14 | 22.951470 | 3.87497 | 23.00 |
| 15 | 23.861870 | 3.72915 | 19.25 |
| 16 | 25.185120 | 3.53614 | 33.97 |
| 17 | 26.607380 | 3.35026 | 29.63 |
| 18 | 28.356330 | 3.14748 | 18.66 |
| 19 | 30.131030 | 2.96602 | 10.90 |
| 20 | 31.356510 | 2.85284 | 4.92 |
| 21 | 33.490100 | 2.67581 | 4.87 |
| 22 | 37.224360 | 2.41551 | 4.86 |

For Crystalline Forms A*, A**, A, B, C, D, F, G, H, I, J, K, L, M and N described above, only the main peaks (i.e., the most characteristic, significant, unique and/or reproducible peaks) are summarized; additional peaks may be obtained from the diffraction spectra by conventional methods. The main peaks described above can be reproduced within the margin of error (+ or −2 at the last given decimal place, or + or −0.2 at the stated value).

In another aspect, provided herein is a method for preparing the compound of Formula (I) or Formula (II).

In one embodiment, provided herein is a Crystalline Form A* of Compound 1 Sesqui-Maleate prepared or purified according to the procedures depicted in Scheme 1. The new synthetic methods and crystallization/recrystallization processes disclosed herein overcome many issues associated with the processes reported previously, such as preparation of the key chiral intermediate with >99% optical purity, and provide many advantages over the existing processes. Notably, the methods disclosed herein are especially suitable for reproducible, commercial-scale manufacture of Compound 1 Sesqui-Maleate Salt in high quality and good yields.

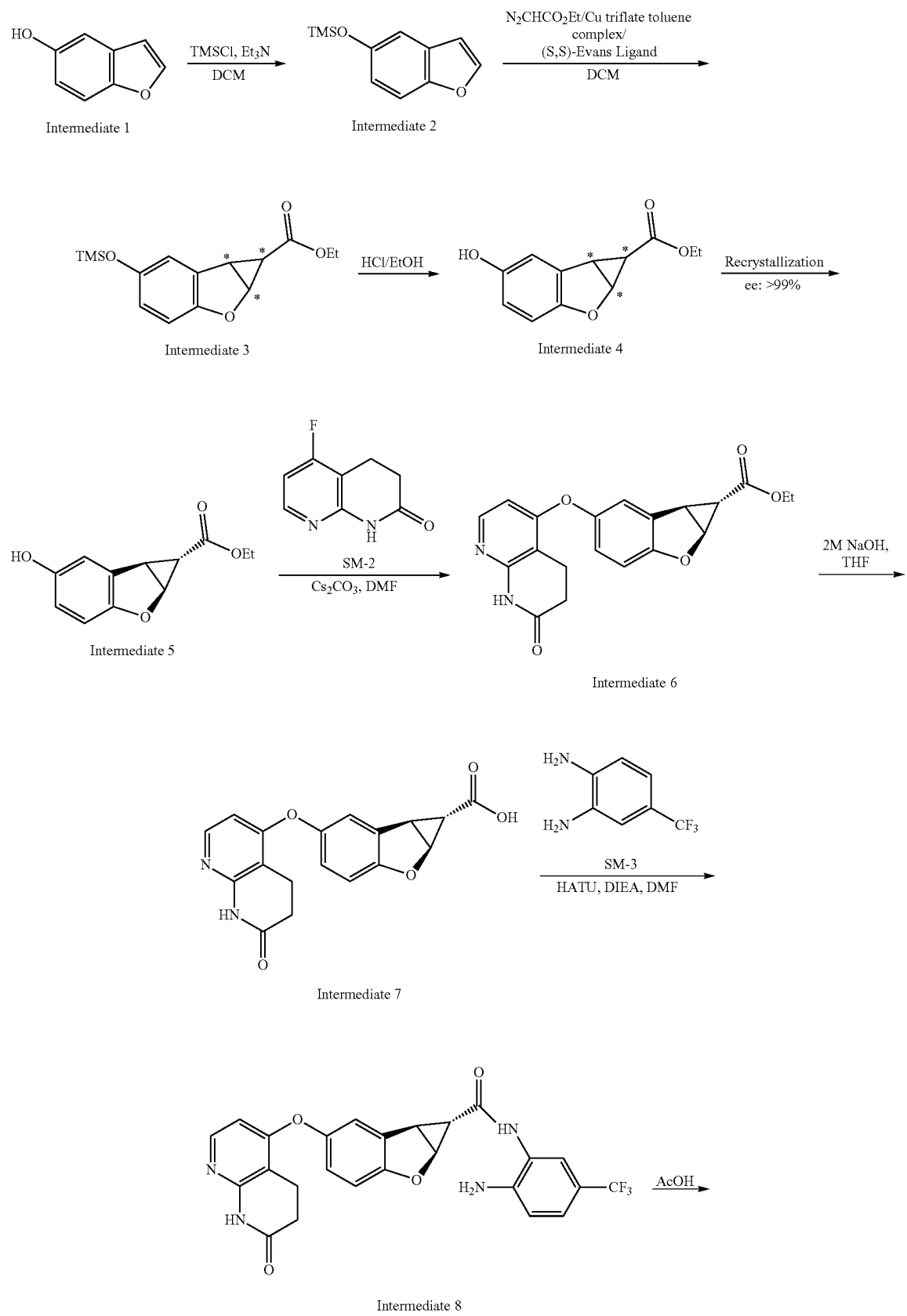

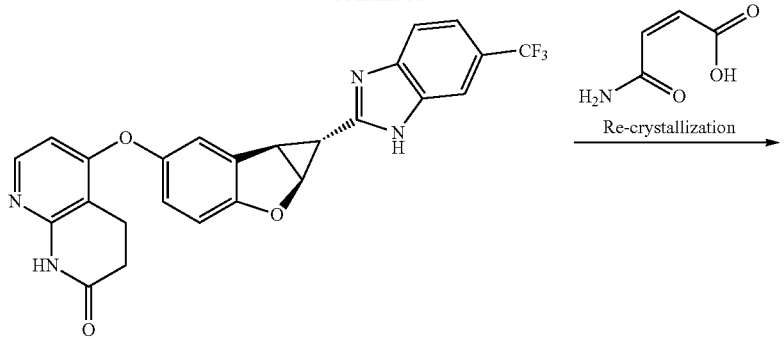

Compound 1 Free Base

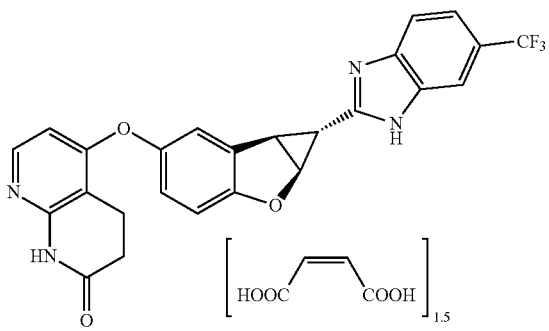

Formula I
(Compound 1 Sesqui-Maleate)

Crystalline Forms of Compound 1 Sesqui-Maleate salt can be prepared by the following general method: Crystalline Form A* of Compound 1 Sesqui-Maleate Salt is heated with a solvent until completely dissolved. After filtration, cooling, crystallization, filtration and drying, the corresponding different crystalline forms are obtained. An example of crystallization process for preparing Crystalline Form A of Compound 1 Sesqui-Maleate Salt is described in the Example 3 (below). The crystallization described above can be carried out in a single solvent, a mixture of organic solvents, or a mixture of water and organic solvent(s). Suitable organic solvents for the crystallization can be selected from, but not limited to, low alkyl alcohols, ketones, ethers, esters, halogenated hydrocarbons, alkanes, halogenated benzene, aliphatic nitrile, and other aromatic solvents. Preferred solvents include, e.g., isopropanol, ethyl acetate, water, N,N-dimethylformamide, methanol, ethanol, acetone, acetonitrile, and mixtures thereof.

The free base of Compound 1 was obtained originally as an amorphous solid, which is slightly hygroscopic with 2.2% water gain from 0 to 80% RH. No form transformation was observed after dynamic vapor sorption (DVS). It displayed an un-birefringence phenomenon with an irregular shape from polarized light microscope.

Disclosed herein are hydrochloride, methanesulfonate, 2-hydroxyethanesulfonate, L-tartrate, maleate and oxalate salts of Compound 1, wherein the maleate salt, in particular sesqui-maleate salt, was surprisingly discovered to possess the desired properties of a drug candidate. For example, Compound 1 did not appear to form a crystalline tartrate salt, and the oxalate salt has poor crystallinity. Though 2-hydroxyethanesulfonate, mesylate, and HCl salts showed relatively good solubility in water, HCl salt is chemically unstable with significant degradation after one week at 60° C. and 40° C./75% RH, and 2-hydroxyethanesulfonate and mesylate salts are both hygroscopic with around 4% weight gain from 0 to 80% RH. 2-Hydroxyethanesulfonate and mesylate salts also showed degradations after one week at 60° C. and 40° C./75% RH, and are thus expected to lack the desired long-term chemical stability. On the other hand, the sesqui-maleate salt (1:1.5 free base/maleic acid) has good crystallinity as demonstrated by the XRPD patterns disclosed herein, is slightly soluble in water, and did not show degradations after one week at 60° C. and 40° C./75% RH, indicating possible long-term stability; therefore, the sesqui-maleate salt was chosen for the further development.

If desirable or necessary, the purity of Compound 1 Sesqui-Maleate salt could be further improved by converting the sesqui-maleate salt into the maleate salt (1:1 ratio of free base/acid) through a methanol-slurry process. The formation of 1:1 maleate crystalline salt caused an efficient expulsion of the impurities. The amorphous form of free base could also be manufactured in high purity by treatment of the 1:1 maleate salt with a base and then extraction with a solvent. The sesqui-maleate crystalline salt with much higher purity was prepared by treating the free base with maleic acid (Scheme 2).

Scheme 2

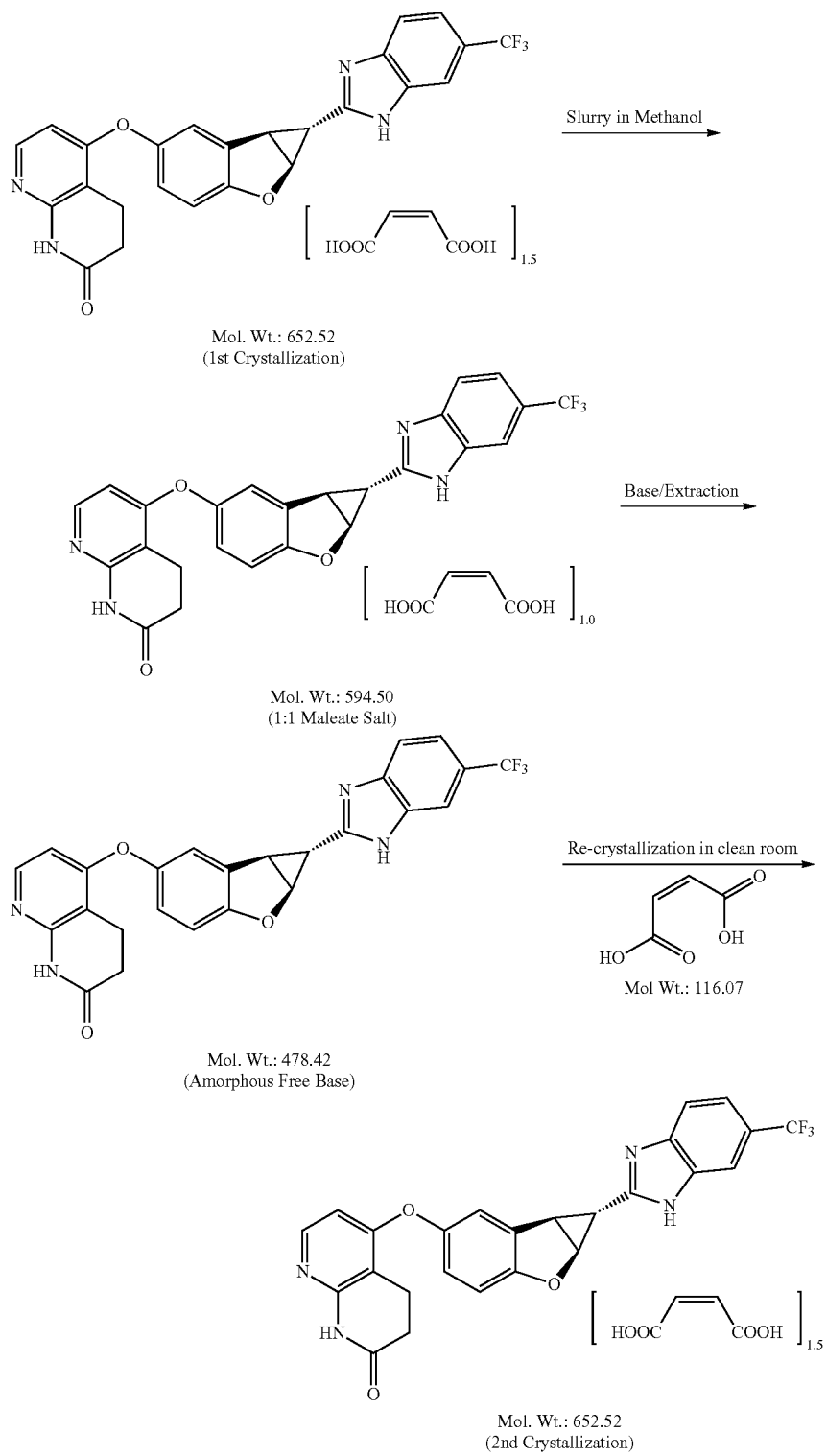

The term "low alkyl alcohols" herein includes straight-chain or branched-chain $C_1$-$C_8$, preferably $C_1$-$C_6$, more preferably $C_1$-$C_4$, alkyl alcohols. Specific examples include, but not limited to, methanol, ethanol, isopropanol, and butanol.

The term "about" as used herein, unless indicated otherwise, denotes that a number (e.g., temperature, pH, volume, etc.) can vary within ±10%, preferably within ±5%.

The crystallization of the crystalline forms of the present invention can also be conducted in an appropriate solvent system containing at least one solvent by evaporation of solvent, cooling and/or by addition of anti-solvents (solvents that are less able to solubilize the Compound 1 Sesqui-Maleate, including but not limited to those described herein) to achieve super-saturation in the solvent system.

Crystallization may be done with or without seed crystals, which is described in the present invention.

The individual crystalline forms provided by the present invention develop under specific conditions dependent on the particular thermodynamic and equilibrium properties of the crystallization process. Therefore, a person skilled in the art will know that the crystals formed are a consequence of the kinetic and thermodynamic properties of the crystallization process. Under certain conditions (e.g., solvent, temperature, pressure, and concentration of the compound), a particular crystalline form may be more stable than another crystalline form (or in fact more stable than any other crystalline forms). However, the relatively low thermodynamic stability of particular crystals may have advantageous kinetic stability. Additional factors other than kinetics, such as time, impurity distribution, stirring, and the presence or absence of seed crystals, etc., may also affect the crystalline form.

In another aspect, provided herein is pharmaceutical compositions each containing an effective amount of Compound 1 maleate in any of the above-described Crystalline Forms A*, A**, A, B, C, D, F, G, H, I, J, K, L, M and N in particular Crystalline Form A* of Compound 1 Sesqui-Maleate and a pharmaceutically acceptable carrier. The active compound(s) can be 1-99% (by weight), preferably 1-70% (by weight), or more preferably 1-50% (by weight), or most preferably, 5-40% (by weight), of the composition.

The pharmaceutical compositions can be administrated orally in forms such as capsules, tablets, pills, powders, sustained release injection in such form as a sterile solution, suspension or emulsion; through a local treatment form such as paste, cream, or ointment; or via a rectal form such as suppositories. The pharmaceutical compositions may be in a unit dosage form that is suitable for precise dosing applications. In addition, the pharmaceutical compositions may include other active ingredients.

Suitable pharmaceutical carriers include water, various organic solvents and various inert diluents or fillers. If necessary, the pharmaceutical compositions may contain various additives, such as spices, adhesives and excipients. For oral administration, tablets and capsules can contain various excipients such as citric acid, a variety of disintegrating agents such as starch, alginic acids, and some silicates, and a variety of adhesives such as sucrose, gelatin and Arabic gum. In addition, lubricants including magnesium stearate and talc fillers are commonly used in the production of tablets. The same types of solid components can also be used to formulate soft and hard gelatin capsules. When an aqueous suspension is needed for oral administration, the active compound can be mixed with a variety of sweeteners or flavoring agents, pigments or dye combinations. If necessary, a variety of emulsifiers can be employed or suspensions generated; diluents such as water, ethanol, propylene glycol, glycerin, or their combination can be utilized.

The above-described pharmaceutical compositions are preferably administrated orally.

The above-described pharmaceutical compositions are preferably in the capsule or tablet form.

In another aspect, provided herein is use of the compounds of the present application (i.e., Compound 1 maleate and any of the above-described Crystalline Forms A*, A**, A, B, C, D, F, G, H, I, J, K, L, M and N) in the manufacture of medicaments that are useful for the treatment of cancers responsive to inhibition of Braf kinase or other kinases such EGFR, VEGFR, EPHA, EPHB, or the like.

In one embodiment, provided herein is use of the compounds of the present application (i.e., Compound 1 maleate and any of the above-described Crystalline Forms A*, A**, A, B, C, D, F, G, H, I, J, K, L, M and N) in the manufacture of medicaments that are useful for the treatment or prevention of mammalian pancreatitis, kidney disease, cancer, angiogenesis, or angiogenesis-related diseases.

Compound 1 maleate and any of the Crystalline Forms A*, A**, A, B, C, D, F, G, H, I, J, K, L, M and N or Compound 1 maleate (1:1) Crystalline Form N of the present application can be used to treat or prevent diseases selected from, but not limited to, tumor angiogenesis, chronic inflammatory disease such as rheumatoid arthritis, atherosclerosis, skin diseases such as psoriasis and scleroderma, diabetes-induced skin diseases, diabetic retinopathy, premature retinopathy, age-related degeneration stains, hemangioma, glioma, Kaposi internal tumor, ovarian cancer, breast cancer, lung cancer, pancreatic cancer, lymphoma, prostate, colon and skin tumors, and their complications. Among the mammals mentioned herein, human beings are preferred.

Target diseases for the above-described treatment methods are preferably selected from B-RAF, NRAS and K-RAS mutant tumors such as B-RAF or NRAS or K-RAS mutant non-small cell lung cancer, colorectal cancer, endometrial cancer, kidney cancer, bone cancer, liver cancer, bladder cancer, chest cancer, neck cancer, esophageal cancer, gastric cancer, colon cancer, rectal cancer, breast cancer, ovarian cancer, melanoma, skin cancer, adrenal cancer, cervical cancer, lymphoma, or thyroid tumors, and their complications.

The above-described methods can be applied in combination with any chemical therapy (for example, MEK inhibitors), biological therapy, or radiation therapy.

The dosage of the active ingredient or compound when administered will be determined by the individual needs of the patient to be treated, administration route, severity of disease or illness, dosing schedule, as well as evaluation and judgment of the designated doctor. However, based on the active compound, the preferred range of the effective dosage can be approximately 0.01-120 mg daily per kilogram of body weight; or more preferably 0.1-10 mg per day per kilo gram of body weight in single or separate doses. In some cases, it is more suitable to apply the lower end of the above described dosage ranges, while in other cases the higher dosages may be used without causing harmful side effects.

Another aspect of the present application is to provide Compound 1 Sesqui-Maleate for clinical applications. In particular, the present invention relates to clinical treatment with Compound 1 maleate with the following treatment options for cancer patients: the dosage of Compound 1 maleate and/or Crystalline Form A*, A**, A, B, C, D, F, G, H, I, J, K, L, M and N can be 1-100 mg/day with the administration frequency being 1-3 times a day; a preferred dosage is 5-50 mg/day with the administration frequency being 1-3 times a day; a more preferred dosage is 5-60 mg/day with the administration frequency being 1 time/day; an even more preferred dosage is 10-50 mg/day with the administration frequency being 1 time 1 a day.

The following synthetic methods, specific examples, and efficacy tests further describe certain aspects of the present invention. They shall not limit or restrict the scope of the present invention in any way.

EXAMPLES

The examples below are intended to be exemplary and efforts have been made to ensure accuracy with respect to numbers used (for example, amounts, temperature, etc.), but some experimental errors and deviations should be accounted for. Unless indicated otherwise, temperature is in degrees Centigrade. Reagents were purchased from commercial suppliers such as Sigma-Aldrich, Alfa Aesar, or TCI, and were used without further purification unless otherwise indicated.

Unless otherwise indicated, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

Unless otherwise indicated, column chromatography purification was conducted on a Biotage system (Manufacturer: Dyax Corporation) having a silica gel column or on a silica SepPak cartridge (Waters), or was conducted on a Teledyne Isco Combiflash purification system using pre-packed silica gel cartridges.

$^1$H NMR spectra and $^{13}$C NMR were recorded on a Varian instrument operating at 400 MHz using DMSO-$d_6$ as solvent.

X-ray intensity data from a colorless plate-like crystal were measured at 173(2) K using aBruker APEX-II CCD diffractometer (Cu Kα radiation, λ=1.54178 Å). Polarized light microscopic picture was captured at room temperature.

In the following examples, the abbreviations below may be used:
AcOH Acetic acid
ACN Acetonitrile
API Active pharmaceutical ingredient, hereinafter sometimes referred to as Compound 1
Aq Aqueous
Brine Saturated aqueous sodium chloride solution
Bn Benzyl
BnBr Benzyl Bromide
$CH_2Cl_2$ Dichloromethane
DMF N,N-Dimethylformamide
Dppf 1,1"-bis(diphenylphosphino)ferrocene
DBU 1,8-diazabicyclo[5.4.0]undec-7-ene
DIEA or DIPEA N,N-diisopropylethylamine
DMAP 4-N,N-dimethylaminopyridine
DMF N,N-dimethylformamide
DMSO Dimethyl sulfoxide
EtOAc Ethyl acetate
EtOH Ethanol
$Et_2O$ or ether Diethyl ether
g grams
h or hr hour
HATU O-(7-Azabenzotriazol-1-yl)-N,N,N',N'-tetramethyluronium hexafluorophosphate
HCl Hydrochloric acid
HPLC High-performance liquid chromatography
IPA 2-propanol
i-PrOH Isopropyl alcohol
Mg milligrams
mL milliliters
mmol millimole
MeCN Acetonitrile
MeOH Methanol
min minutes
ms or MS Mass spectrum
$Na_2SO_4$ Sodium sulfate
PE petroleum ether
PPA Polyphosphoric acid
Rt Retention time
Rt or rt Room temperature
TBAF Tetra-butyl ammonium fluoride
TBSCl tert-Butyldimethylsilyl chloride
TFA Trifluoroacetic acid
THF tetrahydrofuran
TLC thin layer chromatography
TMSCl Trimethylsilyl chloride
μL microliters

Example 1: Formation of Salts of Compound 1 with Various Salt-Forming Agents

Example 1A: Preparation of Free Base of Compound 1 and Crystalline Form A* of Compound 1 Sesqui-Maleate Step 1: Synthesis of Intermediate 1

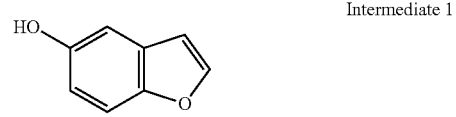

Intermediate 1

To a stirred solution of EtONa (154 kg) in DMF (989 kg) was added EtSH (68.6 kg) at an inner temperature ≤35° C. under nitrogen protection. The mixture was stirred for 60-90 min at the inner temperature ≤35° C. 5-Methoxybenzofuran (58.75 kg) in DMF (55.0 kg) was added. The mixture was heated to 110-130° C., stirred for 45 hrs, and then concentrated under vacuum below 90° C. After the mixture was cooled to 10~20° C., 2N HCl (1326 kg) was added dropwise, followed by addition of EtOAc (531 kg) and $H_2O_2$ (129 kg) at the inner temperature ≤35° C. The mixture was stirred for 30~60 min. After separation of the organic layer, the aqueous phase was extracted with EtOAc. The combined organic phase was washed with saturated brine twice, and then the solvent was evaporated to dryness. MeOH and a solution of NaOH (44.5 kg) in water (185 kg) were added dropwise into the residue below 40° C. The mixture was stirred for 5-7 hrs at 30~40° C. Active carbon (74 kg) wet up with water (77 kg) was added. The mixture was stirred for 4-6 hrs at 30~40° C. and filtered; and the filter cake was washed with MeOH and water. DCM was charged into the filtrate and pH was adjusted to 1 with 35% aq. HCl below 40° C. The aqueous phase was extracted with DCM, and the organic phase was washed with 25% NaCl and concentrated below 40° C. The residue was used in the next step directly. $^1$H NMR (400 MHz, DMSO-d6) δ 9.14 (s, 1H), 7.86 (d, J=2.0 Hz, 1H), 7.36 (d, J=8.8 Hz, 1H), 6.94 (d, J=2.4 Hz, 1H), 6.79 (dd, J=2.0, 0.9 Hz, 1H), 6.74 (dd, J=8.8, 2.4 Hz, 1H) ppm. MS: M/e 135 (M+1)$^+$.

Step 2: Synthesis of Intermediate 2

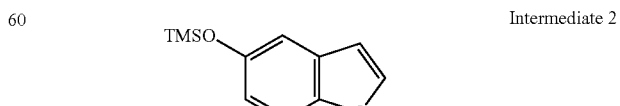

Intermediate 2

To a stirred solution of benzofuran-5-ol (Intermediate 1, 33.1 kg) and $Et_3N$ (50.8 kg) in DCM (155 kg) was added dropwise a solution of TMSCl (30.4 kg) in DCM (50 kg) at −5 to 0° C. The mixture was warmed to 0~10° C. and stirred at the temperature for 2 hours (IPC checked INT-1/INT-2=37.4%). The mixture was cooled to between −5 and 0° C. and was added dropwise a solution of TMSCl (10.6 kg) in DCM (8 kg), and then the mixture was warmed to 0~10° C. and stirred at the temperature for 1 h. The mixture was concentrated below 40° C., and to the mixture was added n-heptane. The mixture was stirred for 20-30 mins and filtered, and the cake was washed with n-heptane. The solvent was distilled out from the filtrate to obtain a crude Intermediate 2 (INT-2%: 62.7%, KF: 0.01%). To a stirred solution of the crude Intermediate 2 above and Et₃N (8.6 kg) in DCM (149 kg) was added dropwise a solution of TMSCl (9.0 kg) in DCM (10 kg) at −5 to 0° C. The mixture was warmed to 0~10° C. and stirred at the temperature for 1 h (TLC showed the reaction was finished). The reaction mixture was concentrated below 40° C., and to the mixture was added n-heptane. The mixture was stirred for 20-30 mins and then filtered, and the cake was washed with n-heptane. The solvent was distilled out from the filtrate to obtain Intermediate 2 (41.5 kg, INT-2%: 98.1%) as a colorless oil. ¹H NMR (400 MHz, DMSO-d6) δ 7.69 (d, J=2.0 Hz, 1H), 7.21 (d, J=8.8 Hz, 1H), 6.84 (d, J=2.5 Hz, 1H), 6.61 (d, J=2.0 Hz, 1H), 6.56 (dd, J=8.8, 2.5 Hz, 1H), 0.00 (s, 9H) ppm.

Step 3: Synthesis of Intermediate 3

Intermediate 3

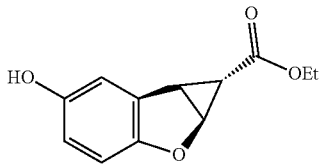

Copper (I) triflate (2:1 complex with toluene, 0.41 kg) and (S,S)-Evans Ligand (0.552 kg) were stirred in DCM (160 kg) at ambient temperature under N₂ atmosphere for 1-2 hrs. Intermediate 2 (37.0 kg) was added, followed by a slow addition of ethyl diazoethanoate (58 kg) in DCM (450 kg) at 20~30° C. The reaction was stirred for 0.5~1 h at 20~30° C. (IPC: INT-2/INT-3≤0.2%, residual N₂CHCO₂Et: 0.05%≤1.0%). A solution of EDTA disodium (0.05 mol/L, 150 kg) was added to the reaction mixture for 40~50 min at 20~30° C. in three times. The organic phase was washed with 25% aqueous NaCl at 20~30° C. in two times and concentrated below 30° C. The residue was distilled under reduced pressure and crude Intermediate 3 (36.26 kg, 84.5%) was collected at 120~144° C. The crude compound included the endo-enantiomer which could be removed in the next step. ¹H NMR (400 MHz, DMSO-d6) δ 6.79 (d, J=2.4 Hz, 1H), 6.59 (d, J=8.4 Hz, 1H), 6.42 (dd, J=8.4, 2.4 Hz, 1H), 4.95 (dd, J=5.4, 1.0 Hz, 1H), 3.08 (dd, J=5.4, 3.2 Hz, 1H), 1.02 (dd, J=3.1, 1.2 Hz, 1H), 0.00 (s, 9H) ppm.

Steps 4 and 5: Syntheses of Intermediate 5 and Intermediate 6

Intermediate 5

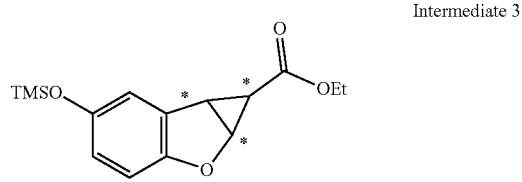

Intermediate 6

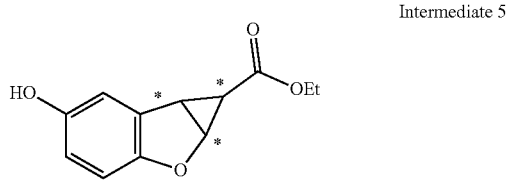

To a solution of Intermediate 4 (36.3 kg) in MeOH (108 kg) was added a solution of HCl/MeOH (5M, 0.11 kg) at 20~30° C., and the mixture was stirred for 2-3 hrs (IPC: L/M: 0.5%, chiral purity 90.0%). Et₃N (0.22 kg) was added dropwise at 20~30° C. The mixture was concentrated and the residue was diluted with n-heptane/EtOAc (4:1) and then concentrated. After adjusting the temperature to 10~20° C. and stirring for 2~4 hrs at 10~20° C., the mixture was filtered to give a wet product (Intermediate 5: 94.0%, chiral purity: 90.5%). ¹H NMR (400 MHz, DMSO-d6) δ 9.05 (s, 1H), 6.89 (d, J=2.4 Hz, 1H), 6.72 (d, J=8.4 Hz, 1H), 6.55 (dd, J=8.4, 2.4 Hz, 1H), 5.11 (dd, J=5.4, 1.0 Hz, 1H), 3.27 (dd, J=5.4, 3.0 Hz, 1H), 1.19-1.17 (m, 1H) ppm. The crude product was slurried with n-heptane/EtOAc (20:1) three times to give a light yellow solid, which was dried for 12~16 hrs at 40~50° C. to give 16.55 kg product (Intermediate 6: 98.6%; chiral purity: 99.3%).

Steps 6 and 7: Syntheses of Intermediate 7 and Intermediate 8

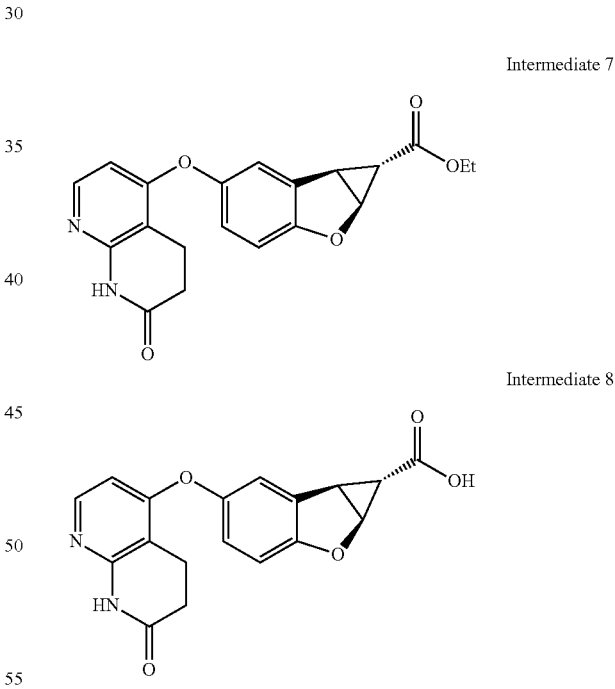

To a solution of Intermediate 6 (14 kg) and 5-fluoro-3,4-dihydro-1,8-naphthyridin-2(1H)-one (SM2, 11.2 kg) in DMF (66 kg) was added Cs₂CO₃ (26 kg) at 40~60° C., and the mixture was warmed to 110~120° C. and stirred for 3 hrs at 110~120° C. The reaction pH was adjusted to 6 with acetic acid (12.0 kg) at 25~35° C. Water (520 kg) was added and the mixture was stirred for 1~2 hrs. After filtration, the solid was slurried with EA (78 kg) to get a wet product (the purity: (Intermediate 7+Intermediate 8) %: 98%). An aqueous sodium hydroxide solution (125 kg, 2M) was added to a stirred solution of the wet product in THF (240 kg) and stirred for 2~3 hrs at 20~30° C. (IPC: INT-7/INT-8: 0.9%). The mixture was adjusted to pH 4~5 with 4N HCl (37 kg) at 20~30° C. and then stirred for 0.5~1 h. The mixture was concentrated at below 50° C. and a solid precipitated out of the solution. After filtration, the wet product was re-slurried in THF at 35~45° C. for 1~2 hrs, and then filtered. The resultant wet product was dried for 40 hrs at 45~65° C. to give the title compound Intermediate 8 (18.95 kg: chemical purity 99%, chiral purity 100%). $^1$H NMR (400 MHz, DMSO-d6) δ 12.59 (s, 1H), 10.43 (s, 1H), 7.92 (d, J=5.8 Hz, 1H), 7.29 (d, J=2.4 Hz, 1H), 6.97 (d, J=8.8 Hz, 1H), 6.93 (dd, J=8.8, 2.4 Hz, 1H), 6.21 (d, J=5.8 Hz, 1H), 5.21 (dd, J=5.4, 1.0 Hz, 1H), 3.27-3.25 (m, 1H), 2.89 (t, J=7.8 Hz, 2H), 2.51 (d, J=8.8 Hz, 2H), 1.19 (dd, J=3.0, 1.0 Hz, 1H) ppm. MS: M/e 339 (M+1)$^+$.

Step 8: Synthesis of Intermediate 9

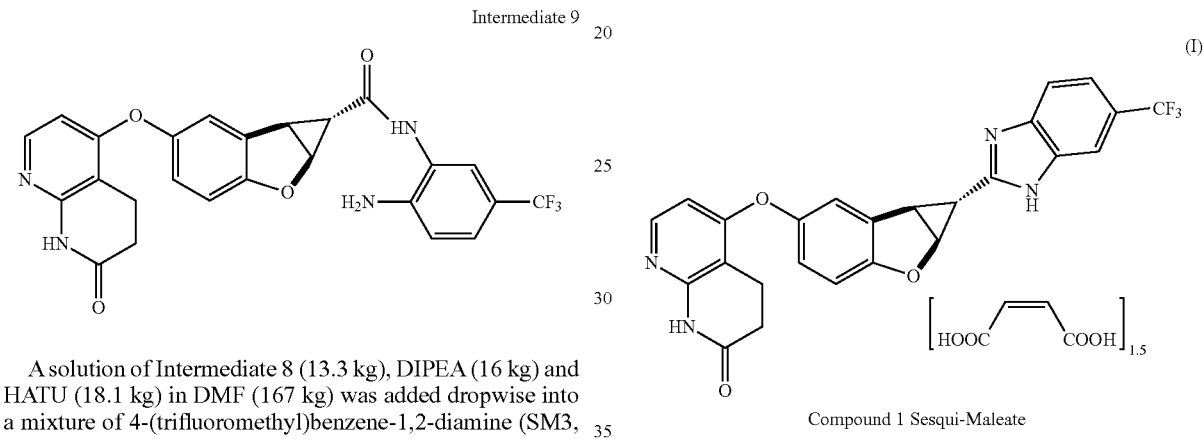

Intermediate 9

A solution of Intermediate 8 (13.3 kg), DIPEA (16 kg) and HATU (18.1 kg) in DMF (167 kg) was added dropwise into a mixture of 4-(trifluoromethyl)benzene-1,2-diamine (SM3, 7.6 kg) in DMF (74 kg) at 0~15° C. The mixture was stirred at 20~25° C. for 4-6 hrs (IPC: INT-9/INT-9: not detected). Active carbon (5.3 kg) in DMF (7.5 kg) was added into the reaction mixture, stirred for 2~4 hrs at 40~45° C., and then filtered. Water (846 kg) was added dropwise into the filtrate at 15~30° C., and a solid precipitated out of the solution when stirred for 1~2 hrs. The precipitate was filed and slurried in EtOH at 20~30° C. for 2-4 hrs. After filtration, the wet product was dried for 37 hrs at 45~60° C. to obtain the title compound Intermediate 9 (17.60 kg: 95.5%).

Step 9: Syntheses of Free Base of Compound 1

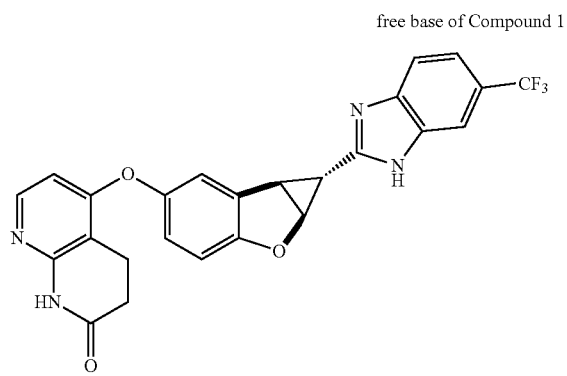

free base of Compound 1

A solution of Intermediate 9 (17 kg) and water (1.5 kg) in AcOH (360 kg) was stirred at 65-70° C. for 20 hrs (IPC: R/S≤1.0%). The mixture was concentrated to dryness at below 55° C., and active carbon (17 kg) with MeOH (32 kg) was added to the residue. The mixture was stirred for 1 h at about 50° C. After filtration, the filtration was concentrated to remove the solvent at below 45° C. EA (160 kg) and water (330 kg) were added to the residue, followed with an aqueous solution of NaOH (2 mol/L) until pH to 8-9 at 20-30° C. The organic layer was separated, and extracted the aqueous phase with EA. The combined organic phase was washed with water twice, concentrated to dryness to obtain Compound 1 in the form of free base. $^1$H-NMR (600 MHz, DMSO-d$_6$) δ 12.84 (s, 1H), 10.47 (s, 1H), 7.98 (d, J=5.8 Hz, 1H), 7.86 (d, J=1.2 Hz, 1H), 7.69 (m, 1H), 7.48 (t, J=6.2 Hz, 1H), 7.38 (d, J=2.6 Hz, 1H), 7.08 (d, J=8.7 Hz, 1H), 7.02 (dd, J=8.7, 2.6 Hz, 1H), 6.29 (d, J=5.8 Hz, 1H), 5.43 (dd, J=5.4, 1.2 Hz, 1H), 3.55 (dd, J=5.3, 3.3 Hz, 1H), 2.95 (t, J=7.7 Hz, 2H), 2.55 (t, J=7.7 Hz, 2H), 1.97 (d, J=1.3 Hz, 1H) ppm.

Step 10: Syntheses of Compound 1 Sesqui-Maleate (I)

Compound 1 Sesqui-Maleate

Figure 29:
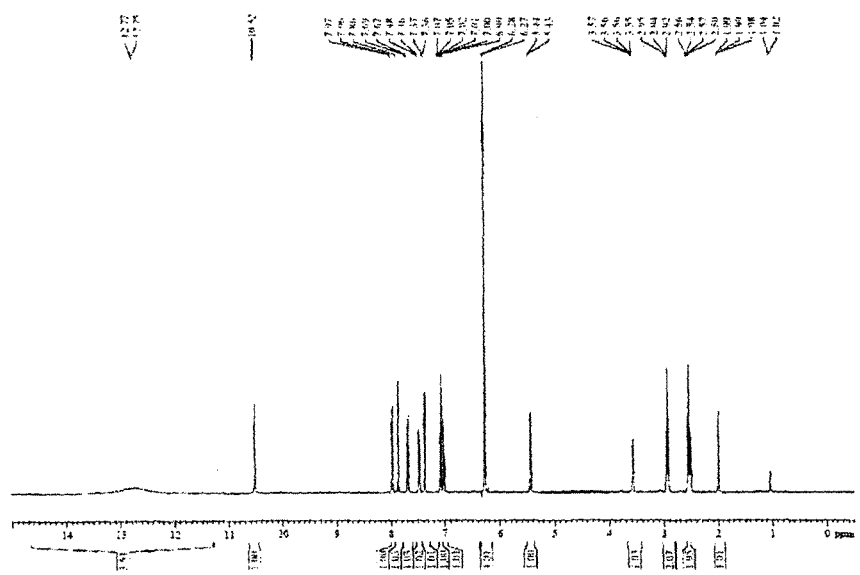
FIG. 29 shows a $^1$H-NMR spectrum of Crystalline Form A* of Compound 1 Sesqui-Maleate.
Figure 30:
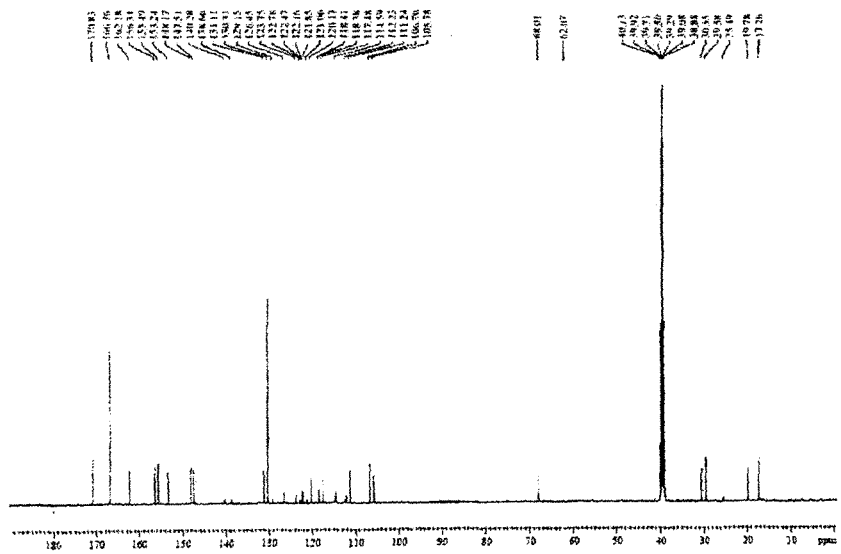
FIG. 30 shows a $^{13}$C-NMR spectrum of Crystalline Form A* of Compound 1 Sesqui-Maleate.

IPA (83 kg) was added to the residue of Step 9. Maleic acid (5 kg) in water (29 kg) was added into the mixture and stirred for 4 hrs at about 50° C., then cooled to 35° C. and stirred for 12 hrs at that temperature. The resultant solid was filtered, dried at 40~60° C., and micronized in a micronizer to give a white powder (Compound 1 Sesqui-Maleate Salt, 8.36 kg) with particle sizes of D90=4.1 μm, D10=1.5 μm, D50=2.4 μm. The powder X-ray diffraction pattern method was used to characterize the structure of Crystalline Form A*, see FIG. 2. $^1$H-NMR spectra for Crystalline Form A* of Compound 1 Sesqui-Maleate is shown in FIG. 29. $^{13}$C-NMR spectra for Crystalline Form A* of Compound 1 Sesqui-Maleate is shown in FIG. 30.

The solubility study showed a much better aqueous solubility (0.020 mg/mL) of Crystalline Form A* of Compound 1 Sesqui-Maleate was obtained than that (<LOQ at 0.001 mg/mL) of the free base of Compound 1.

Figure 31:
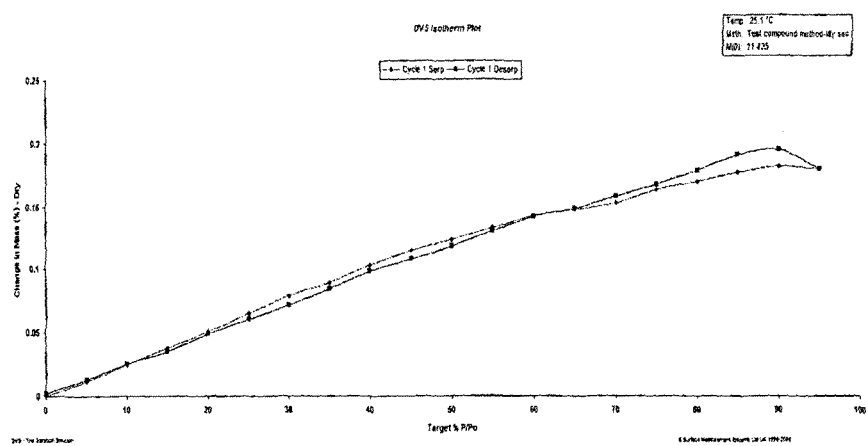
FIG. 31 shows Hygroscopicity (i.e., Moisture sorption) of Crystalline Form A* of Compound 1 Sesqui-Maleate by DVS.

Crystalline Form A* of Compound 1 Sesqui-Maleate was found to be non-hygroscopic with only 0.1801% water uptake exposed to 95% RH as shown in FIG. 31.

Example 1B: Preparation of Salts of Compound 1 with Other Salt-Forming Agents

Around 150 mg of free base of Compound 1 was dissolved in a 40 mL glass vial with 2 mL of IPA individually. A solution of appropriate salt-forming agents in IPA (The slat-forming agents were pre-dissolved in IPA, for those salt-forming agents which could not be dissolved, the suspensions were heated to be dissolved) according to the molar ratio listed in Table 16 was slowly titrated into free base solution respectively on the magnetic stirrer, and then kept stirring at room temperature for 24 hours to precipitate out solid. If no solid was obtained, an anti-solvent (e.g., heptane) was added slowly into the solution to get the precipitation. The centrifugal solid was determined by XRPD to determine if new crystalline form was obtained, and then dried under vacuum at 40° C. overnight for further characterization. API and pure solid acid suspended in IPA were used as API control and pure solid salt-forming agent control to distinguish salt/co-crystal formation and polymorphism of API or solid salt-forming agents.

In addition to formation of crystalline salts with maleic acid, solids of crystalline forms were also found from the following five acids including hydrochloric acid (FIG. 3), methanesulfonic acid (FIG. 4), 2-hydroxyethanesulfonic acid (FIG. 5), L-tartaric acid (FIG. 6, the true tartrate salt may not be formed and it is the just the polymorph of the free base since no chemical shift was detected for tartrate), and oxalic acid (FIG. 7), which showed different crystal form from free base, API control and solid acid control. Among the formed crystalline salts, 2-hydroxyethanesulfonate and maleate have better crystallinity than the other four (hydrochloric acid, methanesulfonic acid, L-tartaric acid, and oxalic acid).

Figure 8:
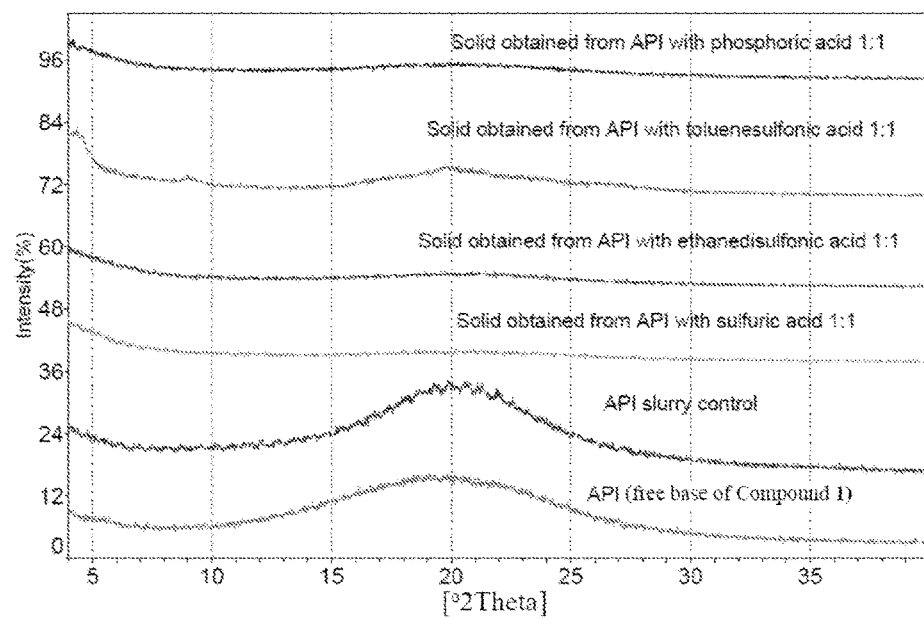
FIG. 8 shows overlay of X-ray diffraction patterns of solids obtained from Compound 1 with phosphoric acid (1:1), toluenesulfonic acid (1:1), ethanedisulfonic acid (1:1), sulfuric acid (1:1), API slurry control and API.
Figure 9:
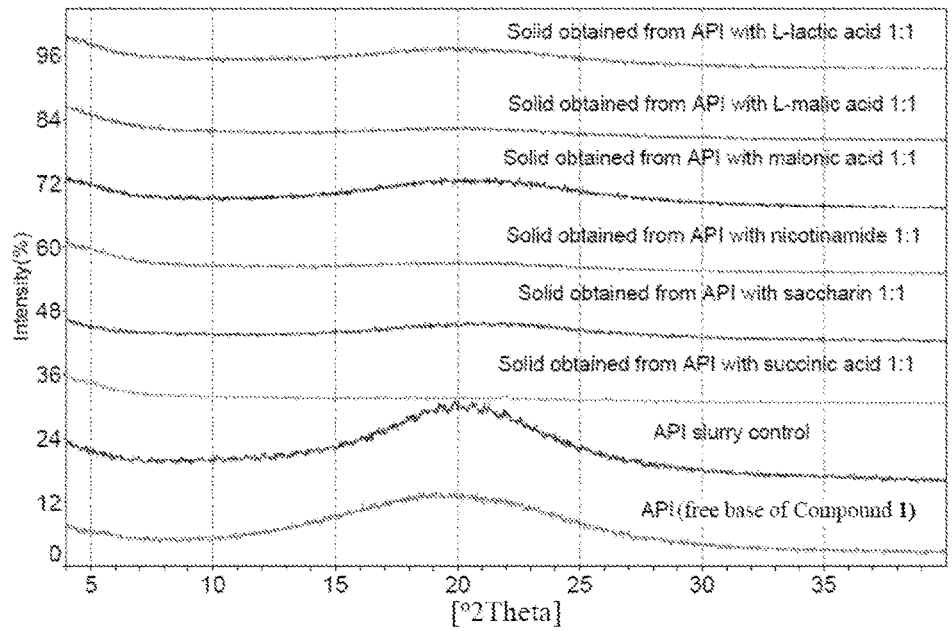
FIG. 9 shows overlay of X-ray diffraction patterns of solids obtained from Compound 1 with L-lactic acid (1:1), L-malic acid (1:1), malonic acid (1:1), nicotinamide (1:1), saccharin (1:1), succinic acid (1:1), API slurry control and API.
Figure 10:
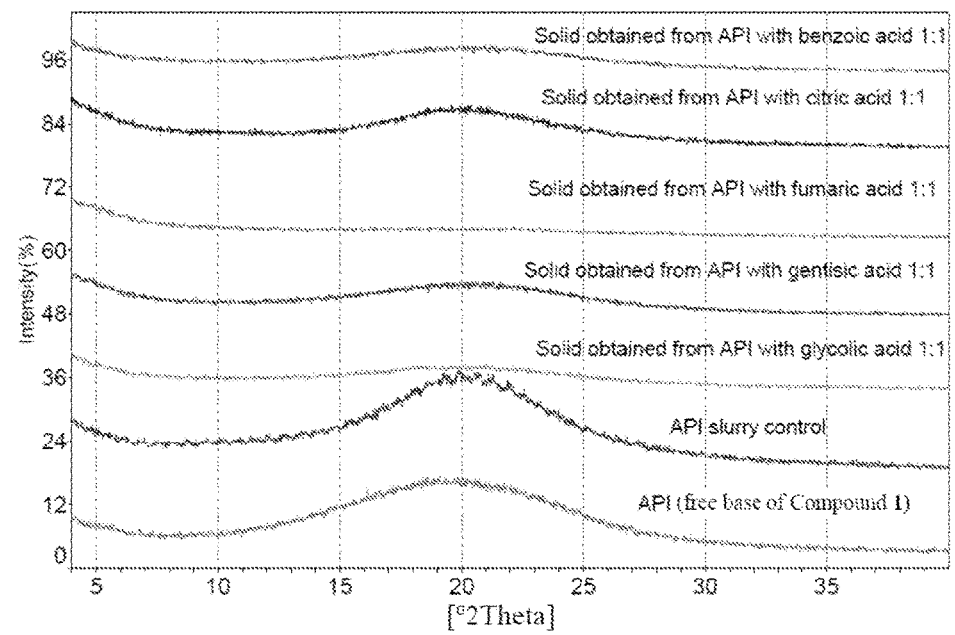
FIG. 10 shows overlay of X-ray diffraction patterns of solids obtained from Compound 1 with benzoic acid (1:1), citric acid (1:1), fumaric acid (1:1), gentisic acid (1:1), glycolic acid (1:1), API slurry control and API.
Figure 11:
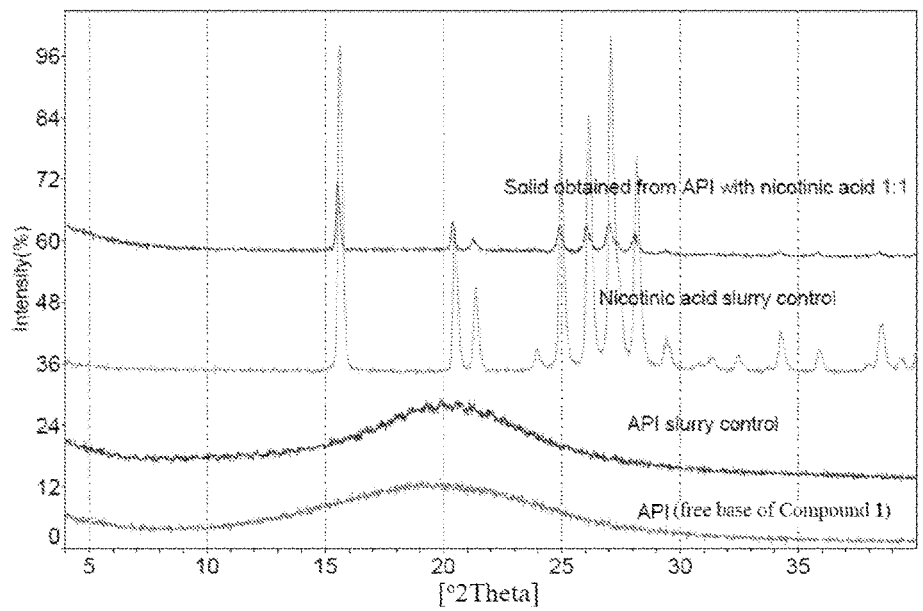
FIG. 11 shows overlay of X-ray diffraction patterns of solid obtained from Compound 1 with nicotinic acid (1:1), nicotinic acid slurry control, API slurry control and API.
Figure 12:
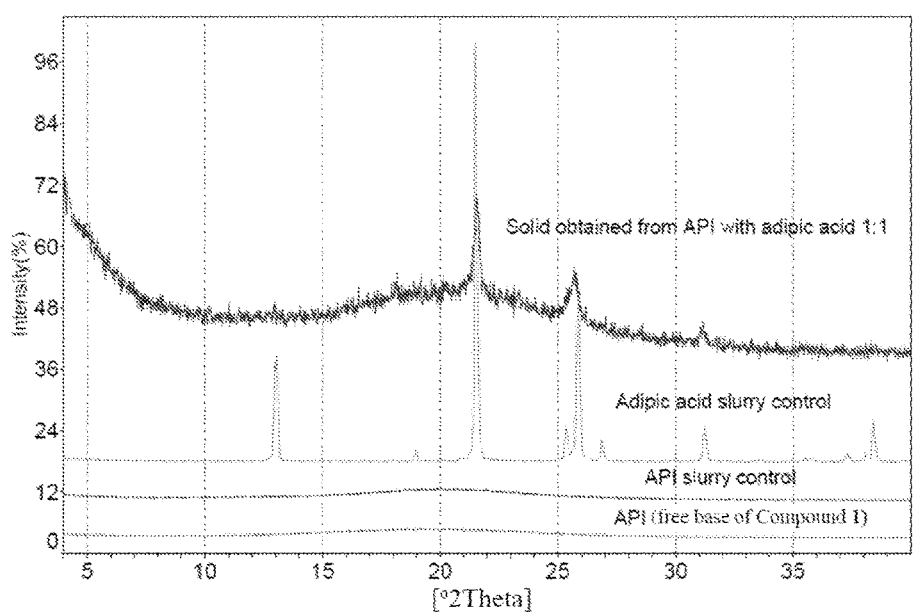
FIG. 12 shows overlay of X-ray diffraction patterns of solid obtained from Compound 1 with adipic acid (1:1), adipic acid slurry control, API slurry control and API.

The solids obtained from other salt-forming agents were all amorphous form (FIG. 8, FIG. 9, FIG. 10) or the same form with pure solid salt-forming agents (FIG. 11 and FIG. 12), suggesting free form or amorphous salts or the mixture of salt-forming agents with free form was obtained.

TABLE 16

Summary of formation of the salts of Compound 1 with various salt-forming agents

| | | | |
|---|---|---|---|
| Hydrochloric acid | 1:1 White suspension | No | Crystalline |
| Sulfuric acid | 1:1 Jelly like | No | Amorphous |
| Phosphoric acid | 1:1 White suspension | No | Amorphous |
| Methanesulfonic acid | 1:1 Jelly like | No | Crystalline |
| 2-hydroxyethane-sulfonic acid | 1:1 White suspension | No | Crystalline |
| Benzenesulfonic acid | 1:1 Jelly like | No | Amorphous |
| Glycolic acid | 1:1 White precipitation | Yes | Amorphous |
| L-lactic acid | 1:1 White precipitation | Yes | Amorphous |
| Fumaric acid | 1:1 White precipitation | Yes | Amorphous |
| L-tartaric acid | 1:1 Jelly like | No | Crystalline |
| Citric acid | 1:1 White precipitation | Yes | Amorphous |
| L-malic acid | 1:1 White precipitation | Yes | Amorphous |
| Succinic acid | 1:1 White precipitation | Yes | Amorphous |
| Hippuric acid | 1:1 No precipitation | Yes | Amorphous |
| Adipic acid | 1:1 White precipitation | Yes | Crystalline (Adipic acid) |
| Benzoic acid | 1:1 White precipitation | Yes | Amorphous |
| Gentisic acid | 1:1 White precipitation | Yes | Amorphous |
| Malonic acid | 1:1 White precipitation | Yes | Amorphous |
| Ethanedisulfonic acid | 1:1 White suspension | No | Amorphous |
| Toluenesulfonic acid | 1:1 Jelly like | No | Amorphous |
| Oxalic acid | 1:1 White suspension | No | Crystalline |
| Nicotinic acid | 1:1 White suspension | No | Crystalline (Nicotinic acid) |
| Nicotinamide | 1:1 White precipitation | Yes | Amorphous |
| Saccharin | 1:1 White precipitation | Yes | Amorphous |

Example 2: Preparation of Single Crystalline Form A** of Compound 1 Sesqui-Maleate A single crystal growth screening was conducted under 94 different conditions by varying solvent, temperature, and recrystallization methods, from which single crystals suitable for structure determination were obtained by slow cooling in acetone.

Example 3: Preparation of Crystalline Form A of Compound 1 Sesqui-Maleate

Figure 34:
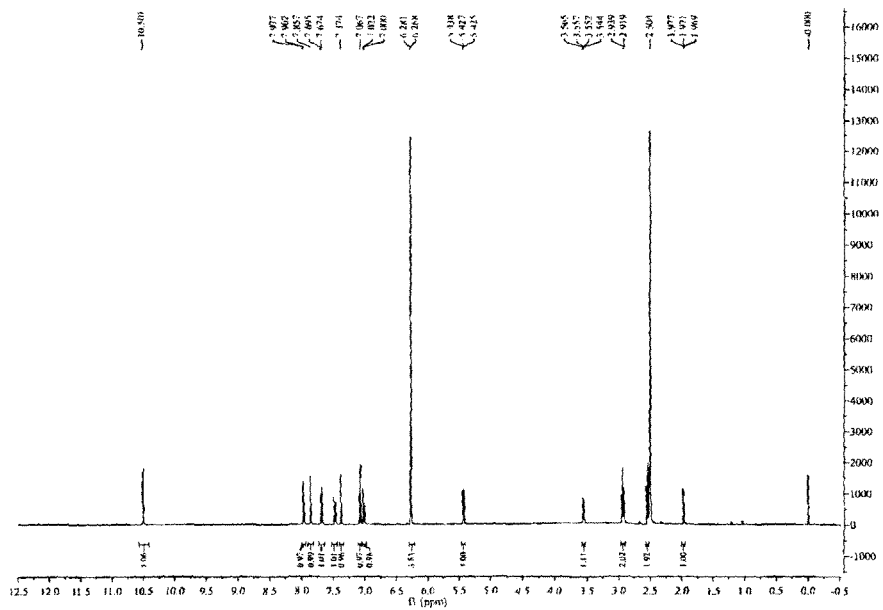
FIG. 34 shows a $^1$H-NMR spectrum of Crystalline Form A of Compound 1 Sesqui-Maleate.

The free base of Compound 1 (145 g) was combined with 63.5 g of maleic acid (1.8 equivalent) in 1750 mL of i-PrOH/$H_2O$ (V:V=4:1). The mixture was refluxed until all the solids were dissolved. The clear solution was cooled to rt, some crystal seeds were added, and then the mixture was let stand for 24 hrs. White solids were precipitated and filtered. The filter cake was washed with about 500 mL of i-PrOH/$H_2O$ (V:V=4:1) and dried under high vacuum at 50° C. for 48 hrs to give the title product (112 g) as crystalline crystals. A powder X-ray diffraction pattern method was used to characterize the structure of Crystalline Form A; see FIG. 17. TGA result indicated a weight loss of 0.3 wt % up to 120° C. DSC result showed a melting endotherm at 194.2° C. (onset temperature). $^1$H-NMR spectrum showed a stoichiometrical ratio of 1/1.5 of the free base/maleic acid (see FIG. 34).

Example 1A is directed to the mass production of the crystalline form of Compound 1 Sesqui-Maleate (i.e., designated as Form A*) and Example 3 is directed to laboratory preparation of the crystalline form of Compound 1 Sesqui-Maleate (i.e., designated as Form A). The powder X-ray diffraction pattern, $^1$H-NMR spectra, and other techniques show the consistency between the two crystalline forms of Crystalline Form A* and Crystalline Form A.

Example 4: Preparation of Crystalline Form B of Compound 1 Maleate

Figure 35:
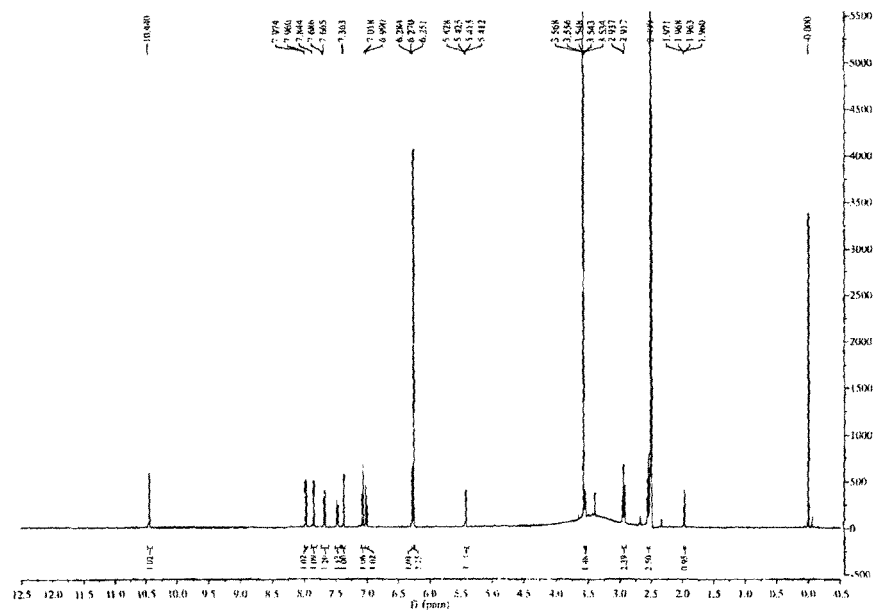
FIG. 35 shows a $^1$H-NMR spectrum of Crystalline Form B of Compound 1 maleate (1:1.2).

Crystalline Form B of Compound 1 maleate was prepared via cooling a 1,4-dioxane solution of Crystalline Form A of Sesqui-Maleate from 60° C. to 5° C. at a rate of 0.1° C./min for crystallization. Procedures: weigh 20.0 mg of Form A solids into a 3-mL glass vial, and add 1 mL of 1,4-dioxane into the vial; stir the mixture at 50° C. magnetically with a speed of 800 RPM; filter the sample after equilibrated at 60° C. for 2 hrs using 0.45 μm Nylon membrane; and cool the filtrate at a rate of 0.1° C./min from 60° C. to 5° C. The sample was stored at 5° C. before isolation. A powder X-ray diffraction pattern method was used to characterize the structure of Crystalline Form B; see FIG. 18. TGA result indicated a weight loss of 15.1 wt % up to 150° C. (contained molecules of crystal 1,4-dioxane solvate/hydrate). DSC result showed multiple overlapped endotherms (181.4 and 189.6° C.) before decomposition. $^1$H-NMR spectrum showed a stoichiometrical ratio of around 1/1.2 of the free base/maleic acid (see FIG. 35).

Example 5: Preparation of Crystalline Form C of Compound 1 Maleate

Figure 36:
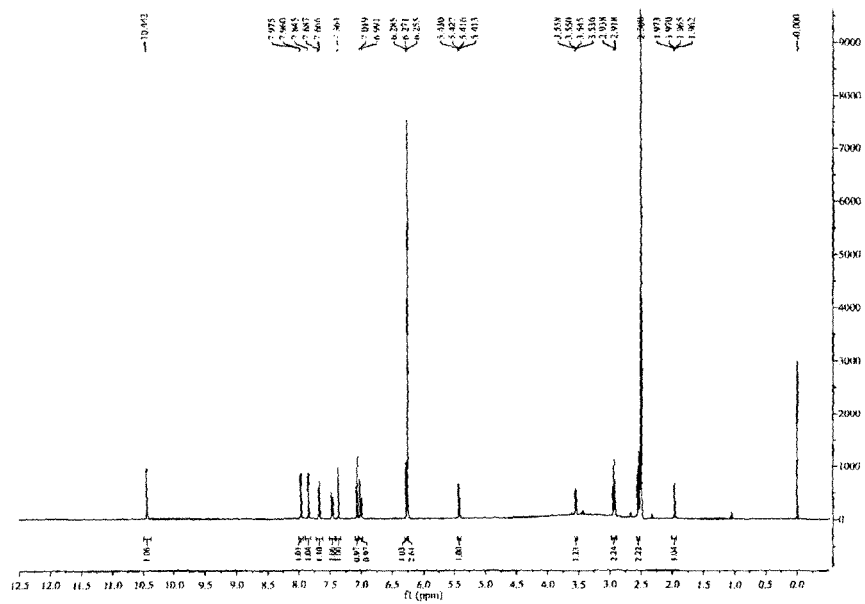
FIG. 36 shows a $^1$H-NMR spectrum of Crystalline Form C of Compound 1 maleate (1:1.3).

Crystalline Form C of Compound 1 maleate was prepared via cooling an ethanol solution of Compound 1 from 60° C. to 5° C. at a rate of 0.1° C./min for crystallization. Procedures: weigh 21.3 mg of Form A solids into a 3-mL glass vial, and add 1 mL of ethanol to the vial; stir the mixture at 50° C. magnetically with a speed of 800 RPM; filter the sample after equilibrated at 60° C. for 2 hrs using 0.45 μm Nylon membrane; and cool the filtrate at a rate of 0.1° C./min from 60° C. to 5° C. The sample was stored at 5° C. before isolation. A powder X-ray diffraction pattern method was used to characterize the structure of Crystalline Form C; see FIG. 19. TGA result indicated a weight loss of 7.0 wt % up to 180° C. (contained molecules of crystal hydrate). DSC result showed four endotherms (107.5, 162.7, 179.3 and 196.0° C.) before decomposition. ¹H-NMR spectrum showed a stoichiometrical ratio of around 1/1.3 of the free base/maleic acid (see FIG. 36).

Example 6: Preparation of Crystalline Form D of Compound 1 Maleate

Figure 37:
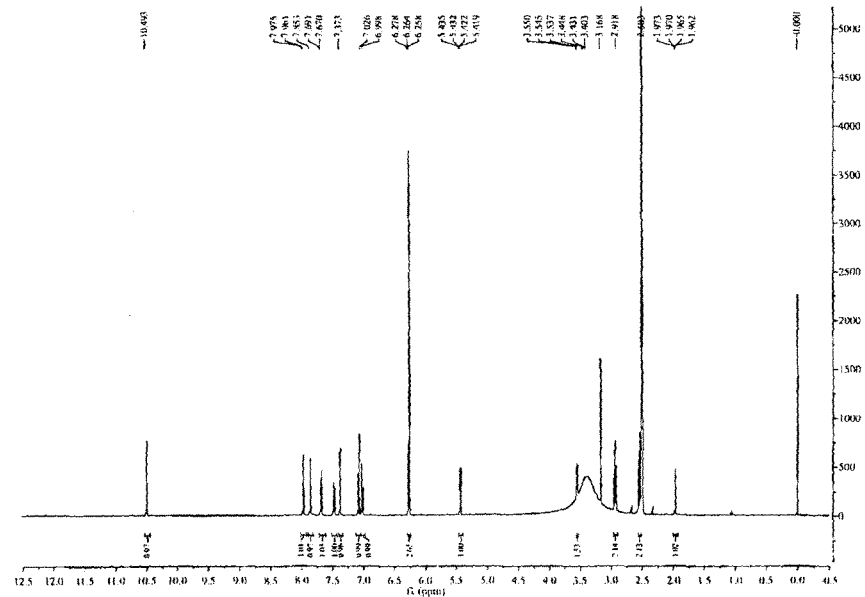
FIG. 37 shows a $^1$H-NMR spectrum of Crystalline Form D of Compound 1 maleate (1.1).

Crystalline Form D of Compound 1 Maleate was prepared via slow evaporation of MeOH solution of Crystalline Form A of Compound 1 Sesqui-Maleate in the presence of [dmin] $CF_3COO$ ionic liquid at RT. Procedures: weigh 150.2 mg of Form A solids into a 20-mL glass vial, and add 10.2 mL of MeOH into the vial; filter the mixture to get a saturated stoke solution using 0.45 μm Nylon membrane; add 2.8 mg of [dmin]$CF_3COO$ ionic liquid into the 1-mL MeOH stock solution; and stir at RT to induce precipitation. A powder X-ray diffraction pattern method was used to characterize the structure of Crystalline Form D; see FIG. 20. TGA result indicated a weight loss of 6.3 wt % up to 120° C. (contained molecules of crystal hydrate). DSC result showed two endotherms (75.8 and 161.4° C.) before decomposition. ¹H-NMR spectrum showed a stoichiometrical ratio of around 1/1 of the free base/maleic acid (see FIG. 37).

Example 7: Preparation of Crystalline Form F of Compound 1 Maleate

Crystalline Form F of Compound 1 Maleate was prepared via crystallization of Crystalline Form A of Compound 1 Sesqui-Maleate from an ACN/$H_2O$ (1:1, v/v) solution. Procedures: weigh 18.9 mg of Form A solids into a 3-mL glass vial, and add 1.5 mL of ACN/$H_2O$ (1:1, v/v); and add about 2 mg of polymer mixture (polyvinyl pyrrolidone (PVP), polyvinyl alcohol (PVA), polyvinylchloride (PVC), polyvinyl acetate (PVAC), hypromellose (HPMC), and methyl cellulose (MC) in a mass ratio of 1:1:1:1:1:1) into the suspension and stir at RT to induce precipitation.

Figure 38:
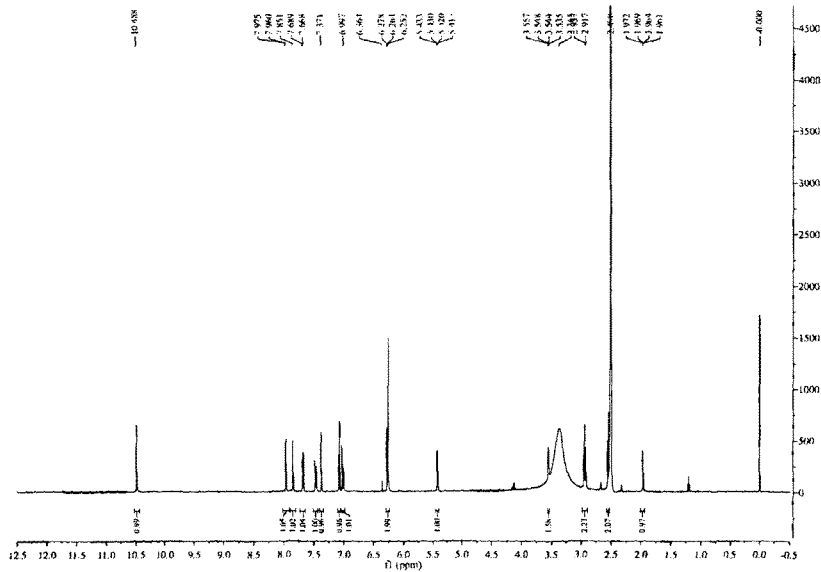
FIG. 38 shows a $^1$H-NMR spectrum of Crystalline Form F of Compound 1 maleate (1:0.5).

A powder X-ray diffraction pattern method was used to characterize the structure of Crystalline Form F; see FIG. 21. TGA result indicated a weight loss of 3.2 wt % up to 130° C. (contained molecules of ACN solvate/hydrate). DSC result showed three endotherms (62.4, 156.9 and 169.3° C.) before decomposition. ¹H-NMR spectrum showed a stoichiometrical ratio of around 1/0.5 of the free base/maleic acid (see FIG. 38).

Example 8: Preparation of Crystalline Form G of Compound 1 Maleate

Crystalline Form G of Compound 1 maleate was prepared via adding water into acetic acid solution of Crystalline Form A of Compound 1 Sesqui-Maleate. Procedures: weigh 20.2 mg of Form A solids into a 20-mL glass vial; add 1.0 mL of acetic acid into the vial and stir at RT to get a clear solution; and add 5 mL of water into the solution stepwise to induce precipitation.

Figure 39:
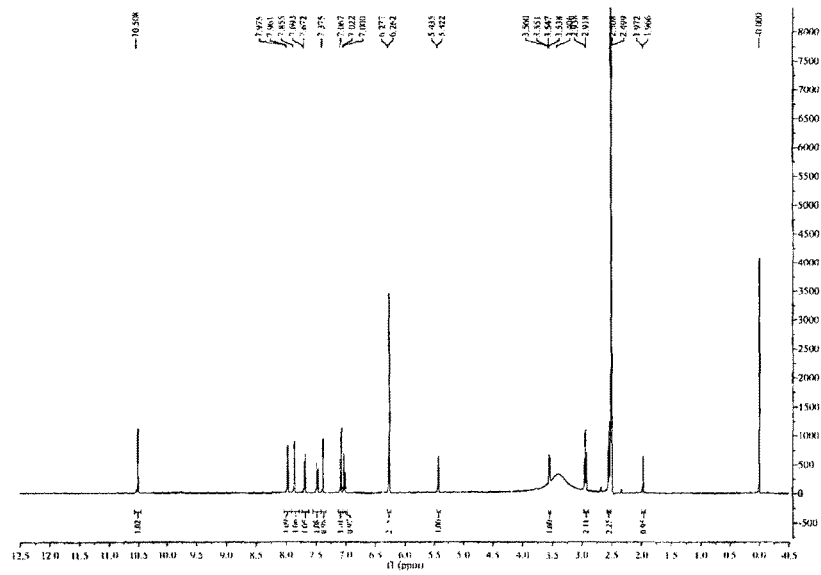
FIG. 39 shows a $^1$H-NMR spectrum of Crystalline Form G of Compound 1 maleate (1:0.5).

A powder X-ray diffraction pattern method was used to characterize the structure of Crystalline Form G; see FIG. 22. TGA result indicated a weight loss of 11.0 wt % up to 120° C. (contained molecules of crystal hydrate). DSC result showed four endotherms (84.3, 126.9, 139.4 and 187.3° C.) before decomposition. ¹H-NMR spectrum showed a stoichiometrical ratio of around 1/0.5 of the free base/maleic acid (see FIG. 39).

Example 9: Preparation of Crystalline Form H of Compound 1 Maleate

Figure 40:
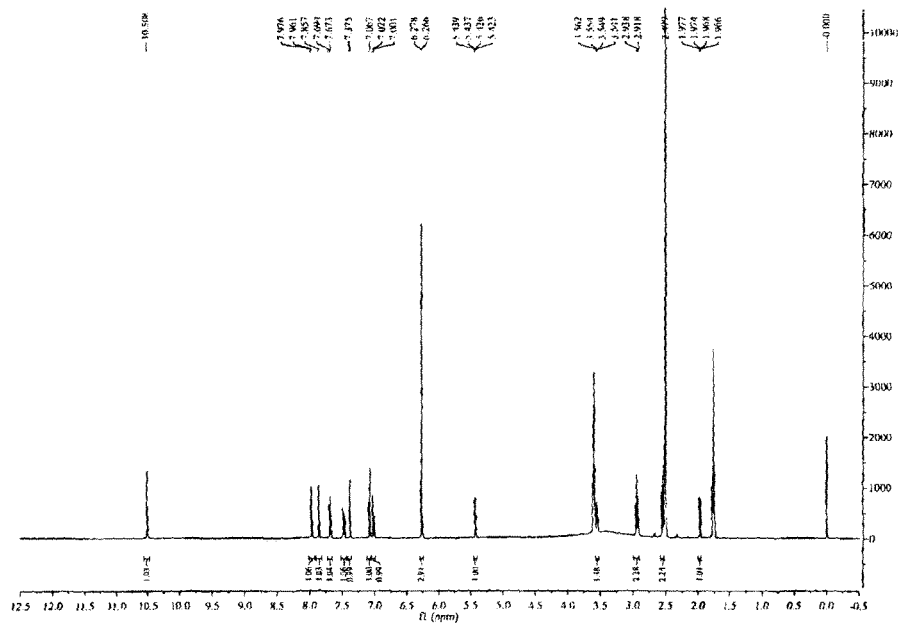
FIG. 40 shows a $^1$H-NMR spectrum of Crystalline Form H of Compound 1 maleate (1:1).

Crystalline Form H of Compound 1 maleate was prepared via slurrying Crystalline Form A of Compound 1 Sesqui-Maleate in THF at RT. Procedures: weigh 17.7 mg of Form A solids into a 1.5-mL vial, and add 0.3 mL of THF into the vial to get a suspension; and stir the mixture at RT magnetically with a speed of 800 RPM for 3 days. A powder X-ray diffraction pattern method was used to characterize the structure of Crystalline Form H; see FIG. 23. TGA result indicated a two step weight loss of 13.0 wt % up to 150° C. (contained molecules of crystal THF solvate/hydrate). DSC result showed 2 endotherms (124.5 and 178.0° C.) before decomposition. ¹H-NMR spectrum showed a stoichiometrical ratio of around 1/1 of the free base/maleic acid (see FIG. 40).

Example 10: Preparation of Crystalline Form I of Compound 1 Maleate

Figure 41:
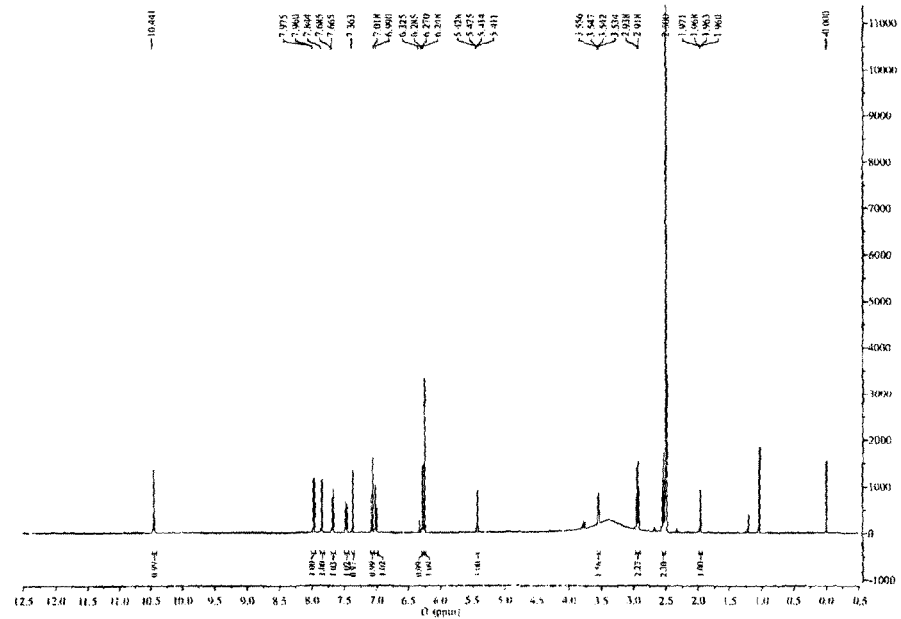
FIG. 41 shows a $^1$H-NMR spectrum of Crystalline Form I of Compound 1 maleate (1:0.5).

Crystalline Form I of Compound 1 maleate was prepared via slow evaporation of an IPA/$H_2O$ (3:1, v/v) solution of Crystalline Form A of Compound 1 Sesqui-Maleate at RT. Procedures: weigh 13.8 mg of Form A solids into a 3-mL glass vial, and add 1.5 mL of IPA/$H_2O$ (3:1, v/v) into the vial to obtain a clear solution; evaporate solvent from the solution at RT to induce precipitation. A powder X-ray diffraction pattern method was used to characterize the structure of Crystalline Form I; see FIG. 24. TGA result indicated a two step weight loss of 20.7 wt % up to 180° C. (contained molecules of crystal IPA solvate/hydrate). DSC result showed four overlapped endotherms (85.8, 115.1 and 138.2° C.) before decomposition. ¹H-NMR spectrum showed a stoichiometrical ratio of around 1/0.5 of the free base/maleic acid (see FIG. 41).

Example 11: Preparation of Crystalline Form J of Compound 1 Maleate

Figure 42:
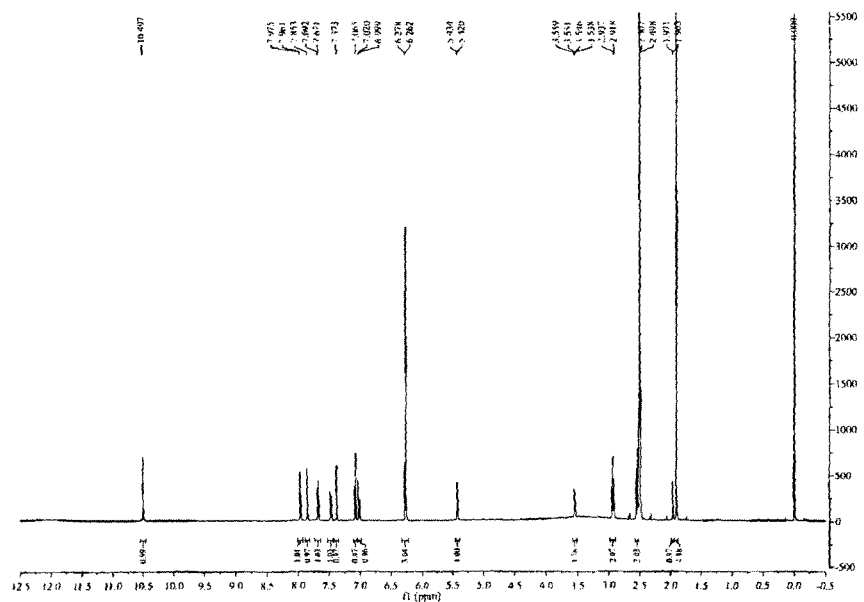
FIG. 42 shows a $^1$H-NMR spectrum of Crystalline Form J of Compound 1 maleate (1:1).

Crystalline Form J of Compound 1 maleate was prepared via interaction between the solids of Crystalline Form A of Compound 1 maleate and acetic acid vapor. Procedures: weigh 14.2 mg of Form A solids into a 3-mL glass vial; seal the 3-mL vial into a 20-mL glass vial containing 2 mL of acetic acid; and keep the system at RT for 8 days, allowing the vapor to interact with solids. A powder X-ray diffraction pattern method was used to characterize the structure of Crystalline Form J; see FIG. 25. TGA result indicated a weight loss of 19.3 wt % up to 130° C. (contained molecules of crystal acetic acid solvate/hydrate). DSC result showed three endotherms (102.9, 155.7 and 187.7° C.) before decomposition. ¹H-NMR spectrum showed a stoichiometrical ratio of around 1/1 of the free base/maleic acid (see FIG. 42).

Example 12: Preparation of Crystalline Form K of Compound 1 Maleate

Figure 43:
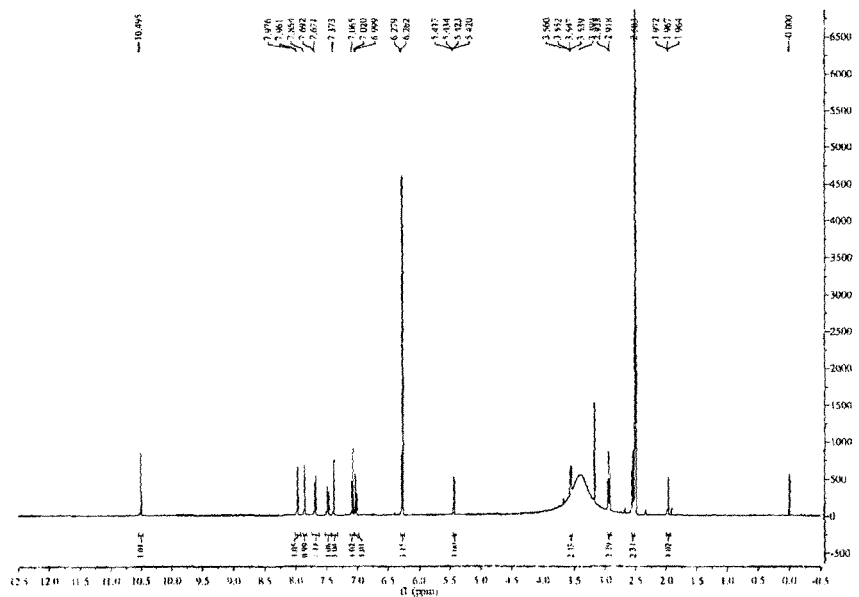
FIG. 43 shows a $^1$H-NMR spectrum of Crystalline Form K of Compound 1 maleate (1:1).

Crystalline Form K of Compound 1 maleate was obtained after storage of Crystalline Form D of Compound 1 Maleate at ambient condition for two weeks. A powder X-ray diffraction pattern method was used to characterize the structure of Crystalline Form K; see FIG. 26. TGA result indicated a weight loss of 4.2 wt % up to 150° C. (contained molecules of crystal hydrate). DSC result showed two endotherms (59.6 and 163.5° C.) before melting at 186.6° C. (peak temperature). ¹H-NMR spectrum showed a stoichiometrical ratio of around 1/1 of the free base/maleic acid (see FIG. 43).

Example 13: Preparation of Crystalline Form L of Compound 1 Maleate

Figure 44:
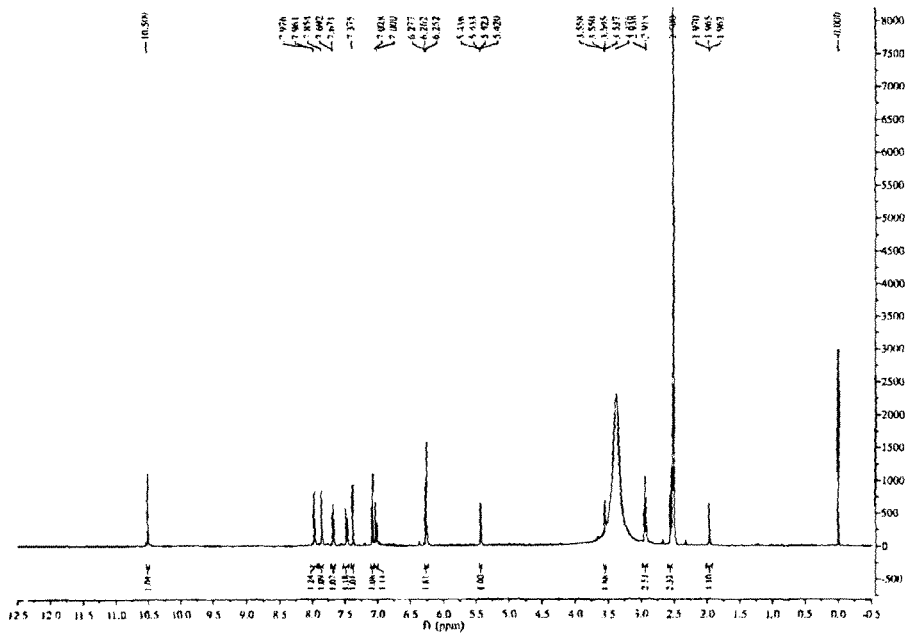
FIG. 44 shows a $^1$H-NMR spectrum of Crystalline Form L of Compound 1 maleate (1:0.3).

Crystalline Form L of Compound 1 Maleate was obtained via heating Crystalline Form G of Compound 1 maleate to 140° C. and cooling to RT. A powder X-ray diffraction pattern method was used to characterize the structure of Crystalline Form L; see FIG. 27. TGA result indicated a weight loss of 3.9 wt % up to 120° C. (contained molecules of crystal hydrate). DSC result showed one endotherm (141.1° C., onset temperature) before melting at 183.9° C. (peak temperature). $^1$H-NMR spectrum showed a stoichiometrical ratio of around 1/0.3 of the free base/maleic acid (see FIG. 44).

Example 14: Preparation of Crystalline Form M of Compound 1 Maleate

Figure 45:
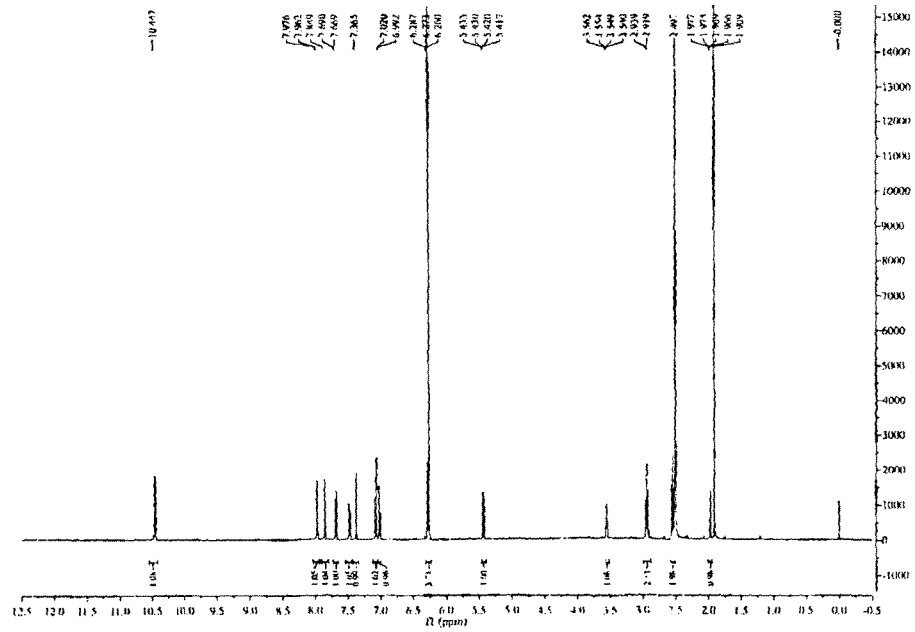
FIG. 45 shows a $^1$H-NMR spectrum of Crystalline Form M of Compound 1 maleate (1.1.3).

Crystalline Form M of Compound 1 maleate was obtained after storage of Crystalline Form J of Compound 1 maleate at ambient condition for two weeks. A powder X-ray diffraction pattern method was used to characterize the structure of Crystalline Form L; see FIG. 28. TGA result indicated a weight loss of 1.4 wt % up to 140° C. (contained molecules of crystal acetic acid hydrate/hydrate). DSC result showed multiple endotherms (123.0, 156.5, 171.9, 176.1 and 195.3° C.). $^1$H-NMR spectrum showed a stoichiometrical ratio of around 1/1.3 of the free base/maleic acid (see FIG. 45).

Example 15: Screening of Conditions for Formation of Compound 1 Maleate and Sesqui-Maleate

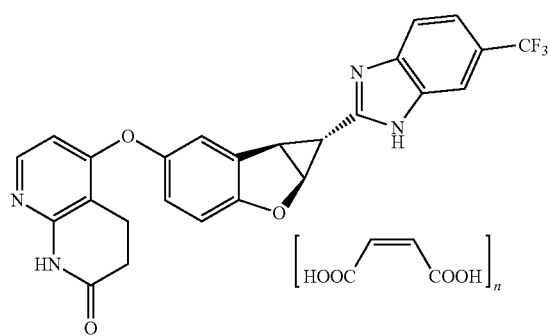

Condition 1: Compound 1 Reacted with Maleic Acid in EtOAc.

To a stirred solution of Compound 1 (47.8 mg) in EtOAc (5 mL) was added a solution of Maleic acid in EtOAc (0.2 mol/L, v mL) at rt. The mixture was stirred for 30 min. The solid was filtered and dried under high vacuum to give the title salt. Surprisingly, when 0.5, 0.9, 1.8, or 3.0 eq. of malic acid was used, a crystalline Compound 1 Sesqui-Maleate (1:1.5) salt was obtained under all the conditions.

Condition 2: Compound 1 Reacted with Maleic Acid in EtOH.

Procedure: A mixture of Compound 1 and maleic acid in EtOH was refluxed for 20 min until all solids dissolved. The solution was cooled to ambient temperature and stand for 3 hours. A white solid precipitated out, and was filtered and dried under high vacuum to give the title compound. It was surprisingly discovered that when one equivalent of malic acid was used, a crystalline Compound 1 maleate (1:1) salt was obtained; but when the amount of malic acid was increased to 1.3, 1.5, or 3.5 eq., all the conditions gave a crystalline Compound 1 Sesqui-Maleate (1:1.5) salt as the product.

Condition 3: Compound 1 Reacted with Maleic Acid in MeOH.

Procedure: A mixture of Compound 1 and maleic acid in MeOH was refluxed for 20 min until all the solids dissolved. The solution was cooled to ambient temperature and let stand for 3 hours. A white solid precipitated out, and was filtered and dried under high vacuum to give a Compound 1 maleate (1:1) salt. Surprisingly, using MeOH as solvent, when 1.0, 1.5, or 3.5 eq. of maleic acid was used, the product was consistently a powdery Compound 1 maleate (1:1) salt.

Condition 4: Compound 1 Reacted with Maleic Acid in i-PrOH/Water.

Procedure: A mixture of Compound 1 (145 g, 0.3 mol) and maleic acid (63 g, 0.54 mol) in a mixed solvent (i-PrOH:H$_2$O=4:1 by volume, 1.7 L) was refluxed until all the solid was dissolved. The mixture was allowed to cool to room temperature, some crystal seeds were added to the solution, and the mixture was let stand for 24 hours. A white crystal precipitated out and was filtered. The filter cake was washed with 500 mL of the mixed solvent, dried under high vacuum at 50° C. for 48 hours to give Compound 1 Sesqui-Maleate Salt (112 g, 56.7%) as crystalline needles. Interestingly, when 40 vol % i-PrOH was used as solvent, a crystalline Compound 1 hemi-maleate (1:0.5) salt was obtained; whereas when 60 vol % i-PrOH, 90 vol % i-PrOH, or 100% i-PrOH was used as solvent, all the conditions gave a crystalline Compound 1 Sesqui-Maleate (1:1.5) salt.

Condition 5: Compound 1 Reacted with Maleic Acid in Other Solvents.

When other solvents (THF, Acetone, DME, 1,4-dioxane) were used, according to similar procedures described above, the product obtained was consistently a Compound 1 Sesqui-Maleate (1:1.5) salt.

Condition 6: Conversion of Compound 1 Sesqui-Maleate Salt (1:1.5) into the Maleate Salt (1:1).

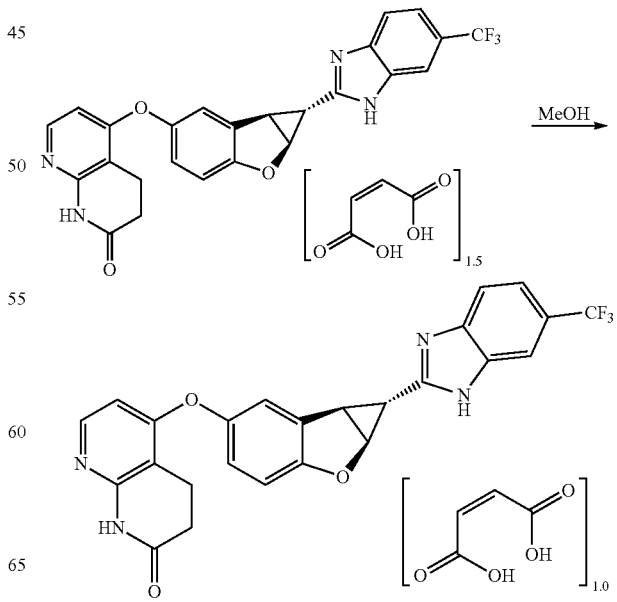

Figure 32:
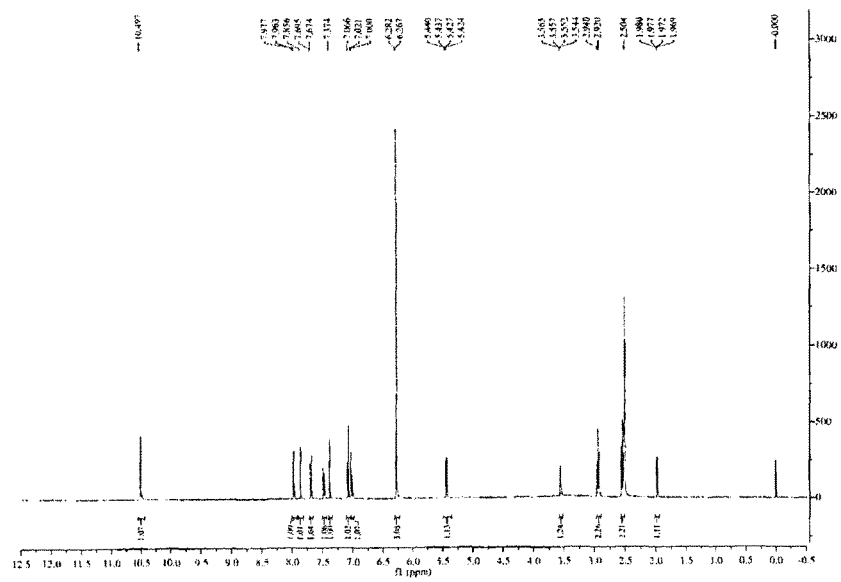
FIG. 32 shows a $^1$H-NMR spectrum of Crystalline Form N of Compound 1 maleate Salt (1:1).

A crystal of Compound 1 Sesqui-Maleate Salt (1.0 g, 1.53 mmol) was suspended in MeOH (20 mL) and the mixture was stirred at rt for 1 day. The white solid was filtered. The filter cake was washed with MeOH (10 mL), and dried under infra red lamp at 50° C. for 16 hrs to give Compound 1 maleate Salt (1:1) (820 mg, 90%) as a white crystalline solid. $^1$H NMR (400 MHz, dmso) δ 10.50 (s, 1H), 7.97 (d, J=5.6 Hz, 1H), 7.86 (s, 1H), 7.68 (d, J=8.4 Hz, 1H), 7.47 (dd, J=8.4, 1.2 Hz, 1H), 7.38 (d, J=2.4 Hz, 1H), 7.08 (d, J=8.8 Hz, 1H), 7.01 (dd, J=8.8, 2.4 Hz, 1H), 6.31-6.24 (m, 3H), 5.43 (dd, J=5.2, 1.2 Hz, 1H), 3.55 (dd, J=5.2, 3.2 Hz, 1H), 2.94 (t, J=7.6 Hz, 2H), 2.54 (t, J=7.6 Hz, 2H), 1.97 (dd, J=3.2, 1.2 Hz, 1H) (detailed spectrum see FIG. 32).

A powder X-ray diffraction pattern study was used to determine the structure the resultant white crystalline solid under Condition 6 and named as Compound 1 maleate (1:1) Crystalline Form N. (FIG. 33)

Condition 7: Conversion of Compound 1 Maleate Salt (1:1) into the Sesqui-Maleate Salt.

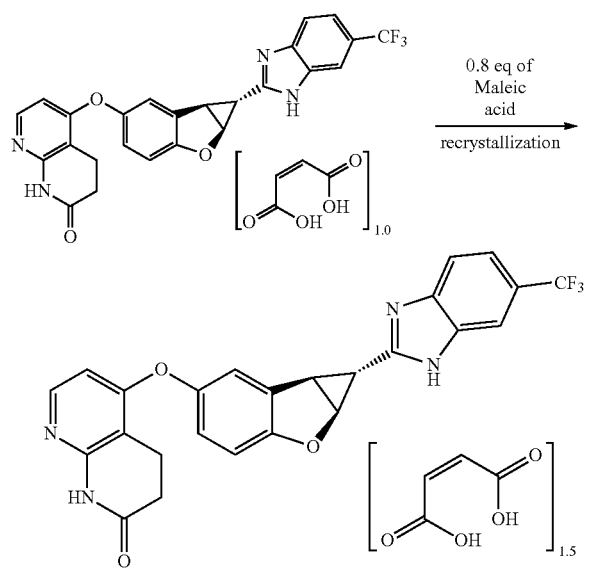

A mixture of Compound 1 maleate salt (1:1) (4.3 g) and maleic acid (0.67 g, 0.8 eq of maleic acid) in a mixture of i-PrOH/H$_2$O (4:1, v/v, 50 mL) was refluxed for 1 hour. A small amount of solid remained. Another 5 mL of the mixed solvent was added and the resulted mixture was refluxed for 30 minutes, and all the solids dissolved. The mixture was allowed to cool to rt and was then let stand for 16 hours. A white crystal precipitated out and was filtered. The filter cake was washed with 20 mL of the mixed solvent, dried under infrared lamp for 24 hours to give the Compound 1 Sesqui-Maleate (3.2 g, 68%) salt as crystalline needles.

Example 16

Impurity expulsion of Compound 1 API: 28.5 Kg of the 1$^{st}$ crystallized sesqui-maleate (chemical purity=98.82%) was stirred with methanol at 45-50° C. for 4-5 h. The slurry mixture was then cooled at 20-30° C. for 3-4 h, filtered to give a wet cake (30.3 Kg; chemical purity=99.76%). The wet cake was mixed with ethyl acetate and water, treated with aqueous sodium carbonate to pH=7-8 and then washed with water. The free base of Compound 1 (16.2 Kg, chemical purity=99.81%) in ethyl acetate was obtained. Ethyl acetate was replaced by i-propanol through distillation. The free base in i-PrOH was stirred with aqueous solution of maleic acid and crystal seeds of the sesqui-maleate. The mixture was stirred at 40-50° C. for a few hours and at 20-30° C. for a few hours. The resulting solid was filtered to give the 2$^{nd}$ crystallized sesqui-maleate salt (19.6 Kg; Chemical Purity=99.82%; optical purity=100%).

Example 17: Stability Study of Salts or Crystalline Forms of Compound 1

Example 17A: Short-Term Stability Study

A short term stability study was conducted to evaluate the HCl salt, mesylate salt, 2-hydroxyethensulfonate salt and maleate salt.

Weighed about 2 mg (For XRPD: 10 mg) of each of the above salts in a 40 mL glass vial, separately. The free base form was used as control. The closed samples were capped and sealed with parafilm, while the opened samples were covered by aluminum foil with pinhole. All the samples were stored in stability chamber or dry oven at the corresponding conditions (60° C. and 40° C./75% RH) for 1 week.

The HCl salt appeared to be light yellow powder at both conditions after 1 week, the appearance of 2-hydroxyethanesulfonate mesylate and maleate had no change with visual observation. The XRPD results showed that no crystal form transformation was detected for all salt samples.

The chemical stability results were summarized in Table 17. Variable degradation was detected with the increase of TRS (HCl salt>2-hydroxyethensulfonate>mesylate>maleate>free base). By contrast, temperature stress condition might have greater impact than humidity stress condition for salt formation of Compound 1, since transmission Raman spectroscopy (TRS) of salt samples increased more at 60° C.

TABLE 17

Summary of short-term stability study

| Salt Sample | TRS % | | |
|---|---|---|---|
| | 0 day | 60° C. | 40° C./75% RH |
| API free base | 0.12 | 0.12 | 0.11 |
| HCl salt | 0.66 | 8.76 | 2.76 |
| 2-hydroxyethanesulfonate | 0.08 | 1.16 | 0.51 |
| Mesylate | 0.11 | 0.55 | 0.14 |
| Crystalline Form A* of Compound 1 Sesqui-Maleate | 0.08 | 0.17 | 0.10 |

Example 17B: Long-Term Stability Study

The long-term stability studies of Crystalline Form A* of Compound 1 Sesqui-Maleate showed there was no significant chemical purity change occurred when stored at 25° C.° C./60% RH for up to 18 months (Assay w/w: T0=99.1% and T18=98.8%) and at 40° C./75% RH condition for up to 6 months (Assay w/w: T0=99.1% and T6=98.9%). The results even showed that Crystalline Form A* of Compound 1 Sesqui-Maleate still kept the purity of 98.5% after 24 month stability study at 25 C/75% RH. In addition, no crystal form and optical purity changes were observed when stored at 25° C.° C./60% RH for up to 18 months and at 40° C./75% RH condition for up to 6 months.

Efficacy Tests
Test 1: Inhibition and Selectivity of the Kinases by Compound 1 Sesqui-Maleate (Crystalline Form A* Tested)
Methods:
Raf Kinase Enzymatic Assays:

Crystalline Form A* of Compound 1 Sesqui-Maleate was tested against recombinant B-Raf (V600E) (PV3849), C-Raf (Y340D/Y341D) (PV3805) and wild-type Braf (PV3848) from Life Technologies in kinase activity assays based on homogeneous time-resolved fluorescence (HTRF) methodology (Cisbio Bioassays). The assays were carried out in a reaction mixture containing RAF kinases, ATP at KM concentration, GST-tagged MEK1 (K97R) and Crystalline Form A* of Compound 1 Sesqui-Maleate or DMSO in buffer containing 25 mM Tris pH7.4, 10 mM $MgCl_2$, 0.5 mM EGTA, 0.5 mM $Na_3VO_4$, 5 mM beta-glycerophosphate, 0.01% Triton X-100, 2.5 mM DTT and 0.1% BSA. The kinase was incubated with Crystalline Form A* of Compound 1 Sesqui-Maleate for 1 hr at room temperature (RT) and the reaction was initiated by the addition of ATP and GST-MEK1 (Full-length protein with K97R mutation, recombinant protein purified from bacterial expression system). After reaction at RT for 1 hr, stop/detection solution was added according to the manufacture's instruction (Cisbio Bioassays). The stop/detection solution contained Eu3+ cryptate-conjugated anti-phospho MEK1/2 (Ser217/221) rabbit polyclonal antibody and d2-conjugated anti-GST mouse monoclonal antibody in buffer containing 25 mM Tris pH7.4, 400 mM KF, 50 mM EDTA, 0.1% BSA and 0.01% Triton X-100. The TR-FRET signals (ratio of fluorescence emission at 665 nm over emission at 620 nm with excitation at 337 nm wavelength) were measured on a PHERAstar FS plate reader (BMG Labtech) after 1.5 hr incubation. Phosphorylation of MEK1 led to the binding of anti-phospho-MEK1/2 antibody to GST-MEK1 protein that place fluorescent donor (Eu3+ crypate) in close proximity to the accepter d2 on the anti-GST antibody, thus resulting in a high degree of fluorescence resonance energy transfer from the donor fluorophore (at 620 nm) to the acceptor fluorophore (at 665 nm). The IC50 for Crystalline Form A* of Compound 1 Sesqui-Maleate was derived from fitting the dose-response % inhibition data to the four-parameter logistic model by Graphpad Prism software.

Kinase Assays for EGFR, EPHA2, PDGFR-Beta, TXK, FLT3, VEGFR2, RET, BTK, ITK, TEC and SRC Crystalline Form A* of Compound 1 Sesqui-Maleate was tested against recombinant EGFR/EPHA2/BTK (from Carna Biosciences), ITK/TEC/SRC/PDGFR-beta/TXK/FLT3/VEGFR2/RET (from Life Technologies), and HER2 (aa676-1255, recombinant protein purified from insect expression system) in HTRF KinEASE-TK assay from Cisbio Bioassays according to the manufacturer's instructions. The assay was carried out in a reaction mixture containing kinases, ATP at KM concentration, biotinylated peptide substrate (61TK0BLC, Cisbio Bioassays) and Crystalline Form A* of Compound 1 Sesqui-Maleate. The kinase was incubated with Crystalline Form A* of Compound 1 Sesqui-Maleate at RT for 1 hr or 2 hr (for EGFR) and the reaction was initiated by the addition of ATP and substrate. After reaction, stop/detection solution was added according to the manufacture's instruction. The stop/detection solution contained Eu+ cryptate conjugated antiphosphotyrosine antibody (61T66kLB, CisBio Bioassays) and Streptavidin-XL665 (610SAXLB, CisBio Bioassays) in buffer containing 25 mM Tris pH7.4, 400 mM KF, 50 mM EDTA, 0.01% BSA, 0.01% Triton X-100. The TR-FRET signals (ratio of fluorescence emission at 665 nm over emission at 620 nm with excitation at 337 nm wavelength) were recorded on a PHERAstar FS plate reader (BMG Labtech) after 1 hr incubation. Phosphorylation of biotinylated peptide substrate led to the binding of both Eu+ cryptate conjugated antiphosphotyrosine antibody and streptaviding-XL665 to the biotinylated peptide. The close proximity of the donor (Eu+ cryptate) and acceptor (XL665) fluorophore led to a high degree of fluorescence resonance energy transfer from the donor fluorophore (at 620 nm) to the acceptor fluorophore (at 665 nm). The $IC_{50}$ for Crystalline Form A* of Compound 1 Sesqui-Maleate was derived from fitting the dose-response % inhibition data to the four-parameter logistic model by Graphpad Prism software.

Results:

Compound 1 Sesqui-Maleate (Crystalline Form A*) is a potent and reversible inhibitor of V600E mutant B-RAF, wild-type B-RAF, and C-RAF enzymes. In addition, among the following kinases that have been tested thus far, Compound 1 Sesqui-Maleate potently inhibits EGFR, EPHA2, PDGFR-beta, FLT3, VEGFR2 and RET, has weak inhibition for HER2, SRC and TXK and no inhibition for BTK, ITK and TEC. Many of these kinases that Compound 1 Sesqui-Maleate inhibits have been identified as potential targets for anticancer therapy and as such may increase the potential efficacy, as well as the potential applicability of Compound 1 Sesqui-Maleate to a wide range of tumors

TABLE 18

Enzymatic Inhibition Activities of Crystalline Form A* of Compound 1 Sesqui-Maleate.

| Enzyme | IC50 (nM) | Enzyme | IC50 (nM) |
| --- | --- | --- | --- |
| BRAF V600E (416-766) | 26 | TEC | >10000 |
| CRAF Y340, 341D | 3.5 | HER2 | 2573 |
| WT-BRAF | 69 | SRC | 917 |
| WT-EGFR | 44 | PDGFR-beta | 17 |
| EPHA2 | 61 | BTK | >10,000 |
| ITK | >10,000 | TXK | 4800 |
| FLT3 | 25 | RET | 18 |
| VEGFR2 | 22 | | |

Test 2: In Vitro Growth Inhibition of Human Tumor Cell Lines by Compound 1 Sesqui-Maleate (Crystalline Form A* Tested)
Methods:

A375, Sk-Mel-28, HT29, Colo205, A431, and HCC827 cell lines were purchased from American Type Culture Collection. All the cell lines used in the cellular assays were cultured in the designated medium supplemented with 10% fetal bovine serum (FBS, Thermo Scientific), 100 units/mL penicillin (Gibco), 0.1 mg/mL streptomycin (Gibco) and in a humidified 37° C. environment with 5% $CO_2$. Cell lines were reinstated from frozen stocks laid down within three passages from the original cells purchased and passaged no more than 30 times.

Cellular phospho-ERK and phospho-EGFR were measured using a TR-FRET-based method. Cells were seeded at $3\times10^4$ per well of a 96-well plate and left to attach for 16 hours. Growth medium was then replaced with 100 μL of medium containing no serum. Cells were then treated with a 10-point titration of compound. After 1 h of compound treatment, 50 μL of lysis buffer (Cisbio) were added to each well. Plates were then incubated at room temperature with shaking for 30 min. A total of 16 μL of cell lysate from each well of a 96-well plate was transferred to a 384-well small volume white plate. Lysate from each well was incubated with 2 μL of Eu3+- or Tb3+-cryptate (donor) labeled anti- ERK or anti-EGFR antibody (Cisbio) and 2 μL of D2 (acceptor) labeled anti-phospho-ERK or anti-phospho-EGFR antibody (Cisbio) for 2 h at room temperature. FRET signals were measured using a PHERAstar FS reader (BMG Labtech). $IC_{50}$ values for ERK or EGFR phosphorylation was determined using GraphPad Prism software.

The growth-inhibitory activity of compounds in a panel of melanoma, colon, breast and lung cancer cells was determined using CellTiter-Glo luminescent cell viability assay (Promega). The number of cells seeded per well of a 96-well plate was optimized for each cell line to ensure logarithmic growth over the 3 days treatment period. Cells were left to attach for 16 hours and then treated with a 10-point dilution series in duplicate. Following a 3-day exposure to the compound, a volume of CellTiter-Glo reagent equal to the volume of cell culture medium present in each well was added. Mixture was placed on an orbital shaker for 2 minutes to allow cell lysing, followed by 10 minutes incubation at room temperature to allow development and stabilization of luminescent signal. Luminescent signal was measured using PHERAstar FS reader (BMG Labtech). $EC_{50}$ values for cell viability were determined with GraphPad Prism software.

Results:

Cellular assays have confirmed that Compound 1 Sesqui-Maleate inhibits a number of direct signaling intermediates downstream of RAFs. For example, Compound 1 Sesqui-Maleate inhibited ERK phosphorylation with an $IC_{50}$ of 32 and 77 nM in B-RAF V600E mutant driven melanoma A375 and Sk-Mel-28 cells. It also inhibits ERK phosphorylation with an $IC_{50}$ of 103 and 53 nM in B-RAF V600E mutant driven HT29 and Colo205 colorectal cancer cells. Additionally, Compound 1 Sesqui-Maleate inhibits EGFR phosphorylation with an $IC_{50}$ of 385 and 161 nM in EGFR overexpressing A431 and EGFR mutant HCC827 lung cancer cell lines. Compound 1 Sesqui-Maleate has been assessed for its anti-proliferation activity in a panel of cancer cell lines. It showed antiproliferative activity against a number of cell lines harboring B-RAF mutation (Table 19).

TABLE 19

Crystalline Form A* of Compound 1 Sesqui-Maleate inhibited BRAF V600E-driven cell proliferation.

| Cell line | BRAF status | Compound 1 $EC_{50}$ (mean ± SD) | N |
|---|---|---|---|
| A375 | V600E | 137 ± 0.5 | 2 |
| Sk-Mel-28 | V600E | 251 ± 54 | 2 |
| HT-29 | V600E | 138 ± 13 | 2 |
| Colo-205 | V600E | 147 ± 0.6 | 2 |

Test 3: In Vivo Pharmacology of Crystalline Form A* of Compound 1 Sesqui-Maleate Tumor Transplantation Methods:

Human cancer cells were inoculated subcutaneously in the right axilla region of BALB/C nude mice to generate tumor xenografts. On the day of implantation, the cell culture medium was replaced with fresh medium. Three hours later, the media was removed and the cells were collected and re-suspended in cold (4° C.) PBS prior to inoculation. The right axilla region of each mouse was cleaned with 70% ethanol prior to cell inoculation. Each animal was injected subcutaneously with desired cells in 200 μl of cell suspension in the right front flank via a 26-gauge needle. After implantation tumor volumes were measured twice weekly in two dimensions using a calliper. Tumor volume was calculated using the formula: $V=0.5\times(a\times b^2)$ where a and b are the long and short diameters of the tumor, respectively.

For in vivo efficacy studies, when the average tumor size reaches 100~200 mm³, animals were assigned into desired number of groups with 6-10 mice per group using a stratified randomization procedure. The groups consisted of a control group (no drug treatment), and different dose levels of Crystalline Form A* of Compound 1 Sesqui-Maleate treatment groups (ranged from 1-20 mg/kg). All doses were based on free-base weight. Drugs were administered by oral gavage once (qd) or twice (bid) daily; dosing frequency depended on the individual case for tumor growth. Treatments were administered by oral gavage (p.o.) in a volume of 10 ml/kg body weight. Body weight was assessed immediately before dosing and the volume dosed was adjusted accordingly. Individual body weights and tumor volumes were determined twice weekly, with mice being monitored daily for clinical signs of toxicity for the duration of the study. Mice were euthanized using carbon dioxide once their tumor volume reached 2000 mm³, the tumor was ulcerated, or body weight loss exceeded 20%. All group data was analyzed using the t test. If the p value was <0.05, it was considered to be statistically significant.

Tumor growth inhibition (TGI) was calculated using the following formula:

$$\% \text{ growth inhibition} = 100 \times \left(1 - \left(\frac{(\text{treated } t) - (\text{treated } to)}{(\text{placebo } t) - (\text{placebo } to)}\right)\right)$$

treated t=treated tumor volume at time t
treated $t_0$=treated tumor volume at time 0
placebo t=placebo tumor volume at time t
placebo $t_0$=placebo tumor volume at time 0

For PD study, when the average tumor size reaches 140-900 mm³, animals were assigned into desired number of groups with 4 mice per group using a stratified randomization procedure. The groups consisted of a control group (no drug treatment), and different dose levels of Crystalline Form A* of Compound 1 Sesqui-Maleate treatment groups (ranged from 1-20 mg/kg). All doses were based on free-base weight. Drugs were administered by oral gavage once (qd) or twice (bid) daily. All treatments were administered by oral gavage (p.o.) in a volume of 10 ml/kg body weight. Body weight was assessed immediately before dosing and the volume dosed was adjusted accordingly. Mice were euthanized using carbon dioxide at desired time points after dosing. Tumor tissues were dissected immediately after euthanization and snap-frozen into the tube pre-filled with MP beads using liquid nitrogen and stored at −80° C. prior to p-ERK assay. Five hundred microliters of complete lysis buffer was added to the frozen tumors with MP beads. Homogenization of tumor tissues was performed in MP homogenization unit and lysates were then spun down at 13,000 rpm for 10 min at 4° C. to remove insoluble material. Two microgram of protein lysates were used to measure phosphorylated ERK1/2 level by AlphaScreen® SureFire® p-ERK1/2 assay (PerkinElmer).

Results:

Compound 1 Sesqui-Maleate (Crystalline Form A*) has potent kinase inhibitory activity against B-RAF V600E, antiproliferative activity in cell-based assays and antitumor activity in xenograft models. Compound 1 Sesqui-Maleate (Crystalline Form A*) has marked antitumor activity against human A375 melanoma (B-RAF V600E mutation), LOX melanoma (B-RAF V600E mutation), Colo205 colorectal carcinoma (B-RAF V600E mutation), HT29 colorectal carcinoma (B-RAF V600E mutation), WiDr colorectal carcinoma (B-RAF V600E mutation), HCC827 lung carcinoma (EGFR mutation), and A431 epidermoid carcinoma (EGFR overexpression) xenografts in nude mice. In addition, Compound 1 Sesqui-Maleate (Crystalline Form A*) showed remarkable antitumor activity in human Calu-6 lung adenocarcinoma (K-RAS mutation) tumors when combined with docetaxel or the MEK inhibitor, selumetinib (AZD6244).

Oral administration of Crystalline Form A* of Compound 1 Sesqui-Maleate resulted in time-dependent and dose-dependent inhibition of ERK1/2 phosphorylation in A375 xenografts in mice. Inhibition of p-ERK levels in tumor tissues correlates well with plasma and tumor drug concentrations of Compound 1. Additionally, Compound 1 Sesqui-Maleate (Crystalline Form A*) and MEK inhibitor AZD6244 demonstrated a strong synergistic effect on inhibiting p-ERK in Calu-6 K-RAS mutant non-small cell lung adenocarcinoma xenograft models.

Test 5: Toxicology of Compound 1 Sesqui-Maleate (Crystalline Form A*)

A comprehensive nonclinical toxicity study program, including 28-day GLP studies in rats and dogs and several investigational studies, was conducted for the evaluation of the preclinical safety of Compound 1 Sesqui-Maleate (Crystalline Form A*). These studies took account the available regulatory guidance for preclinical development of anticancer drugs. In these studies, Compound 1 Sesqui-Maleate demonstrated a favorable toxicology and safety pharmacology profile. Safety pharmacological test results showed that Compound 1 Sesqui-Maleate (Crystalline Form A*) had no effect on respiration, blood pressure and circulatory function, and no effect on autonomic nervous system activity or the central nervous system. Additional toxicity testing results showed no teratogenic, mutagenic and reproductive toxicity Test 6: Pharmacokinetics of Crystalline Form A* of Compound 1 Sesqui-Maleate The fully-validated LC-MS/MS method was well used for the pharmacokinetic (PK) studies of Crystalline Form A* of Compound 1 Sesqui-Maleate in Sprague-Dawley rats and beagle dogs following single- and multiple-dose administrations.

Crystalline Form A* of Compound 1 Sesqui-Maleate has high oral bioavailability in both rats (51% to 102%) and dogs (41% to 82%). Its elimination half-lives ranged from 4.4 to 9.4 hours in rats and 3.3 to 4.9 hours in dogs after oral administration.

The kinetics was linear over the dose range of 0.5 to 15 mg/kg in rats and 1.5 to 15 mg/kg in dogs. After multiple dosing, a slight accumulation (~2-fold) was observed in rats. This slight accumulation was statistically significant in female rats, but not in male rats. No accumulation was noted after multiple dosing in dogs.

Test 7: ADME of Crystalline Form A* of Compound 1 Sesqui-Maleate

Compound 1 was widely distributed to various tissues, but was low in brain tissue, indicating the drug does not easily cross the blood-brain barrier. No significant induction effect on P450 enzymes in rat liver was found, no inhibitory activity on drug metabolism enzymes was found for Compound 1 Sesqui-Maleate, except for weak inhibition on CYP2C8 (IC50=1.03 µM) and CYP2C19 (IC50=1.96 µM). CYP3A was the major CYP isoform responsible for Compound 1 metabolism while CYP1A2, CYP2C8, CYP2C9, CYP2C19, and CYP2D6 contribute to the metabolism of Compound 1 to a lesser extent.

Test 8: Pharmacokinetic Comparison of the Crystalline Form A* of Compound 1 Sesqui-Maleate and Free Base Drugs and reagents: Crystalline Form A* of Compound 1 Sesqui-Maleate with particle sizes of D90=4.1 um, D10=1.5 um, D50=2.4 um after micronization. The material content (purity) was not less than 98.0%.

Experiment animals: Beagle dogs, male and female.

Pharmaceutical preparation: Weigh the appropriate amount of each substance and disperse in 0.5% sodium carboxymethyl cellulose (for the free base of Compound 1) or 0.5% methyl cellulose solution (for Compound 1 Sesqui-Maleate). Prepare a suspension at the desired concentration of Compound 1. All the doses and concentrations of Compound 1 were calculated with free base in this study.

Administration and sample collection: The dosing solutions will be freshly prepared prior to dose administration. The actual body weights and actual volume injected will be recorded accordingly. The dogs were fasted overnight and were allowed to intake food four hours after dosing. Each suspension was administrated orally to dogs at a dose ranged from 0.5 to 15 mg/kg. Blood samples (~1.0 mL) will be collected at pre-dose and at different times up to 36 hours postdosing via cephalic vein plexus. Whole blood will be processed by centrifugation and plasma samples will be collected and kept at freezer prior to analysis. Plasma samples were processed by protein precipitation. Concentrations of Compound 1 in the plasma samples were determined using a validated liquid chromatography-tandem mass spectrometry (LC-MS/MS) method. The plasma concentration-time data were analyzed using a non-compartmental model using Pharsight WinNonlin.

TABLE 20

The $C_{max}$ and area under the concentration-time curve for Compound 1 in free base and salts.

| Compound 1 | Oral Dose (mg/kg) | $C_{max}$ (ng/mL) | Dose-Normalized $AUC_{0-inf}$ (ng·h·kg·ml$^{-1}$·mg$^{-1}$) |
|---|---|---|---|
| Free Base (Lyophilized Amorphous Form) | 1 | 257 | 1512 |
| HCl salt of Compound 1 | 1 | 470 | 3640 |
| Sesqui-Maleate (Micronized Crystalline Form A*) | 0.5 | 342 | 4178 |
|  | 1 | 607 | 2960 |
|  | 1.5 | 861 | 3726 |
|  | 4.5 | 2884 | 4390 |
|  | 15 | 5307 | 2841 |

The above experiment showed that the $C_{max}$ (ng/mL) and $AUC_{0-inf}$ (ng·h/mL) of Crystalline Form A* of Compound 1 Sesqui-Maleate were as high as approximately 2-3 times that of the free base form. Therefore, Crystalline Form A* of Compound 1 Sesqui-Maleate has significantly better relative bioavailability than the free base of Compound 1 (amorphous form).

Test 9: Clinical Trials

Using Crystalline Form A* of Compound 1 Sesqui-Maleate to prepare capsules, a Phase I clinical safety study was completed on 25 subjects administered single doses of 5, 10, 20, 30, 40 and 50 mg. The results showed that 5-50 mg single doses were safe and well tolerated. The Compound 1 treatment caused partial responses in BRAF V600E melanoma patients, partial responses in BRAF V600E PTC patients and some anti-tumor activities in BRAF V600E CRC patients. 16 KRAS cancer patients were also recruited and treated, 3 PR and at least 12 patients survived more than 2.2 months (a mean PFS reported for KRAS cancer patients without treatment, see *Oncotarget*, 5, 19, 2014). These preliminary data demonstrated that Compound 1 Sesqui-Maleate (Crystalline Form A*) was effective in the treatment of Braf- and K-ras mutant cancers.

The foregoing examples and description of certain embodiments should be taken as illustrating, rather than as limiting the present invention as defined by the claims. As will be readily appreciated, numerous variations and combinations of the features set forth above can be utilized without departing from the present invention as set forth in the claims. All such variations are intended to be included within the scope of the present invention. All references cited are incorporated herein by reference in their entireties.

It is to be understood that, if any prior art publication is referred to herein, such reference does not constitute an admission that the publication forms a part of the common general knowledge in the art in any country.

In the claims which follow and in the preceding description of the invention, except where the context requires otherwise due to express language or necessary implication, the word "comprise" or variations such as "comprises" or "comprising" is used in an inclusive sense, i.e., to specify the presence of the stated features but not to preclude the presence or addition of further features in various embodiments of the invention.

The disclosures of all publications, patents, patent applications and published patent applications referred to herein by an identifying citation are hereby incorporated herein by reference in their entirety.

The invention claimed is:

1. A crystalline salt of 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one, which is selected from a hydrochloride salt, methanesulfonate salt, 2-hydroxyethanesulfonate salt, maleate salt or oxalate salt.

2. The salt of claim 1, wherein the salt has the structure of Formula (I):

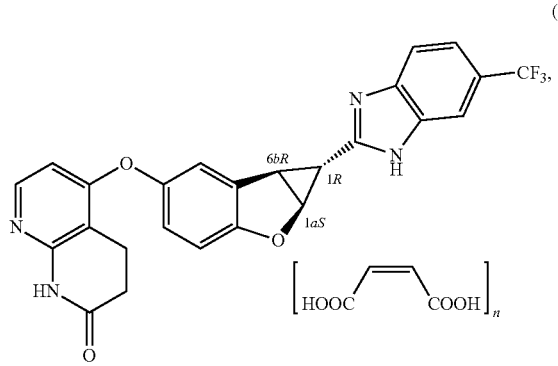

(I)

wherein n is a number from about 0.3 to about 1.5.

3. The salt of claim 2, wherein n is a number selected from the group consisting of 0.5±0.05, 1.0±0.1, and 1.5±0.2.

4. The salt of claim 2, wherein n is 0.5, 1.0, or 1.5.

5. The salt of claim 2, wherein the salt has the structure of Formula (II):

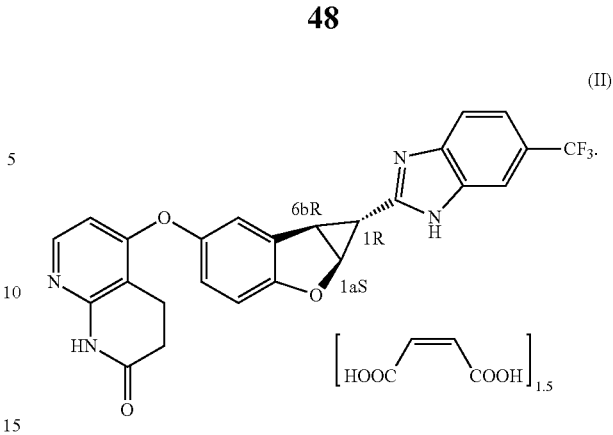

(II)

6. The salt of claim 5, which is in Crystalline Form A* having a powder X-ray diffraction pattern comprising seven or more diffraction peaks independently selected from the group consisting of: 6.3±0.2, 8.9±0.2, 9.4±0.2, 11.2±0.2, 12.6±0.2, 13.4±0.2, 17.9±0.2, 18.6±0.2, 18.8±0.2, 19.3±0.2, 20.1±0.2, 20.7±0.2, 21.2±0.2, 21.8±0.2, 22.4±0.2, 22.6±0.2, 23.3±0.2, 23.8±0.2, 24.7±0.2, 25.6±0.2, 26.1±0.2, 27.4±0.2, 28.3±0.2, 28.6±0.2, 29.0±0.2, 29.4±0.2, and 30.4±0.2 degrees 2θ.

7. The salt of claim 5, which is in Crystalline Form A** and having a single crystal structure, wherein:
   a) the single crystal structure demonstrates a two-dimensional structure in the bc plane;
   b) molecules of 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one and maleate anions are linked by an intermolecular interaction (N3 . . . N3) of about 2.797 Å and a hydrogen bond (N2-H2 . . . O4) of about 2.760 Å along b axis as illustrated in FIG. 14; and
   c) the molecules of 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one and the maleate anions are further linked by an intermolecular interaction (N3 . . . O7) of about 3.008 Å, an intermolecular interaction (N4 . . . O7) of about 2.715 Å, and a hydrogen bond (N1-H1 . . . O8) of about 2.659 Å along c axis as illustrated in FIG. 14.

8. The salt of claim 5, which is in Crystalline Form A having a powder X-ray diffraction pattern comprising three or more diffraction peaks independently selected from the group consisting of: 8.3±0.2, 11.2±0.2, 17.9±0.2, 18.4±0.2, 18.6±0.2, 19.3±0.2, 20.8±0.2, and 22.5±0.2 degrees 2θ.

9. The salt of claim 2 selected from:
   (a) a Crystalline Form B having a powder X-ray diffraction pattern comprising three or more diffraction peaks independently selected from the group consisting of: 11.1±0.2, 15.8±0.2, 17.7±0.2, 18.4±0.2, 19.6±0.2, 22.3±0.2, 23.1±0.2, and 28.8±0.2 degrees 2θ;
   (b) a Crystalline Form C having a powder X-ray diffraction pattern comprising three or more diffraction peaks independently selected from the group consisting of: 3.1±0.2, 8.8±0.2, 11.2±0.2, 17.8±0.2, 18.5±0.2, 19.3±0.2, 20.1±0.2, 20.7±0.2, 21.9±0.2, and 22.4±0.2 degrees 2θ;
   (c) a Crystalline Form D having a powder X-ray diffraction pattern comprising three or more diffraction peaks independently selected from the group consisting of: 8.9±0.2, 14.9±0.2, 16.7±0.2, 17.8±0.2, 19.9±0.2, 20.4±0.2, 20.9±0.2, and 26.9±0.2 degrees 2θ;

(d) a Crystalline Form F having a powder X-ray diffraction pattern comprising three or more diffraction peaks independently selected from the group consisting of: 12.9±0.2, 17.0±0.2, 18.5±0.2, 19.4±0.2, 20.5±0.2, 22.5±0.2, and 24.1±0.2 degrees 2θ;

(e) a Crystalline Form G having a powder X-ray diffraction pattern comprising seven or more diffraction peaks independently selected from the group consisting of: 3.4±0.2, 5.6±0.2, 7.0±0.2, 10.3±0.2, 10.9±0.2, 11.7±0.2, 12.4±0.2, 13.1±0.2, 14.0±0.2, 14.9±0.2, 16.4±0.2, 17.4±0.2, 18.6±0.2, 19.3±0.2, 20.1±0.2, 21.0±0.2, 21.9±0.2, 23.6±0.2, 24.2±0.2, 25.6±0.2, and 26.4±0.2 degrees 2θ;

(f) a Crystalline Form H having a powder X-ray diffraction pattern comprising seven or more diffraction peaks independently selected from the group consisting of: 6.3±0.2, 9.0±0.2, 10.1±0.2, 11.2±0.2, 12.7±0.2, 14.5±0.2, 16.1±0.2, 16.6±0.2, 17.9±0.2, 18.1±0.2, 18.5±0.2, 19.0±0.2, 20.1±0.2, 21.9±0.2, 22.4±0.2, 23.9±0.2, 25.1±0.2, 26.2±0.2, and 28.7±0.2 degrees 2θ;

(g) a Crystalline Form I having a powder X-ray diffraction pattern comprising five or more diffraction peaks independently selected from the group consisting of: 3.1±0.2, 5.5±0.2, 6.8±0.2, 10.8±0.2, 11.5±0.2, 13.7±0.2, 16.1±0.2, 16.3±0.2, 17.8±0.2, 19.8±0.2, 21.5±0.2, 23.8±0.2, 24.4±0.2, and 28.3±0.2 degrees 2θ;

(h) a Crystalline Form J having a powder X-ray diffraction pattern comprising seven or more diffraction peaks independently selected from the group consisting of: 5.5±0.2, 8.2±0.2, 10.9±0.2, 11.3±0.2, 13.6±0.2, 14.8±0.2, 15.8±0.2, 17.4±0.2, 18.0±0.2, 19.1±0.2, 19.8±0.2, 20.0±0.2, 20.4±0.2, 21.1±0.2, 21.9±0.2, 22.6±0.2, 23.4±0.2, 24.1±0.2, 25.0±0.2, 26.1±0.2, 26.9±0.2, 27.3±0.2, 28.4±0.2, 29.1±0.2, 33.1±0.2, and 35.9±0.2 degrees 2θ;

(i) a Crystalline Form K having a powder X-ray diffraction pattern comprising seven or more diffraction peaks independently selected from the group consisting of: 3.1±0.2, 8.9±0.2, 9.3±0.2, 11.2±0.2, 16.7±0.2, 17.9±0.2, 18.6±0.2, 18.8±0.2, 19.4±0.2, 20.2±0.2, 21.9±0.2, 22.4±0.2, 23.4±0.2, 23.9±0.2, 24.6±0.2, 26.2±0.2, 27.4±0.2, 28.5±0.2, 29.4±0.2, and 30.4±0.2 degrees 2θ;

(j) a Crystalline Form L having a powder X-ray diffraction pattern comprising diffraction peaks: 9.7±0.2 and 14.1±0.2 degrees 2θ; or (k) a Crystalline Form M having a powder X-ray diffraction pattern comprising seven or more diffraction peaks independently selected from the group consisting of: 5.0±0.2, 9.3±0.2, 11.3±0.2, 14.9±0.2, 15.9±0.2, 17.4±0.2, 18.0±0.2, 18.7±0.2, 19.4±0.2, 20.2±0.2, 22.1±0.2, 23.4±0.2, 24.3±0.2, 25.4±0.2, 26.5±0.2, 27.5±0.2, 28.5±0.2, and 29.3±0.2 degrees 2θ.

10. The salt of claim 2, which is substantially similar to a powder X-ray diffraction pattern selected from the group consisting of FIG. 2, FIG. 16, FIG. 17, FIG. 18, FIG. 19, FIG. 20, FIG. 21, FIG. 22, FIG. 23, FIG. 24, FIG. 25, FIG. 26, FIG. 27, FIG. 28, and FIG. 33.

11. The salt of claim 1, wherein the salt is 5-(((1R,1aS, 6bR)-1-(6-(trifluoromethyl)-1H-benzo[d]imidazol-2-yl)-1a, 6b-dihydro-1H-cyclopropa[b]benzofuran-5-yl)oxy)-3,4-dihydro-1,8-naphthyridin-2(1H)-one Maleate (1:1), which is in Crystalline Form N having a powder X-ray diffraction pattern comprising seven or more diffraction peaks independently selected from the group consisting of: 3.30±0.2, 6.61±0.2, 9.88±0.2, 11.73±0.2, 13.14±0.2, 15.23±0.2, 16.56±0.2, 17.94±0.2, 18.72±0.2, 19.34±0.2, 19.93±0.2, 20.76±0.2, 22.04±0.2, 22.95±0.2, 23.86±0.2, 25.19±0.2, 26.61±0.2, 28.36±0.2, 30.13±0.2, 31.36±0.2, 33.49±0.2, and 37.22±0.2 degrees 2θ.

12. The salt according to claim 11, which is substantially similar to a powder X-ray diffraction pattern as shown in FIG. 33.

13. A method for preparing the salt of claim 2, comprising:

(a) dissolving free base or a salt other than maleate of 5-(((1R,1aS,6bR)-1-(6-(trifluoromethyl)-1H-benzo[d] imidazol-2-yl)-1a,6b-dihydro-1H-cyclopropa[b]benzofuran-5-yl)oxy)-3,4-dihydro-1,8-naphthyridin-2(1H)-one in a solvent or solvent mixture to form a solution or suspension; mixing the resultant solution or suspension with maleic acid to form a mixture; and precipitating out 5-(((1R,1aS,6bR)-1-(6-(trifluoromethyl)-1H-benzo[d]imidazol-2-yl)-1a,6b-dihydro-1H-cyclopropa [b]benzofuran-5-yl)oxy)-3,4-dihydro-1,8-naphthyridin-2(1H)-one maleate salt in a target crystalline form;

(b) dissolving or suspending 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one sesqui-maleate salt in a solvent or solvent mixture; and precipitating out 5-(((1R,1aS,6bR)-1-(6-(trifluoromethyl)-1H-benzo[d] imidazol-2-yl)-1a,6b-dihydro-1H-cyclopropa[b]benzofuran-5-yl)oxy)-3,4-dihydro-1,8-naphthyridin-2(1H)-one maleate salt in a target crystalline form;

(c) storing a crystalline 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1, 8-naphthyridin-2(1H)-one maleate salt for an extended period to obtain a target crystalline form;

(d) heating a crystalline or amorphous 5-(((1R,1aS,6bR)-1-(6-(trifluoromethyl)-1H-benzo[d]imidazol-2-yl)-1a, 6b-dihydro-1H-cyclopropa[b]benzofuran-5-yl)oxy)-3, 4-dihydro-1,8-naphthyridin-2(1H)-one maleate salt to an elevated temperature, and cooling the salt to obtain a target crystalline form; and (e) exposing a crystalline or amorphous 5-(((1R,1aS, 6bR)-1-(6-(trifluoromethyl)-1H-benzo[d]imidazol-2-yl)-1a,6b-dihydro-1H-cyclopropa[b]benzofuran-5-yl) oxy)-3,4-dihydro-1,8-naphthyridin-2(1H)-one maleate salt to a vapor of a solvent to obtain a target crystalline form.

14. The method of claim 13, wherein the step (a) or (b) further comprises one or more steps independently selected from heating, filtering to remove undissolved impurities, distilling solvent, adding a counter solvent or solvent mixture, adding crystal seeds, adding precipitation inducing agent(s), cooling, precipitating, or filtering to collect the crystalline product.

15. The method of claim 13, comprising the step (a) or (b), wherein the solvent or solvent mixture is selected from the group consisting of water, lower alkyl alcohols, ketones, ethers, esters, lower aliphatic carboxylic acids, lower aliphatic nitriles, optionally halogenated aromatic solvents, and combinations thereof.

16. The method of claim 13, wherein the solvent is isopropanol, ethanol, methanol, acetone, THF, 1,4-dioxane, acetic acid, acetonitrile, water, or a combination thereof.

17. The method of claim 13, comprising said procedure (a), wherein said free base is an isolated and purified free base, an isolated but unpurified free base, or a crude reaction product containing the free base.

18. The method of claim 13, comprising said procedure (c), wherein said extended period is at least three days, at least one week, or at least two weeks.

19. The method of claim 13, comprising said procedure (d), wherein said elevated temperature is at least 40° C., at least 60° C., at least 80° C., or at least 100° C., but lower than decomposition temperature of the sesqui-maleate salt.

20. The method of claim 13, comprising said procedure (e), wherein said vapor is a vapor of acetic acid.

21. The method of claim 13, wherein:
1) the step (a) or (b) comprises using isopropanol-water (v/v>60/40) as the solvent to produce Crystalline Form A*;
2) the step (a) or (b) comprises using acetone as the solvent to produce Crystalline Form A**;
3) the step (a) or (b) comprises using an IPA-water (v:v=4:1) mixture as the solvent to produce Crystalline Form A;
4) the step (a) or (b) comprises using 1,4-dioxane as the solvent to produce Crystalline Form B;
5) the step (a) or (b) comprises using ethanol as the solvent to produce Crystalline Form C;
6) the step (a) or (b) comprises using methanol as the solvent to produce Crystalline Form D;
7) the step (a) or (b) comprises using an acetonitrile-water (v:v=1:1) mixture as the solvent to produce Crystalline Form F;
8) the step (a) or (b) comprises using an acetic acid-water mixture as the solvent to produce Crystalline Form G;
9) the step (a) or (b) comprises using tetrahydrofuran (THF) as the solvent to produce Crystalline Form H;
10) the step (a) or (b) comprises using an IPA-water (v:v=3:1) mixture as the solvent to produce Crystalline Form I;
11) the step (c) comprises storing Crystalline Form D at ambient temperature for two weeks to produce Crystalline Form K;
12) the step (c) comprises storing Crystalline Form J at ambient temperature for two weeks to produce Crystalline Form M; and
13) the step (d) comprises heating Crystalline Form G to 140° C. and then cooling to ambient temperature to produce Crystalline Form L; or
14) the step (e) comprises interaction of Crystalline Form A with acetic acid vapor to produce Crystalline Form J.

22. A pharmaceutical composition comprising a therapeutically effective amount of the salt of claim 2 and a pharmaceutically acceptable carrier.

23. The pharmaceutic composition of claim 22, wherein the pharmaceutical composition is suitable for oral administration.

24. The pharmaceutical composition of claim 22, wherein the pharmaceutical composition is in the form of tablet or capsule.

25. The pharmaceutical composition of claim 22, wherein the unit dosage of the tablet or capsule comprises 5 mg to 80 mg of the salt of claim 2.

26. The pharmaceutical composition of claim 22, wherein the weight percentage of the salt in the pharmaceutical composition is 1-99%.

27. A method of treating cancer in a subject, comprising administering to said subject a therapeutically effective amount of the salt of claim 2, wherein the cancer is selected from the group consisting of brain cancer, lung cancer, kidney cancer, bone cancer, liver cancer, bladder cancer, breast, head and neck cancer, ovarian cancer, melanoma, skin cancer, adrenal cancer, cervical cancer, colorectal cancer, lymphoma, or thyroid tumors and their complications.

28. A method of treating cancer in a subject, comprising administering to said subject a therapeutically effective amount of the salt of claim 2, wherein the cancer is a BRAF, NRAS or KRAS mutant cancer selected from the group consisting of brain cancer, lung cancer, kidney cancer, bone cancer, liver cancer, bladder cancer, breast, head and neck cancer, ovarian cancer, melanoma, skin cancer, adrenal cancer, cervical cancer, colorectal cancer, lymphoma, and thyroid cancer.

29. The method of claim 28, wherein the salt is 1-100 mg/day, and the administration frequency is one to three times a day.

30. The method of claim 28, wherein the administered dosage of the salt is 5-50 mg/day, and the administration frequency is one to three times a day.

31. The method of claim 28, wherein the administered dosage of the salt is 10-40 mg/day, and the administration frequency is one time a day.

32. The method of claim 27, wherein the salt is 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one maleate in a crystalline form selected from the group consisting of Crystalline Forms A*, A**, A, B, C, D, F, G, H, I, J, K, L, M and N.

33. The method of claim 28, wherein the salt is 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one maleate in a crystalline form selected from the group consisting of Crystalline Forms A*, A**, A, B, C, D, F, G, H, I, J, K, L, M and N.

34. The method of claim 27, wherein the salt is 1-100 mg/day, and the administration frequency is one to three times a day.

35. The method of claim 27, wherein the administered dosage of the salt is 5-50 mg/day, and the administration frequency is one to three times a day.

36. The method of claim 27, wherein the administered dosage of the salt is 10-40 mg/day, and the administration frequency is one time a day.

37. A process for preparing a crystalline 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one sesqui-maleate comprising:
a) mixing a mixture of 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one and maleic acid in a solvent comprising i-PrOH at about 50° C., or
b) mixing 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one with a mixture or a suspension or a solution of maleic acid in a solvent comprising i-PrOH at about 50° C., or
c) mixing a mixture or a suspension or a solution of 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one in a solvent comprising i-PrOH with maleic acid at about 50° C., wherein in each of (a), (b) and (c), the amount of i-PrOH is greater than 40 vol % of the total volume of the solvent comprising i-PrOH.

38. The process according to claim 37, wherein the solvent comprising i-PrOH is a mixed solvent of i-PrOH and water.

39. The process according to claim 37, further comprising adding some crystal seeds into the resultant mixture after cooling to room temperature, and then letting the mixture stand for a certain duration.

40. A process for preparing a crystalline form of 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one maleate (1:1) comprising mixing a crystalline form of 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one sesqui-maleate with methanol.

41. The process according to claim 40, wherein the mixing is performed with stirring.

42. The process according to claim 40, wherein the crystalline form of 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one maleate (1:1) is Form N.

43. The process according to claim 40, wherein the crystalline form of 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one maleate is selected from the group consisting of Crystalline Forms A*, A**, A, B, C, D, F, G, H, I, J, K, L and M.

44. The pharmaceutical composition of claim 22, wherein the salt is 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyridin-2(1H)-one maleate in a crystalline form selected from the group consisting of Crystalline Forms A*, A**, A, B, C, D, F, G, H, I, J, K, L, M and N.

45. The process according to claim 38, wherein in each of (a), (b) and (c), the amount of i-PrOH is greater than 60 vol % of the mixed solvent of i-PrOH and water.

46. The process according to claim 38, wherein in each of (a), (b) and (c), the amount of i-PrOH is greater than 90 vol % of the mixed solvent of i-PrOH and water.

* * * * *